United States Patent [19]
Schnable et al.

[11] Patent Number: 6,060,644
[45] Date of Patent: *May 9, 2000

[54] ISOLATION AND USE OF CUTICULAR LIPID GENES

[75] Inventors: Patrick S. Schnable; Donald S. Robertson, both of Ames; Joel D. Hansen, Slater; Basil J. Nikolau, Ames; Xiaojie Xu, Ames; Yiji Xia, Ames, all of Iowa

[73] Assignee: Iowa State University Research Foundation, Inc., Ames, Iowa

[*] Notice: This patent issued on a continued prosecution application filed under 37 CFR 1.53(d), and is subject to the twenty year patent term provisions of 35 U.S.C. 154(a)(2).

[21] Appl. No.: 08/581,148

[22] Filed: Dec. 29, 1995

Related U.S. Application Data

[63] Continuation-in-part of application No. 08/218,028, Mar. 24, 1994, abandoned.

[51] Int. Cl.[7] .............................. A01H 5/00; C12N 5/04; C12N 15/82
[52] U.S. Cl. ....................... 800/281; 800/298; 435/419; 435/468
[58] Field of Search ..................... 536/23.6; 435/152.3, 435/240.4, 320.1, 419, 468; 800/205, DIG. 69, 281, 298

[56] References Cited

PUBLICATIONS

Lewin R., Science 237:1570 Sep. 25, 1987.
Agrawal et al. "Biosynthesis of Very Long Chain Fatty Acids in Microsomes from Epidermal Cells of *Allium porrum* L.," *Arch. Biochem. Biophys.*, 230, 580–589 (1984).
Agrawal et al., "Characterization and Solubilization of an Acyl Chain Elongation System in Microsomes of Leek Epidermal Cells," *Arch. Biochem. Biophys.*, 240, 154–165 (1985).
Bianchi, "Glossy Mutants: Level of Action and Level of Analysis," *Maize Breeding and Genetics*, pp. 533–550, Walden, ed., John Wiley and Sons, New York, New York (1978).
Bianchi et al., "Biosynthesis Pathways of Epicuticular Wax of Maize as Assessed by Mutation, Light, Plant Age and Inhibitor Studies," *Maydica*, 30, 179–198 (1985).
Brown et al., "Molecular Analysis of Multiple Mutator–Derived Alleles of the Bronze Locus of Maize," *Genetics*, 122, 439–445 (1989).
Gibson et al., "Chromosome walking in *Arabidopis thaliana* using Yeast Artificial Chromosomes," *Methods in Arabidospis Research*, pp. 119–123, Koncz et al., eds., World Scientific, Singapore (1992).
Grill et al., "Construction and characterization of yeast artificial chromosome library of Arabidopsis which is suitable for chromosome walking," *Mol. Gen. Genet.*, 226, 484–490 (1991).

Hansen et al., *Plant Physical*, 102 (i) , 93 (Abstratct #519, "Molecular Cloning and Characterization of Plant Cuticular Wax Genes") (May 1993).
Kolattukudy et al., "The Biochemistry of Plant Cuticular Lipids," *Proq. Chem. Fats Other Lipids*, 13, 121–175 (1973).
Kolattukudy et al., "Biochemistry of Plant Waxes," *Chemistry and Biochemistry of Natural Waxes*, pp. 571–645, Kolattukudy, ed., Elsevier Press, New York, New York (1976).
Kolattukudy, "Cutin, Suberin, and Waxes," *Biochem. of Plants*, 4, 571–645, Stumpf et al., eds., Academic Press, New York, New York (1980).
Kolattukudy, "Structure, Biosynthesis, and Biodegradation of Cutin and Suberin," *Ann. Rev. Plant Physiol.*, 32, 539–567 (1981).
Lardizabal et al., "Substrate Tagging, Solubilization and Partial Purification of Jojoba (Simmondsia chinensis) Embryo Fatty Acyl–Coa: Fatty Alcohol Acyl Transferase," *Plant Physiol.* (Suppl.) , 102, 93 (1993).
Lazo et al., "A DNA Transformation–Competent Arabidopsis Genetic Library in Agrobacterium," *Bio/Technology*, 9, 963–967 (1991).
Lemieux et al., "GC–MS Analysis of the Wax of Eceriferum (CER) Mutants of *Arabidopsis thaliana* and Isolation of CER Genes fron T–DNA Tagged Arabidopsis Mutant Lines," *Plant Physiol.* (Suppl.) , 99, 14 (1992).
McNevin et al., "Isolation and Characterization of Eceriferum (ecr) Mutants Induced by T–DNA Insertions in Arabidopsis Thaliana" *Genome*, 36 (3), 610–618 (Jun. 1983).
Meyerowitz, "Introduction to the Arabidopsis genome," *Methods in Arabidopsis Research*, pp. 100–118, Koncz et al., eds., World Scientific, Singapore (1992).
Moose et al, "Molecular Cloning of the glossy–15 Locus, a Cell–Specific Regulator of Epidermal Differentiation," *Abstracts*, 35th Annual Maize 1993, Evans et al., eds. (1993).
Schnable et al, "Genetic Approaches to Isolating Maize and Arabidopsis Genes Involved in Cuticular Wax Biosynthesis," *Current Topics in Plant Physiology*, 9, 196–206 (1993).
Schnable et al., "Transposon Tagging Agronomically Important Loci in Maize," *Proceedings, 28th Annual Illinois Corn Breeder's School* (1992).

(List continued on next page.)

Primary Examiner—Elizabeth F. McElwain
Attorney, Agent, or Firm—Leydig, Voit & Mayer, Ltd.

[57] ABSTRACT

The present invention relates to cuticular lipid genes, their gene products, and methods of use thereof, for the generation of new plant varieties having novel environmental, disease and pest resistance. In particular, certain isolated or enriched nucleic acids specifying cuticular lipid genes, or portions thereof, are disclosed.

13 Claims, 5 Drawing Sheets

OTHER PUBLICATIONS

Stinard et al., "Genetic Isolation, Cloning, and Analysis of a Mutator–Induced, Dominant Antimorph of the Maize amylose extenderl Locus," *Plant Cell*, 5, 1555–1566 (1993).

Tulloch, "Chemistry of Waxes of Higher Plants," *Chemistry and Biochemistry of Natural Waxes*, pp. 235–287, Kolattukudy, ed., Elsevier Press, New York, New York (1976).

Vogel et al., *J. Cellular Biochemistry, 17A*, 32 (Abstract #A327) (Jan. 9, 1993).

von Wettstein–Knowles, "Genes, Elongases and Associated Enzyme Systems in Epicuticular Wax Synthesis," *The Metabolism, Structure, and Function of Plant Lipids*, pp. 489–498, Stump et al., eds., Elsevier Press, North–Holland, Amsterdam (1987).

Walbot, "Strategies for Mutagenesis and Gene Cloning Using Transposon Tagging and T–DNA Insertional Mutagenesis," *Annu. Rev. Plant Physiol. Plant Mol. Biol.*, 43, 49–82 (1992).

Ward et al., "Isolation of single–copy–sequence clones from a yeast artificial chromosome library of randomly–sheared *Arabidopsis thaliana* DNA," *Plant Mol. Biol.*, 14, 561–568 (1990).

Vander Knol et al. 1988 Bio/Techniques 6: 958–976.

Vander Knol et al. 1990 Plant Molec Biol 14: 457–466.

Finnegan et al. 1994 Bio/Technology 12: 883–888.

ISOLATION AND USE OF CUTICULAR LIPID GENES

RELATED APPLICATION

This application is a continuation-in-part of application Ser. No. 08/218,028, filed Mar. 24, 1994, now abandoned entitled "Isolation and Use of Cuticular Lipid Genes."

GOVERNMENT SUPPORT

This invention was made with government support under Grant No. DCB-9017963 awarded by the National Science Foundation. The U.S. Government has certain rights in the invention.

TECHNICAL FIELD OF THE INVENTION

The present invention relates to the field of genetically engineered biosynthesis of plant lipids, and specifically relates to the isolation and use of cloned cuticular lipid genes.

BACKGROUND OF THE INVENTION

Plant surfaces are covered with a complex mixture of lipids, which are thought to be synthesized by the cells of the epidermal tissue, the outermost single layer of cells. In addition to functioning as a water barrier, the surface lipids of plants have been suggested to function, inter alia, in frost resistance, in plant-pathogen interactions, and to provide protection from UV irradiation. Despite these diverse and important physiological functions of the surface lipids of plants, little is known about the biochemical and molecular genetic mechanisms that regulate their biogenesis. In particular, only subsequent to the filing of the parent of this application were any of the genes that encode regulatory or enzymatic functions in the cuticular lipid biosynthetic pathway cloned, despite the earlier identification in the art of genes believed to be involved therein.

The outermost barrier of the aerial portions of plants, the cuticle, consists of a meshwork ("cutin") of cross-esterified polymerized hydroxy-fatty acids, which are embedded in a complex mixture of nonpolar lipids, commonly referred to as the cuticular waxes. Maintenance of this interface between a plant and its environment permits sequestration of the highly regulated internal biochemical processes crucial for the plant's survival and the establishment of a water barrier. See Martin and Juniper, *The Cuticle of Plants* (Edward Arnold Ltd., Edinburgh, UK, 1970); and Kolattukudy, *Ann. Rev. Plant Physiol.*, 32, 539–567 (1981). Chemical analyses of the cuticle have shown that its composition is genetically controlled and is unique to each species. See Kolattukudy and Walton, *Prog. Chem. Fats Other Lipids*, 13, 121–175 (1973); Kolattukudy et al., in *Chemistry and Biochemistry of Natural Waxes* (Kolattukudy, ed., Elsevier Press, New York, N.Y., 1976), pages 289–347; Tulloch, in *Chemistry and Biochemistry of Natural Waxes*, supra, pages 235–287; and Kolattukudy, in *The Biochemistry of Plants: A Comprehensive Treatise*, Vol. 4 (Stumpf and Conn, eds., Academic Press, New York, N.Y., 1980), pages 571–645.

The biochemistry of cuticular lipid biosynthesis has been investigated by: (1) monitoring the in vivo incorporation of radioactively labeled precursors into the lipids; (2) observing the effect of inhibitors on lipid composition; and (3) determining the in vitro activity of specific enzymes involved in lipid biosynthesis. These investigations have led to the formulation of a hypothesized general scheme of lipid biosynthesis, which is depicted in FIG. 1. See Kolattukudy and Walton, supra (1973); Kolattukudy et al., supra (1976); Tulloch, supra (1980); and Kolattukudy, supra (1980).

The cuticle contains many lipid compounds, the majority of which are derivatives of fatty acids. For example, cutin is composed of fatty acid derivatives such as diols, hydroxy fatty acids, dihydroxy fatty acids and dicarboxylic fatty acids, which are polymerized by ester linkages. The resultant polymers are embedded in the wax components of the cuticle, which is composed of a mixture of hydrocarbons, including n-alkanes, branched alkanes, cyclic alkanes, alkenes, ketones, ketols, alcohols, aldehydes, diols, acids, esters, and the like.

The major components of the cuticular wax, another category of lipids, are very long-chain fatty acids ("VLCFAs") and their derivatives. VLCFAs are considered to be the products of de novo fatty acid biosynthesis, which occurs in plastids, and subsequent elongation by specific elongases that are understood to be localized on the endoplasmic reticulum membranes. Partial purification and characterization of these elongases have been reported. See, for example, Agrawal et al., *Arch. Biochem. Biophys.*, 230, 580–589 (1984); and Agrawal and Stumpf, *Arch. Biochem. Biophys.*, 240, 154–165 (1985). Fatty acyl aldehydes and alcohols are the products of the sequential reduction of the appropriate fatty acid. Wax ester formation probably occurs via a transferase type reaction utilizing fatty acyl-CoAs or phospholipids as the donor of a fatty acid, which is transferred to a fatty alcohol (Kolattukudy et al., supra (1976)). Indeed, a fatty acyl-CoA-fatty alcohol transacylase has been partially purified from young broccoli leaves, and more recently, a similar enzyme has been purified from jojoba seeds (Lardizabal et al., *Plant Physiol.* (Suppl.), 102, 93 (1993)). As stated previously, prior to the filing of the parent of this application, none of the enzymes involved in cuticular lipid biosynthesis were cloned, accordingly no readily available source of them has been available. Thus, there has existed no ability to use them to alter the cuticular lipid components of a plant or its seed oils, and no ability to use them for in vitro synthesis of the aforementioned lipids.

Maize is a well-characterized experimental plant system that has been the subject of prior investigations of cuticular lipids. The cuticular wax of wildtype maize seedlings is composed of long-chain alcohols (63%), aldehydes (20%), alkanes (1%) and esters of alcohols and long-chain fatty acids (16%). The alcohols and aldehydes are predominantly 32 carbons in length, i.e., n-dotriacontanol (99% of all the alcohols) and dotriacontaldehyde (96% of the aldehydes). The alkane fraction is mainly 31 carbons in length, i.e., hentriacontane (Bianchi et al., *Maydica*, 30, 179 (1985)). Developmental differences in the quantity and quality of cuticular wax in maize have been noted in that adult maize leaves, as compared to juvenile leaves, have considerably less cuticular wax, which is of a different composition.

Seventeen loci (the glossy or gl genes) have been identified in standard crossbreeding studies of maize as affecting the quantity and composition of cuticular lipids on seedling leaves (namely, glossy1, glossy2, glossy3, glossy4, glossy5, glossy6, glossy8, glossy9, glossy11, glossy14, glossy15, glossy17, glossy18, glossy19, glossy20, glossy21, glossy22), although, as further explained hereinbelow, one of these genes (i.e., glossy15) apparently encodes a developmental control of the activity of cuticular lipid genes. The glossy15 gene also affects cell shape, cell wall composition, and the presence/absence of adult-type epidermal hairs. Hence, it mediates the entire juvenile to adult transition, i.e., it does not regulate cuticular wax biosynthesis per se. See Moose et al., *Plant Cell*, 6, 1343–1355 (1994) and Evans et al., *Development*, 120, 1971–1981 (1994).

Mutant seedlings are usually identified because applied water forms droplets on their leaf surfaces (Bianchi, in *Maize Breeding and Genetics* (Walden, ed., John Wiley and Sons, New York, N.Y., 1978), page 533); in addition, they present a "glossy" appearance. Four of the 17 glossy loci are members of duplicate gene pairs (gl5 & gl20, and gl21 & gl22), i.e., a seedling must be homozygous mutant for both members of such pairs before it expresses the mutant phenotype. Of the 17 glossy loci, 12 have been relatively precisely mapped genetically and three more have been mapped to a chromosome or chromosome arm.

Comparisons of the composition of the waxes produced by seedlings homozygous for each of the various glossy mutants to the wax of wildtype seedlings have been used to identify putatively the biochemical steps encoded by many of the glossy genes. In view of these data, it has been suggested that cuticular wax biosynthesis occurs via two hypothesized pathways, namely ED-I and ED-II (Bianchi et al., supra). The ED-II pathway is thought to be active throughout the life of the plant, with the end product being mainly esters. The ED-I pathway is thought to be active only during the seedling stage of the plant and the end-products of this pathway are mainly alcohols, aldehydes and alkanes.

However, a comparison between the chain lengths of the alcohol moiety of the esters and the chain lengths of the free alcohols in the wax of a number of different glossy mutants suggests an alternative hypothesis that cuticular wax biosynthesis in maize is the result of four reductive systems that are juxtaposed on elongase system(s) (von Wettstein-Knowles, in *The Metabolism, Structure, and Function of Plant Lipids* (Stumpf et al., Elsevier/North-Holland, Amsterdam, 1987), pages 489–498). One of these reductive systems operates in young seedlings (R1) and appears to produce free alcohols and free aldehydes. The second reductase system (R2) operates in mature plants and catalyzes the esterification of the alcohol products. It has been suggested that the glossy1, glossy8 and glossy18 genes may affect a fatty acid elongation reaction that feeds the R1 reductive system. The glossy7 gene (which is allelic to glossy6), on the other hand, may affect a third reductive system (R3) that provides C28 and C30 alcohols for ester formation. And lastly, according to this interpretation, the glossy15 gene may affect a fourth reductive system (R4) that provides alcohols of even shorter chain length for ester formation. However, more recent analyses of glossy15 have established that glossy15 may not be involved in cuticular wax biosynthesis per se, but rather have an indirect or incidental role in plant cuticle formation, as in the control of the phase change between juvenile and adult leaves (Moose and Sisco, in Abstracts, 35th Annual Maize 1993; and Evans and Poethig, 1993). Mutations at glossy15 result in an early transition from the juvenile to adult stage, resulting in seedling leaves with adult-type wax. Accordingly, it appears that all of the maize glossy mutants are involved in lipid biosynthesis; all but one of these genes (i.e., glossy15) apparently provide the enzymes and, perhaps, the cofactors that mediate lipid biosynthesis. One of the mutants (i.e., glossy 15) apparently relates to the developmental control of the activity of the indicated genes, as well as that of other genes.

Another experimental plant system for the study of cuticular lipids is Arabidopsis. The chemical composition and the genetics of the cuticular lipids of Arabidopsis is less well-defined than for maize. Preliminary analyses of the lipids of Arabidopsis indicate that the composition of the Arabidopsis cuticular wax is distinct from the wax of maize (Hannoufa et al., *Phytochem.*, 33, 851–855 (1993); and Jenks et al., *Plant Physiol.*, 108, 396–377 (1995)). The predominant cuticular lipids of Arabidopsis are alkanes, ketones and secondary alcohols. In contrast to maize, where fatty acyl aldehydes are reduced to primary alcohols, in Arabidopsis a considerable portion of the aldehydes are decarboxylated to form alkanes, which are then further metabolized to ketones and secondary alcohols. Thus, it appears that the Arabidopsis pathway is divergent from that which occurs in maize. However, based on evolutionary considerations, it is considered likely that many of the enzymes involved in the cuticular lipid synthesis of one plant are related in sequence and function to those of another plant. It is understood that fatty acid synthesis occurs in plastids in all plants. Fatty acids of $C_{16}$–$C_{18}$ content are transported from the plastid to the cytosol, where it is believed that evolutionarily conserved elongation enzymes act on the de novo fatty acids to form long-chain fatty acids, very long-chain fatty acids, and other lipid compounds. These enzymes are believed to be the same or ancestrally related between species of plants, i.e., they are likely to have related nucleic acid and amino acid sequences.

As with maize, mutations have defined loci that affect the biosynthesis and/or deposition of the cuticular waxes of Arabidopsis. Many of these 21 loci, termed the eceriferum (CER) loci, present readily identifiable phenotypes (Koornneef et al., *J. Hered.*, 80, 118–122 (1989)); some have pleiotropic effects on fertility. Analysis of one of these mutants, at the cer2 gene, indicates that the mutant allele affects changes in the lipid classes and in the predominant carbon chain length of the acyl moieties.

Being at the boundary between the organism and its environment, it would be desirable to control the lipid content of plant cuticle, the biochemical and genetic regulatory mechanisms of which are not well understood. Doing so would facilitate the generation of new plant varieties having altered abilities to conserve water, prevent loss of extracellular components by leeching, and resisting injury from environmental effects such as wind and frost. Because the cuticle is also instrumental in mediating the interaction between plants and other organisms, such as fungi, insects, and bacteria, control of the lipid content of cuticle would also impact on the generation of resistance to these pests. Furthermore, because the nature of the cuticle greatly affects the deposition and behavior of chemicals, including pesticides, growth regulators, and foliar nutrients sprayed on plants, it would be desirable to control the lipid content of cuticles in order to optimize such content for desirable plant variants. It also would be desirable to affect the lipid content of a plant's seeds or to synthesize various plant lipids by in vitro means.

Accordingly, it is an object of the present invention to provide new materials and methods that will allow one to create plant varieties having novel environmental and disease resistances. It is a further object of the present invention to provide new plants having novel environmental and disease resistance and/or plants producing seeds having high levels of saturated or unsaturated long-chain fatty acids and lipids. It is also an object of the present invention to provide plants able to synthesize such fatty acids and lipids of variable and defined chain lengths as well as to provide methods for generating such plants. It is yet a further object of the present invention to provide the isolated genes and gene products responsible for lipid biosynthesis in plants, for in vivo and in vitro synthesis of plant lipids.

These and other objects and advantages of the present invention, as well as additional inventive features, will be apparent from the description of the invention provided herein.

BRIEF SUMMARY OF THE INVENTION

New materials and methods are disclosed herein for the generation of new plant tissue varieties having novel environmental and disease resistances. Such new materials include cloned cuticular lipid genes, which are useful not only for the generation of new plant varieties that can synthesize different quantities or kinds of plant lipids, combinations thereof, but also for the generation of cuticular lipid gene product for in vitro synthesis of plant lipids.

In particular, the present invention provides certain enriched or isolated nucleic acids comprising, respectively, a nucleotide sequence that encodes a cuticular lipid gene product of a plant, as well as vectors that incorporate such sequences. The present invention further provides an enriched or isolated polypeptide comprising an amino acid sequence encoded by one of the aforementioned nucleic acids. In accordance with the present invention, organisms, seeds, and plant cells that include one of the aforementioned vectors are disclosed as well.

The present invention further provides a method for the establishment of a lipid biosynthesis variety of a plant, comprising the steps of:

(a) constructing a nucleic acid comprising a nucleotide sequence that encodes a cuticular lipid gene product;

(b) inserting the nucleic acid into plant cells; and (c) culturing the cells.

DESCRIPTION OF THE PREFERRED EMBODIMENTS

Figure 1:
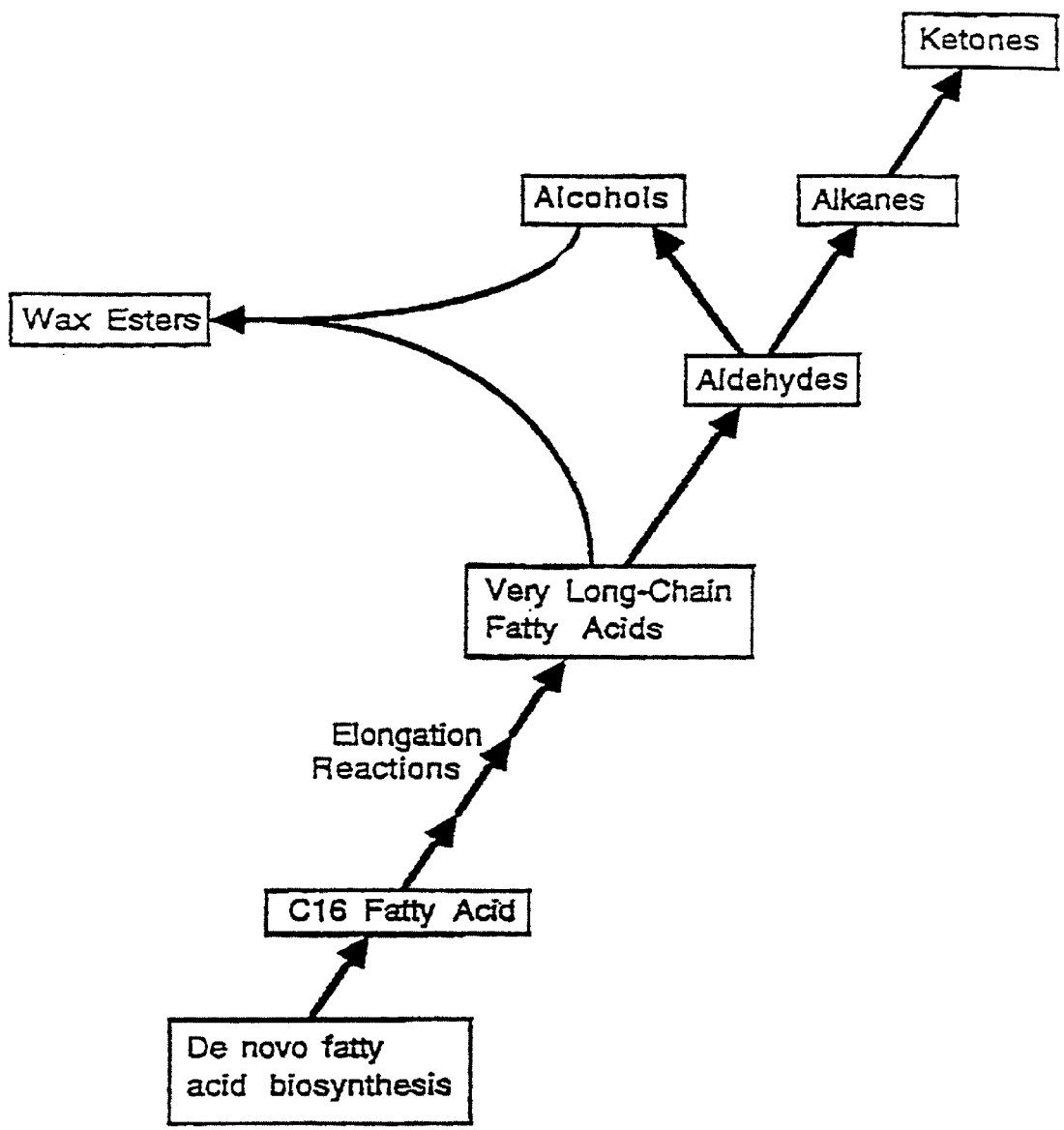
FIG. 1 is a diagram that presents a hypothesized general scheme of lipid biosynthesis in plants.

The present invention provides certain genetic sequences relating to lipid biosynthesis in plants, and further provides methods for the use of such sequences for the generation of new varieties of plants having improved resistance to disease and/or certain environmental conditions, or altered lipid content in seeds, for example. The genetic sequences disclosed herein encode at least a portion of individual genes that encode gene products that directly participate in the biosynthesis of cuticular lipid products. Such genes encode enzymes included in lipid biosynthetic pathways, for example. The present invention does not include genes that have indirect or incidental effects on the plant cuticular lipids, as in the case of glossy15 of maize, discussed hereinabove. The precise function of any of the identified genes may or may not be known, and is immaterial to the use of such genes as contemplated in the present invention. For example, one can use one of the identified genes, or portions thereof, for the purpose of altering the cuticular lipid component of a plant or of a portion of a plant by the insertion of said gene or genes into a plant using suitable means followed by screening the progeny of such a plant for variants or mutants that have the desired altered cuticular lipid component, again using suitable, conventionally available means. Such variants or mutants may incorporate new or altered or nullified gene functions as a result of methods disclosed herein.

The availability of reverse genetics systems, which are well-known in the art, makes the generation and isolation of down-regulated or null mutants feasible, given the availability of a defined nucleic acid sequence, as provided herein. One such system (the Trait Utility System for Corn, i.e., TUSC) is based on successful systems from other organisms (Ballinger et al., *Proc. Natl. Acad. Sci. USA*, 86, 9402–9406 (1989); Kaiser et al. (1990), *Proc. Natl. Acad. Sci. USA*, 87, 1686–1690; and Rushforth et al., *Mol. Cell. Biol.*, 13, 902–910 (1993)). The central feature of the system is to identify Mu transposon insertions within a DNA sequence of interest in anticipation that at least some of these insertion alleles will be mutants. To develop the system, DNA was collected from a large population of Mutator transposon stocks that were then self-pollinated to produced F2 seed. To find Mu transposon insertions within a specific DNA sequence, the collection of DNA samples is screened via PCR using a gene-specific primer and a primer that anneals to the inverted repeats of Mu transposons. A PCR product is expected only when the template DNA comes from a plant that contains a Mu transposon insertion within the target gene. Once such a DNA sample is identified, F2 seed from the corresponding plant is screened for a transposon insertion allele. Transposon insertion mutations of the an1 gene have been obtained via the TUSC procedure (Bensen et al. (1995)). This system is applicable to other plant species, at times modified in accordance with knowledge and skills reasonably attributed to ordinary artisans.

In addition, in accordance with the present invention, long-chain fatty acids (LCFA's) and very long-chain fatty acids (VLCFA's), such as are currently obtained from the jojoba plant and sperm whale oil, may be produced. Both in vitro approaches and in vivo approaches are recited herein. For example, the various enzymes required for the appropriate lipid synthesis can be prepared from strains of host organisms, such as *E. coli* or *S. cerevisiae*, each strain of which includes the genetic information that encodes each enzyme needed for a suitable lipid biosynthetic pathway. Combining a suitable combination of such lipid biosynthetic enzymes in a reaction vessel with suitable substrates, energy source, co-factors and other ingredients known in the art will result in the in vitro production of LCFA's and VLCFA's. Alternatively, organisms can be transformed or transfected with suitable genetic material such that the quantity and/or quality of LCFA's or LVCFA's that are synthesized in vivo are altered to produce LCFA's and LVCFA's of a quantity and a quality that is desired. For example, such genetic engineering manipulation of an oil-producing plant will result in a plant or tissue culture that will produce LCFA's and/or VLCFA's of a superior sort and/or quantity, relative to what is produced by naturally-occurring oil-producing plants. By oil-producing plants, it is intended that maize, soybean, rapeseed, canola, cotton, safflower, peanut, palm, sunflower and the like are included.

In particular, the present invention provides an enriched or isolated nucleic acid, wherein the nucleic acid hybridizes under at least moderately stringent hybridization conditions to a second nucleic acid that includes a polynucleotide that encodes a cuticular lipid gene product of a plant. A cuticular gene product may be a polypeptide or an RNA molecule, and is preferably a polypeptide. The cuticular lipid gene product is involved in cuticular lipid biosynthesis, such as a biosynthetic enzyme for lipids, wherein precursor substrates are caused to react suitably to form LCFA's and VLCFA's or precursors thereof. Genes in maize that effect changes in the cuticular lipids have been named "glossy," in consequence of the appearance that typical mutations at a cuticular lipid gene in maize causes. See Schnable et al., *Current Topics in Plant Physiology*, 9, 196–206 (1993). Similar effects have been noted in Arabidopsis, wherein cuticular lipid gene mutants have been named "Cer," which is short for Ecerferum. As noted above, all plants have cuticular lipid genes, the isolation of which are enabled by the methods of the present invention. As illustrated hereinbelow, cloned polynucleotides that encode maize glossy gene products may be used to identify and isolate related or homologous polynucleotides in maize and other genomes.

The term "nucleic acid" refers to a polymer of DNA or RNA, i.e., a polynucleotide, which can be single- or double-stranded, and can optionally contain synthetic, nonnatural, or altered nucleotides. Any combination of such nucleotides can be incorporated into DNA or RNA polymers. The nucleic acid is "enriched" in that the concentration of the material is at least about 2, 5, 10, 100, or 1,000 times its natural concentration, for example, advantageously 0.01% by weight, preferably at least about 0.1% by weight. Enriched preparations of about 0.5%, 1%, 5%, 10%, and 20% by weight are also contemplated. A polynucleotide is "isolated" in that the material has been removed from its original environment, e.g., the genome of a plant, presuming that it is naturally occurring. It is also advantageous that the nucleic acids be in purified form, wherein "purified" does not mean absolute purity but rather relative purity, wherein, for example, the nucleic acids of the present invention are isolated in a laboratory vessel in a mixture of other nucleic acids, such as portions of a vector or other molecules associated with genetic engineering.

Preferably, the enriched or isolated nucleic acid of the present invention hybridizes under at least moderately stringent hybridization conditions to a second nucleic acid that includes nucleotide sequences specific to a gene selected from the group consisting of glossy1, glossy2, glossy3, glossy4, glossy6, glossy8, glossy11, glossy19, glossy25, glossy26, and cer2, or substantial portions thereof; more preferred, the nucleic acid hybridizes under the aforementioned conditions to a second nucleic acid that includes nucleotide sequences specific to a gene selected from the group consisting of glossy1, glossy2, glossy8, glossy25, glossy26, and cer2, or substantial portions thereof; yet more preferred the selected nucleotide sequence are specific to the glossy1, glossy2, glossy8, or cer2 genes; most preferred, the selected nucleotide sequences are specific to glossy1 or glossy8. Another preferred embodiment of the present invention relates to the enriched or isolated nucleic acid that hybridizes under stringent hybridization conditions to a second nucleic acid, as listed above.

Stringency of hybridization is a term of art that refers to the conditions used for a hybridization reaction, whereby complementary single strands of nucleic acid join to one another to form double-stranded nucleic acid with some degree of mismatch, the degree of which is a function of the stringency used. In particular, the stringency will depend upon the size and composition of the strands of nucleic acid that are caused to react, the degree of mismatching allowed, the desired cross reactivity, and the like. The degree of stringency can be affected by the ionic conditions employed and temperature, among others, as is well known in the art. Sambrook et al., *Molecular Cloning: A Laboratory Manual* (2d ed., 1989).

As used in the context of the present invention, the specified stringency of hybridization in part define the inventive nucleic acid. Accordingly, the hybridization conditions are designed suitably to be at least moderately stringent or stringent. In the former case, suitable conditions of salt, temperature, reaction mixture, and size of nucleic acid reactants are set in accordance with conventional knowledge to provide from about 45% to about 70% mismatch of the sequence of nucleotides of the nucleic acid. Preferably, moderately stringent hybridization conditions are set to provide from about 55% to about 75% mismatch; and more preferably, such conditions are set to provide from about 60% to about 70% mismatch. In the latter case, suitable conditions for hybridization are set in accordance with conventional knowledge to provide from about 10% to about 40% mismatch. Preferably, stringent hybridization conditions are set to provide from about 20% to about 40% mismatch; and more preferably, such conditions are set to provide from about 30% to about 40% mismatch. By mismatch, it is meant the degree to which non-complementary base pairs are found opposite one another in otherwise duplex nucleic acid, thereby forming bubble structures and causing the melting temperature of the duplex to be lower as compared to a 100% matched duplex of the same length and base composition.

Seventeen loci of the glossy (gl) genes of maize have been described in the technical literature (for example, see Bianchi et al., *Maydica*, 30, 179 (1985)), and have been further elucidated by work disclosed herein. In addition, the present invention provides two more glossy loci, namely glossy25 and glossy26, which, since filing of the parent application, have been disclosed by Schnable et al., Maydica, 39, 279–287 (1994). The glossy loci affect the quantity and/or composition of cuticular lipids on seedling leaves, and, perhaps, elsewhere on the plant cuticle. The names of the known loci are glossy1, glossy2, glossy3, glossy4, glossy5, glossy6, glossy8, glossy9, glossy11, glossy14, glossy15, glossy17, glossy18, glossy19, glossy2o, glossy21, glossy22, glossy25, and glossy26; albeit, as noted above, glossy15 apparently encodes a developmental control mechanism that provides indirect or incidental effects upon the plant cuticle, and, thus, is not included as a cuticular lipid gene as that term is used in the context of the present invention. In contrast, the other glossy genes apparently encode gene products that have direct effects upon the plant cuticle, such as would be the effect of a gene in a lipid biosynthetic pathway. Mutant seedlings are usually identified because applied water forms droplets on their leaf surfaces and a "glossy" appearance is obtained thereby.

Four of the 19 glossy loci are members of duplicate gene pairs (namely, glossy5 and glossy20, and glossy21 and glossy22). Accordingly, a seedling must be homozygous mutant for both members of such pairs before it expresses a mutant phenotype. The existence of the duplicate gene pairs suggests that the glossy genes, or a subset thereof, may represent a gene family, wherein the members are related to an ancestral locus that duplicated, diverged in sequence, followed by succeeding rounds of gene duplication and sequence divergence over evolutionary time. The importance of this observation and hypothesis is that the identification of one nucleic acid sequence specific to one of the glossy genes, which is disclosed should provide probes therefrom for the identification and isolation of other so-related glossy genes.

The present invention is also directed to a nucleic acid as described hereinabove that is flanked by regulatory sequences. Preferably, such regulatory sequences are specific to plants, fungi, and bacteria. More preferably, such regulatory sequences are specific to a plant or plants, such as one of the aforementioned oil-producing plants. As noted above, the present invention provides, inter alia, plant varieties that differ from wildtype by the inclusion of nucleic acids in accordance with the present invention. In this context, regulatory sequences of nucleic acid that direct the activity of a particular gene to occur at a point in or period of the development of the plant and/or direct the accumulation of LCFA's or VLCFA's in a particular structure of the plant, such as the seed or fruit, may be affixed upstream or downstream of the cuticular lipid gene of interest. Such regulatory DNA sequences are known to those of ordinary skill in the art.

The nucleic acid of the present invention can be isolated from any plant. As noted in the Background section above, all plants have lipids in their respective cuticles, which lipids are synthesized de novo as fatty acids in the plastids of the plant's cells, after which the fatty acids are transported to the cytosol, where chain elongation reactions are mediated by the cuticular lipid gene products disclosed herein, and, perhaps, other enzymes generically referred to as elongases, acylases, and the like. Both monocotyledons and dicotyledons may be sources of such nucleic acids as provided by the present invention.

Preferred nucleic acids of the present invention are isolated from any suitable oil-producing plant. Such plants are either monocotyledonous or dicotyledonous, including maize, soybean, rapeseed, canola, cotton, safflower, peanut, palm, and sunflower. The more preferred plants from which the cuticular lipid genes are derived are maize or canola.

The present invention also provides an enriched or isolated polynucleotide, wherein the polynucleotide hybridizes under at least moderately stringent hybridization conditions to a second polynucleotide selected from the group consisting of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21, and polynucleotides complementary thereto. A preferred nucleic acid according to the present invention hybridizes to the same set of second polynucleotides only under stringent hybridization conditions. A more preferred enriched or isolated nucleic acid of the present invention comprises a polynucleotide selected from the group of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21, and polynucleotides complementary thereto, and polynucleotides substantially equivalent thereto. The polynucleotides identified by sequence identification number are fully described in the Examples below.

A "substantially equivalent" polynucleotide is a polynucleotide that varies from the identified polynucleotide by one or more substitutions, deletions, or additions, the effect of which does not result in an undesirable functional dissimilarity between the two polynucleotides. In other words, the polypeptide that results from the substantially equivalent polynucleotide has the activity characteristic of, for example, the glossy8 gene product, when considering polynucleotides that are substantially equivalent. A difference in sequence at the amino acid level will be understood to include amino acid differences, which range from a single amino acid substitution, deletion, or insertion to a number of amino acid substitutions, deletions, and/or insertions, wherein the resulting polypeptide is still recognizable as related to the glossy8 protein as well as those amino acid sequence differences, which result in a larger polypeptide, such as a precursor protein, a complete mature protein, and a truncated protein.

The enriched or isolated nucleic acid which comprises the nucleotide sequence selected from the group consisting of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21 is most preferred. The present inventive nucleic acid may be identified for enrichment or isolation by hybridization to any subfragment of a polynucleotide of the aforementioned set of polynucleotides of at least 20 nucleotides under stringent hybridization conditions as described in Sambrook et al., *Molecular Cloning: A Laboratory Manual* (2d ed., 1989). Accordingly, this invention preferably encompasses the entire sequence of the glossy8, glossy1, glossy2, or CER2 gene and fragments thereof, which have been generated by any suitable technique, such as by restriction enzyme digestion of chromosomal or plasmid DNA, or by synthesis, and which may be either DNA or RNA.

In addition to the methods recited in Example 1 for the identification and isolation of cuticular lipid genes and related nucleic acids of the present invention, other methods may be used alternatively, such as, inter alia, chromosome walking and heterologous probe selection.

Chromosome walking, which is described in Example 6, is a particularly useful technology that can facilitate the molecular isolation of any mapped gene (Bender et al., *J. Mol. Biol.*, 168, 17–338 (1983)) and has been found to be particularly useful with plants that have a relatively small genome size, such as that of Arabidopsis. Meyerowitz, in *Methods in Arabidopsis Research*, pp. 100–118 (Koncz et al., eds., World Scientific, Singapore, 1992). In addition, five YAC libraries, representing 28 genome equivalents, exist for this species. Gibson et al., in *Methods in Arabidopsis Research* (C. Koncz et al., eds., River Edge N.J., World Scientific, 1992), pp. 119–143. Several Arabidopsis genes have been cloned via this strategy (Yanofsky et al., *Nature*, 346, 35–39 (1990); Giraudat et al., *Plant Cell*, 4, 1251–1261 (1992); and Arondel et al., *Science*, 258, 1353–1354 (1992)). This technique is useful, of course, in species of larger genome size as well, such as maize.

A chromosome walk is initiated by identifying from a library of large DNA fragments the specific fragment(s) that contain sequences homologous to a restriction fragment length polymorphism (RFLP) marker that is closely linked to the target gene. Typically, the library of DNA fragments is maintained as yeast artificial chromosomes, i.e., YACs (Burke et al., *Science*, 236, 806–811 (1987)), although cosmids, P1 phage or λ phage have been used. Single copy sequences from the termini of YACs that contain sequences homologous to a starting RFLP are then used as hybridization probes to isolate overlapping DNA fragments. This process is repeated until the entire chromosomal region, from the starting RFLP marker to beyond the target gene, has been cloned as a contiguous segment (a "contig"). Typically, the contig is oriented by mapping DNA sequences from the growing contig to the genetic/RFLP map. Similarly, the endpoint of the walk is established by demonstrating that the contig contains DNA sequences from both sides of the target gene. For both of these operations, DNA sequences from the contig must be genetically mapped. The efficiency of this mapping can be greatly increased by selecting a population of plants that have a high probability of carrying recombination breakpoints in the region defined by the contig. Such a mapping population is established by selecting plants that carry a recombination breakpoint between two visible genetic markers that flank the interval to be walked. The precision of the mapping increases proportionally with the number of genetic recombinants. The greater the precision of this mapping, the smaller the uncertainty associated with the positioning of the target gene on the contig. Once the target gene has been localized in the contig to as small an interval as the mapping population permits, the target gene is identified from the interval via its ability to complement genetically the mutant phenotype. The ability of a sequence to complement the mutant phenotype is assayed by transforming plants homozygous for a mutant allele of the target gene. Alternatively, comparisons between wildtype and mutant sequences can also identify the target gene from the interval.

Other technologies for gene isolation in Arabidopsis and other plants include genomic subtraction, and transposon and T-DNA tagging. Genomic subtraction requires the availability of strains having deletions of the target gene (Strauss and Ausubel, *Proc. Natl. Acad. Sci. USA*, 87, 1889–1893 (1990); and Sun et al., *Plant Cell*, 4, 119–128 (1992)); however, such deletions are not available for CER2, for example. A transposon tagging system in Arabidopsis has recently become available. The success in tagging and cloning a petunia gene using a heterologous maize transposon (Chuck et al., *Plant Cell*, 5, 371–378 (1993)) provided the direction to extend this technique to Arabidopsis, and further supports the view that this technique is amenable to tagging virtually any plant with heterologous (Dean et al., *Plant J.*, 2, 69–81 (1992); Grevelding et al., *Proc. Natl. Acad. Sci. USA*, 89, 6085–6089 (1992); Swinburne et al., *Plant Cell*, 4, 583–595 (1992); and Fedoroff and Smith, *Plant J.*, 3, 273–289 (1993)) and/or endogenous (Tsay et al., *Science*, 260, 342–344 (1993)) transposons. T-DNA tagging, another method to locate a gene, has been realized (Feldmann, *Plant J.*, 1, 71–82 (1991)) and is in wide use (e.g., Feldmann et al., *Science*, 243, 1351–1354 (1989); Herman et al., *Plant Cell*, 11, 1051–1055 (1989); Konz et al., *EMBO J.*, 9, 1337–1346 (1989); and Kieber et al., *Cell*, 72, 427–441 (1993)). Additionally, having isolated at least one cuticular lipid gene, the nucleic acid thereof can be used whole or in part (by sub-cloning fragments thereof) as a probe in heterologous systems, as exemplified in Example 4 hereof. Preferably, such a technique requires that the stringency of the selective hybridization procedure be lowered, and then slowly raised, as is well known in the art.

Although T-DNA tagging, chromosome walking or heterologous probe selection can identify a DNA fragment that putatively contains the gene of interest, in each instance these DNA fragments must be confirmed by genetic complementation or some other means, which is fully disclosed in Examples 1 and 7. Although the methods of identification of a particular gene sequence has been described herein largely with reference to maize and Arabidopsis only, it is abundantly clear to one of ordinary skill that such methods may be adapted for gene identification in other species, particularly in the context of the present invention. Moreover, having identified and isolated particular cuticular lipid genes from maize and Arabidopsis, counterpart or homologous genes in other species may be identified and isolated using the sequences disclosed herein as probes, using suitable conventional means as, for example, illustrated in Example 5. Accordingly, the identification of the cuticular lipid genes, and cloning and using thereof, is enabled hereby for any of the aforementioned oil-producing plants, as well as other plants that have lipid components in their cuticle.

The nucleic acids of the present invention may be cloned in any suitable vector and the vector as constructed with nucleic acid insert of the present invention is used to transform or transfect any suitable host. *E. coli*, in particular *E. coli* DH5α, SA2821 or Y1090 is a preferred host. Suitable vectors include those designed for propagation and expansion or for expression or both. Constructs of vectors can be prepared, either circular or linear, to contain the entire cuticular lipid gene nucleotide sequence or a portion thereof ligated to a replication system functional in a microorganism host, whether prokaryotic or eukaryotic. Suitable hosts include *E. coli*, *B. subtilis*, *P. aerugenosa*, *S. cerevisiae*, and *N. crassa*. Replication systems may be derived from ColE1, 2 mμ plasmid, λ, SV40, bovine papilloma virus, or the like. In addition to the replication system and the inserted DNA, the construct usually will include one or more markers, which allow for selection of transformed or transfected hosts. Markers may include biocide resistance, e.g., resistance to antibiotics, heavy metals, etc., complementation in an auxotrophic host to provide prototrophy, and the like. A preferred cloning vector is selected from the group consisting of pUC18, pET11d, EMBL4, NM1149, and pLZO3.

More preferably, the present invention provides expression vectors for the expression of such polypeptides. A preferred expression vector is one that comprises a nucleic acid comprising, as an insert, a nucleotide sequence that encodes a cuticular lipid gene product, preferably that of one of the aforementioned oil-producing plants. A more preferred expression vector comprises a nucleic acid comprising a nucleotide sequence selected from the group consisting of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21, a sequence complementary thereto, or a substantially equivalent sequence. The most preferred expression vector comprises a nucleic acid comprising a nucleotide sequence selected from the group consisting of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21 and a vector as described above.

One skilled in the art will appreciate that any one of a number of expression vectors may be utilized in the context of the present invention with some degree of success, including, but not limited to, the following: pGEX2T, pATH11, pNH8A (Strategene, Inc., La Jolla, Calif.), pGL2 (Promega, Madison, Wis.), pEX2 (Boehringer Mannheim Biochemicals, Indianapolis, Ind.), and pMOSELlox (Amersham Corporation, Arlington Heights, Ill.).

Care should be taken to choose a vector that does not result in cytotoxic expression of the amino acid sequence encoded in the insert of the vector. For expression in microorganisms, the expression vector may differ from the cloning vector in having transcriptional and translational initiation and termination regulatory signal sequences and may or may not include a replication system that is functional in the expression host. The coding sequence is inserted between the initiation and termination regulatory signals so as to be under their regulatory control. Expression vectors may also include the use of regulatable promoters, e.g., temperature-sensitive or inducible by chemicals, or genes that allow for integration and amplification of the vector and insert DNA, such as tk, dhfr, metallothionein, and the like. Such controls, if incorporated into a plant, could allow for drought resistance, for example, by promoting expression of drought resistant cuticular lipids upon the advent of a triggering level of heat. Other environmental resistant varieties may promote expansion in response to water stress or UV stress, for further examples.

The vector can be used to express a dsDNA sequence, either isolated and cloned or synthesized, to obtain a precursor protein, which is subject to further manipulation by cleavage, a complete mature protein, or a fragment thereof by introducing the expression vector into an appropriate host, where the regulatory signals are functional in the host. The expression host is grown in an appropriate nutrient medium, whereby the desired polypeptide is produced and isolated from cells or from the medium, when the polypeptide is secreted. Where a host is employed in which the vector's transcriptional and translational regulatory signals are functional, then the cuticular lipid gene DNA sequence may be manipulated to provide for the expression of the desired polypeptide in proper juxtaposition to the regulatory signals. The polypeptide products can be obtained in substantially pure form, particularly free of cellular debris, which may include such contaminants as, for example, proteins, polysaccharides, lipids, nucleic acids, viruses, bacteria, fungi, and combinations thereof, using methods well known in the art.

The nucleic acids described above may be used in a wide variety of ways, depending upon their size, their natural function, the use for which they are desired, and the degree to which they can be manipulated to modify their function. For example, nucleic acids of at least about 20 bases, more usually at least 50 bases, and usually not exceeding about 1,000 bases, more usually not exceeding about 5,000 bases, may serve as probes for the detection of the presence of a cuticular lipid gene or homologous nucleic acids in an organism. Such detection can provide information relating to whether manipulation of the plant with a particular cuticular lipid gene could provide an opportunity to generate new, resistant varieties of the plant, and provide novel sources of various oils.

The method of detection involves duplex formation by annealing or hybridization of the oligonucleotide probe, either labeled or unlabeled, depending upon the nature of the detection system, with the DNA or RNA of an organism believed to produce the particular cuticular lipid gene. Usually this method of detection involves cell lysis, extraction of nucleic acids with organic solvents, precipitation of nucleic acids in an appropriately buffered medium, and isolation of the DNA or RNA. The DNA may be fragmented by mechanical shearing or restriction endonuclease digestion. The nucleic acid may then be bound to a support or may be used in solution depending upon the nature of the protocol. The Southern technique (Southern, *J. Mol. Biol.*, 98, 503 (1975)) may be employed with denatured DNA by binding the single-stranded fragments, for example, to a nitrocellulose or nylon filter. RNA also may be blotted onto a filter (Thomas, *Proc. Natl. Acad. Sci. USA*, 77, 5201 (1980)). Preferably, the fragments are subjected to electrophoresis prior to binding to a support so as to enable the selection of variously sized fractions. Alternatively, the assay may be accomplished on plant cells fixed to a substrate and permeabilized using methods known in the art, whereupon the hybridization procedure can be conducted to determine if a homologous gene to a particular cuticular lipid gene exists in the plant of interest, and/or if that plant is expressing RNA that is homologous to the cuticular lipid gene.

The oligonucleotide probes may be DNA or RNA, albeit usually they are DNA. The oligonucleotide sequence may be prepared synthetically or by cloning. Suitable cloning vectors are well-known to those skilled in the art. The oligonucleotide probe may be labeled or unlabeled. A wide variety of techniques exist for labeling DNA and RNA and include radiolabeling by nick translation, tailing with terminal deoxytransferase, or the like, where the bases employed are labeled, for example, with radioactive $^{32}P$. Other labels, that may be used include fluorophores, enzymes, enzyme substrates, enzyme cofactors, enzyme inhibitors, and the like. Alternatively, instead of using a label, which provides a detectable signal by itself or in conjunction with other reactive agents, ligands can be used to which receptors bind, where the receptors are labeled, such as with the above-indicated labels, to provide detectable signals by themselves or in conjunction with other reagents (see, e.g., Leary et al., *Proc. Natl. Acad. Sci. USA*, 80, 4045–4049 (1983)). The oligonucleotide probes are hybridized with the denatured nucleic acid, substantially intact or fragmented, or fractions thereof, under conditions of predetermined stringency, the practicalities of which have been discussed hereinabove.

The present invention also provides an enriched or isolated polypeptide comprising an amino acid sequence of a cuticular lipid gene product from a plant, one example of which comprises the polypeptide encoded by the glossy8 gene of maize. Other such polypeptides disclosed in the context of the present invention include SEQ ID NO:4, SEQ ID NO:7, SEQ ID NO:9, SEQ ID NO:12, SEQ ID NO:14, SEQ ID NO:16, SEQ ID NO:18, SEQ ID NO:22, and SEQ ID NO:23. Preferably, the enriched or isolated polypeptide comprises an amino acid sequence encoded by a nucleic acid that comprises the structural coding portion of a nucleotide sequence, such as one selected from the group consisting of SEQ ID NO:1, SEQ ID NO:2, SEQ ID NO:3, SEQ ID NO:5, SEQ ID NO:6, SEQ ID NO:8, SEQ ID NO:10, SEQ ID NO:11, SEQ ID NO:13, SEQ ID NO:15, SEQ ID NO:17, SEQ ID NO:19, SEQ ID NO:20, and SEQ ID NO:21, polynucleotides complementary thereto, or polynucleotides substantially equivalent thereto. More preferably, the enriched or isolated polypeptide comprises the polypeptide selected from the group consisting of SEQ ID NO:4, SEQ ID NO:7, SEQ ID NO:9, SEQ ID NO:12, SEQ ID NO:14, SEQ ID NO:16, SEQ ID NO:18, SEQ ID NO:22, and SEQ ID NO:23.

The enriched or isolated polypeptide is "enriched" in that the concentration of the material is at least about 10, 100, 1,000 or 10,000 times its natural concentration, for example, advantageously 0.1% by weight, preferably at least about 1% by weight. Enriched preparations of about 5%, 10%, 20%, 50% and 75% or more by weight are also contemplated. A polypeptide is "isolated" in that the material has been removed from its original environment, e.g., the cytoplasm or endoplasmic reticulum of a plant cell or microbial host cell, such as *E. coli* or *S. cerevisiae*. It is also advantageous that the polypeptides of the present invention be in purified form, wherein "purified" does not mean absolute purity but rather relative purity, which is defined herein as in excess of 80% pure by weight. Such polypeptides can be combined to catalyze reactions required in the biosynthesis of valuable LCFA's and VLCFA's, as discussed herein above, using methods known in the art.

The polypeptides of the present invention are encoded by the cuticular lipid genes of a plant. Plants used in the context of the present invention that provide the genes of interest and the polypeptides encoded therein may be any suitable plant, and is preferably an oil-producing plant, as delineated hereinabove.

Most preferred polypeptides of the present invention are those that are encoded by an enriched or isolated nucleic acid comprising a polynucleotide selected from the group consisting SEQ ID NO:1, SEQ ID NO:2, SEQ ID NO:3, SEQ ID NO:5, SEQ ID NO:6, SEQ ID NO:8, SEQ ID NO:13, SEQ ID NO:15, SEQ ID NO:17, SEQ ID NO:19, SEQ ID NO:20, and SEQ ID NO:21, a polynucleotide complementary thereto, and a polynucleotide substantially equivalent thereto, as understood by the earlier discussion regarding the nucleic acids of the present invention.

In accordance with another aspect of the present invention, the nucleic acids disclosed herein are used in a method for the establishment of a lipid biosynthesis variety of a plant cell or of a plant, comprising the steps of: (a) constructing a sense nucleic acid or an anti-sense nucleic acid specific for a cuticular lipid gene product or a portion of the cuticular lipid gene product; (b) inserting the nucleic acid into plant cells; and (c) culturing the cells. Additionally, the inventive method further comprises the (d) culturing of the cells to provide the plant, which plant can then produce seeds. Such seeds may or may not be fertile. Accordingly, the inventive method involves plant tissue culture techniques known in the art, and may involve standard genetic and reverse genetic approaches to the generation and identification of variants or mutants having new, altered, or nullified gene functions with respect to specific genes.

Insertion of nucleic acids into plant cells is accomplished by any suitable means, including cell bombardment, i.e., attaching the DNA to metallic pellets and blasting them through the plant's cell wall (Fromm et al., *Bio/Technology*, 8, 833–839 (1990); and Gordon-Kamm et al., *Plant Cell*, 2, 603–618 (1990)), and, for the introduction of exogenous DNA to a dicotyledonous plant cell, insertion of the nucleic acid of the present invention into the Ti plasmid of Agrobacterium and adding suitable ingredients to promote transformation thereby (Horsch et al., *Science*, 223, 496–498 (1984); and DeBlock et al., *EMBO J.*, 3, 1681–1689 (1984)). Other techniques are available for the introduction of exogenous DNA into a plant and/or a subset of its constituent cells, including electroporation, protoplast-mediated gene transfer, and silicon carbide crystal-mediated gene transfer. These various techniques are discussed in *Genetic Engineering News*, vol. 14, no. 4 (Feb. 15, 1994) pages 1, 3, and 24, and are generally known in the art.

The nucleic acid that is used in the inventive method hybridizes under at least moderately stringent hybridization conditions to a DNA that includes nucleotide sequences specific to a gene selected from the group of maize glossy genes, as disclosed above. Such DNA preferably is flanked with a regulatory sequence, such that a new plant variety, or a cell thereof, derived from the aforementioned procedure, expresses its extra or altered or nullified cuticular lipid genes in a developmentally and/or tissue-specific fashion. That is, lipid genes used in the context of the present invention may be used to add, alter, or remove a gene function that affects at least one cuticular lipid of a treated plant.

The method of the present invention is used to establish a new lipid biosynthesis plant variety of any suitable plant, which new variety is also an embodiment of the present invention. Indeed, the present invention relates to a new plant variety that is generated and isolated by the aforementioned method for the establishment of a lipid biosynthesis variety of a plant, comprising the steps as articulated above. Preferably, such a plant produces oil, such as maize, soybean, rapeseed, canola, cotton, safflower, peanut, palm, and sunflower. Most preferably, the method is used to produce new varieties of maize and canola.

The new varieties that are provided by the inventive method include environmental, disease, and pest resistance varieties. Environmental resistance relates to wind, frost, UV or drought. The connection between the lipid complement of the cuticle and such resistance is substantial, in view of the knowledge in the art that the lipid cuticular component lends strength to the overall plant, serves to prevent undue evaporation of internal liquids, as well as serves to filter UV radiation, thereby preventing undue exposure to environmental UV levels that keep rising.

Disease and insect resistance mediated by the cuticular lipids includes the blocking or retarding of fungal-, viral-, or bacterial-borne disease vectors, the most important of which are the fungal-borne rust diseases. Such disease vectors typically are opportunistic, entering the plant by way of tears or cuts in the cuticle. Obviously, altering the lipid complement of the cuticle so as to increase the strength and toughness of the cuticle necessarily reduces inadvertent tears and cuts, which, in turn, reduce opportunistic infestation by microbial pests. Similarly, strengthening and toughening the cuticle protects the plant against attack by various other pests, including insects, spiders, aphids, and the like.

Disease resistance in accordance with the present invention may also be conferred by the alteration or elimination of certain lipids that are attractive or otherwise stimulate certain microbial pathogens or opportunistic insects. The present invention provides the means for the removal or alteration of such lipid-based chemical signals.

Particularly with regard to microbe or insect pest resistance, a factor in the susceptibility to damage by such pests is the availability of water. Lipid components that foster retention of water droplets on the cuticle surface will tend to invite growth and attention by microbes and insects. Similarly, frost resistance is a function of the retention of as little surface water as possible on the plant. Accordingly, altering the lipid components of any plant provides environmental- and microbe-resistant varieties of plants.

Another aspect of the present invention relates to a method of altering the lipid content of suitable plant structures or tissues, such as seed, fruit and flower. Such an alteration can increase or decrease the normal levels, or change the kind of lipids present in a particular plant structure. Growth of plants or tissue cultures of suitable cuticular lipid gene constitution, therefore, can provide commercial sources of such lipids or combination of lipids.

The present invention also relates to any suitable organism comprising the vector comprising a nucleic acid comprising a nucleotide sequence that encodes a cuticular lipid gene product of a plant. A suitable organism can be any suitable plant, yeast, or bacteria, such as discussed hereinabove regarding suitable plants from which to isolate the cuticular lipid genes and regarding suitable hosts in which to insert the enriched or isolated nucleic acid of the present invention. Preferred organisms are oil-producing plants, as described above, and yeast, such as *S. cerevisiae*. A seed-bearing plant that hosts a vector/nucleic acid construct can bear seeds, which, themselves, include the construct, which seeds also constitute a preferred embodiment of the present invention.

Finally, a plant cell hosting a vector/nucleic acid construct of the present invention constitutes another preferred embodiment. Such cells can be cultured and kept as plant tissue culture cells, or certain plant hormones known in the art may be included in the culture media, thereby causing the plant tissue culture cells to differentiate and thereby form a new plant variety. Such plant culturing methods useful in the performance of this aspect of the invention are well-known in the art. Such a new plant variety may be fertile or infertile.

The following examples further illustrate the present invention, but, of course, should not be construed as in any way limiting its scope.

EXAMPLE 1

This example sets forth methods used in the identification and isolation of glossy genes.

Gene tagging using naturally-occurring transposons, as described by Walbot, *Ann. Rev. Plant Physiol. Plant Mol. Biol.*, 43, 49–82 (1992), was used to identify previously mapped glossy genes. Specifically, glossy1, glossy2, glossy3, glossy4, glossy6, glossy8, and glossy11 were targeted in the following isolation plot cross using the method of Peterson, in Maize Breeding and Genetics (D. B. Walden, ed., John Wiley & Sons, New York, N.Y., 1978), pages 601–631 (the female parent is listed first in all crosses herein):

Mutator Glx/Glx×glx/glx, wherein x is one of 1, 2, 3, 4, 6, 8, or 11. In the absence of mutation, progeny kernels from each cross are heterozygous for the wildtype allele (e.g., glossy1/Glossy1 or glossy8/Glossy8), and should, therefore, yield wildtype seedlings. Only if a gamete from the female (Mutator) parent carries a newly generated mutant allele (e.g., via the insertion of a Mu1 element, signified as glossy1-Mu, for example) will a glossy seedling be obtained (glossy1-Mu/glossy1 or glossy8-Mu/glossy8, for example). Data of number kernels obtained, progeny screened, and mutants identified are provided in the following table.

| gl Locus | Year Crosses Conducted | Total Population Size | Population Screened | # gl Mutants Isolated | Mutation Rate per 100,000 |
|---|---|---|---|---|---|
| gl1 | 1991 | 1,000,000 | 168,000 | 9 | 5 |
| gl2 | 1992 | 192,900 | 192,900 | 12 | 6 |
| gl3 | 1992 | 230,000 | 122,600 | 13 | 11 |
| gl4 | 1992 | 220,000 | 162,434 | 15 | 9 |
| gl6 | 1992 | 300,000 | 107,300 | 3 | 3 |
| gl8 | 1991 | 324,000 | 307,735 | 60 | 19 |
| gl11 | 1993 | 126,794 | 126,794 | 7 | 5.5 |
| Typical Mutator-Induced Mutation Rates | | | | | 1–10 |

For isolation of glossy genes for which no existing mutant allele exists, or which are lethal as homozygotes, a random gene tagging method was used, as described by Schnable et al., *Proceedings, 28th Annual Illinois Corn Breeder's School* (1992), pages 24–45. The first step was to cross a standard transposon stock to a standard wildtype line of maize. Gametes produced by the transposon stock carry newly-generated transposon insertion mutants at random loci. Thus, many of the progeny from this cross will be heterozygous for new mutations, which are uncovered by self-pollinated crosses and observation of the progeny of such S1 families. Over 10,000 Mutator self-crossed progeny were screened for visible mutants, from which 42 independent glossy mutants have been recovered.

To determine the affected locus of recovered random tagged mutants, TB tests and allelism tests were conducted. TB tests locate mutants to chromosome arm by exploiting the fact that BA translocations fail to disjoin during the second meiotic division during microsporogenesis, according to Birchler, in *Maize for Biological Research* (W. F. Sheridan, ed., Plant Mol. Biol. Assoc., Charlottesville, N.C., 1982), pages 75–78. Allelism tests can be performed by crossing plants homozygous for the Mu1-tagged allele by separate tester lines, each of which is homozygous recessive for one of the existing standard loci. If the tagged allele is allelic to a given standard allele, all seedlings from that cross (and only that cross) will be glossy. Seedlings from all other crosses will have a wildtype phenotype. These tests have established that 23 of the 49 glossy mutants identified in the random tagging process are allelic to previously defined glossy mutants. This collection consists of 6 alleles of glossy1, 1 of glossy2, 1 of glossy3, 3 of glossy4, 13 of glossy8, 2 of glossy11, and 1 of glossy19. In addition, two of the 42 glossy mutants are not allelic to known mutants or to each other; these mutants define previously unknown genes, glossy25, and glossy26. The allelism status of 13 of the glossy mutants is still under analysis.

Using standard maize breeding techniques to analyze over 100 Mutator-induced glossy mutants, it was established that the tagged mutant glossy alleles were heritable. Cloning the various glossy-related genes, both wildtype and mutant forms thereof, was predicated on the availability of the transposon element, itself, as a molecular probe, as disclosed by Chandler and Hardeman, *Adv. Genet.*, 30, 77–122 (1993). Mu1, one of the nine classes of Mu elements, is known to be responsible for the vast majority of mutations recovered from Mutator lines (Brown et al., *Genetics*, 122, 439–445 (1989)); therefore, a Mu1 sequence was used to probe for glossy genes. Mu8 was also used.

Because the Mu elements are typically present in 10–50 copies in the genomes of plants carrying an active Mutator system, a serial outcrossing program was undertaken to reduce the number of Mu elements in the glossy mutant lines. The glossy-Mu lines were crossed to lines that either lack or have low copy numbers of Mu elements in their genomes. Genomic DNA from the resulting progeny plants derived from Mutator parents was prepared and digested with HindIII, which does not cut within the Mu1 element. Southern genomic analyses of these DNAs were conducted according to Stinard et al., *Plant Cell*, 5, 1555–1566 (1993). Internal sequences from Mu1 were used as a probe to identify the plants having the lowest Mu1 copy numbers. These low-copy number plants were then backcrossed to the recurrent parent that either lacks Mu1 elements or has a low copy number. After three to four generations, this procedure provided lines that each carry a glossy allele and only 15–20 copies of the Mu1 element.

The next step was to utilize the low Mu copy number lines in co-segregation analyses to identify the individual Mu element inserted at the glossy locus. First, sibling plants derived from the cross of gl-Mu/Gl with gl-ref/gl-ref, with and without the glossy-Mu allele (glossy and wildtype seedlings, respectively), were obtained. DNA from each individual was digested with a restriction enzyme that does not cut within the Mu element, such as HindIII. Mu specific sequences were used to probe genomic Southern blots of these DNAs in an effort to identify a Mu-containing band that co-segregates with the glossy-Mu allele, i.e., present in all glossy seedlings, but absent in wildtype siblings.

For example, the Mu1 element co-segregated with glossy1-5048 in 93 individuals.

Genomic DNA from progeny resulting from the cross glossy1-5048/Gl1×Gl1/Gl1 was prepared and digested with HindIII. Genotypes of progeny from this cross were established via appropriate testcrosses. Southern analyses of these DNAs using a Mu1-specific probe revealed a 12.5 kb Mu1-containing restriction fragment that co-segregates with the glossy1-Mu allele. Accordingly, the identified fragment is present in all plants carrying the glossy1-Mu allele (i.e., glossy1-5048) and absent in all plants that do not carry this allele.

Similarly, a Mu8-containing 8.6 kb HindIII DNA fragment that co-segregates with glossy8-3142 in 88 individuals was identified.

Genomic DNA from progeny resulting from the cross glossy8-3142/Glossy8×Glossy8/Glossy8 was prepared and digested with HindIII. Genotypes of progeny from this cross were established via standard test-crosses. Southern blot analysis, as described above, of these DNA preparations using a Mu8-specific probe revealed an 8.6 kb Mu8-containing restriction fragment that co-segregates with the gl8-Mu allele. As above, the fragment of interest is present in all plants carrying the mutant allele, here glossy8-3142, and absent in all plants that do not carry this allele.

Genomic libraries were constructed for each of the glossy mutant lines that display a co-segregating Mu-hybridizing restriction fragment, identified hereinabove. These libraries were constructed in lambda-based cloning vehicles, such as EMBL4, Charon 33, or NM1149, using the methods of Frischauf et al., *J. Mol. Biol.*, 170, 827–842 (1983), and Murray in *The Bacteriophage Lambda II* (Hedrix, ed., Cold Spring Harbor Laboratory Press, Cold Spring Harbor, N.Y., 1983), pages 395–432. DNA from an identified glossy line was digested with the identified restriction enzyme and size-selected to include the co-segregating, Mu-containing fragment. Once completed, these libraries were screened with a Mu probe and positive clones were identified via the procedure of Benton and Davis, *Science*, 196, 180–182 (1977). Following plaque purification, DNA from positive recombinant phage was isolated according to the method of Yamamoto et al., *Virology*, 40, 734–744 (1970).

Figure 2:
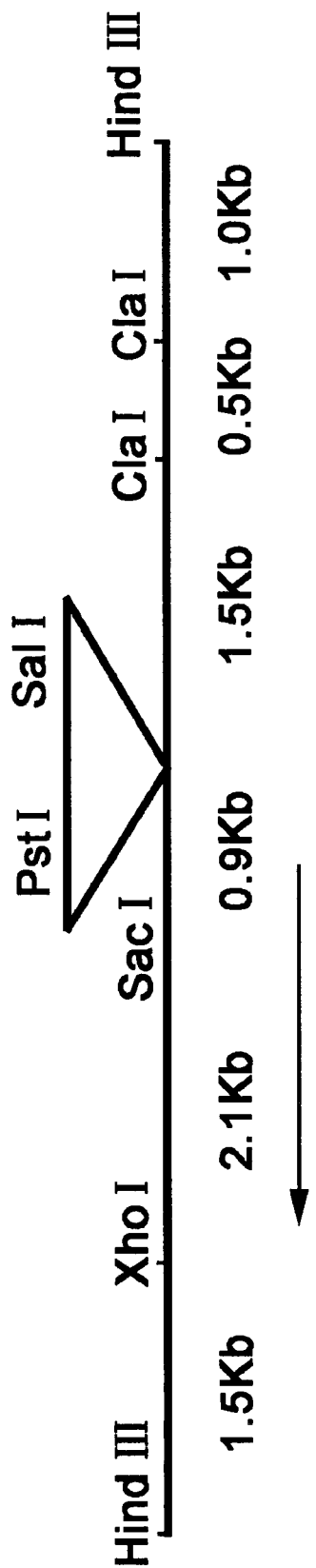
FIG. 2 is a physical map that indicates the relative locations of restriction endonuclease digestion sites for the glossy8-3142 8.6 kb HindIII genomic DNA fragment.

To illustrate, the 8.6 kb HindIII DNA fragment associated with gl8-3142 was cloned by first isolating DNA from an immature unpollinated ear of a maize plant with the genotype gl8-3142/Gl8. This DNA was digested to completion with HindIII, electrophoresed through an agarose gel, and DNA fragments in the size range of 7 to 9 kb were recovered by electro-elution. Size-fractionated DNAs were ligated into the HindIII site of the replacement λ vector Charon 33, packaged using commercial packaging extracts (Stratagene) and plated on *E. coli* strain Y1090. Plaques were lifted on nylon membranes (MSI) and hybridized using a Mu8-specific probe. Hybridizing plaques were picked and purified. Phage DNA was isolated using miniprep DNA purification from two independent isolated positive clones and the 8.6 kb HindIII maize genomic inserts were isolated. Based on restriction enzyme digestion patterns, these two clones are identical. The restriction map based on these analyses is shown in FIG. 2.

The 12.5-kb Mu1-containing DNA fragment associated with the gl1-755048 allele was cloned in the same manner with the following minor modifications. DNA isolated from maize plants carrying the gl1-755048 allele was digested with HindIII, and 12–13 kb fragments were gel-purified and cloned into the λ vector DASHII (Stratagene).

Putative glossy gene DNA sequences were then isolated from the recombinant phage. Because much of the maize genome consists of repetitive sequences, isolation of near-unique DNA sequences that flank the Mu element in positive clones were subjected to "reverse Southerns," according to the techniques of Gupta et al., *EMBO J.*, 3, 133–139 (1984). This procedure requires size fractionating restriction enzyme digested DNA from each clone on an agarose gel, and transferring the DNA, in duplicate, to membranes, as in the procedure of Southern, supra. One of the membranes was probed consecutively with Mu and lambda vector sequences to identify the cloned fragment or fragments that contain the Mu element and those that correspond to the phage vector used to construct the library. The second membrane was probed with labeled total maize genomic DNA to identify repetitive DNA fragments, as unique sequences do not give a signal in this procedure. Fragments that do not give a signal on any of the three hybridizations represent unique or near-unique sequences flanking the Mu element in the maize genome and putatively consist of the glossy locus. These fragments have been subcloned.

To verify the identity of the putative glossy clones, flanking sequences from a putative clone were used as a probe against a series of allelic transposon-induced mutants and their wildtype progenitor alleles. Flanking sequences from a correct clone would be expected to reveal polymorphisms between progenitor wildtype alleles and their corresponding mutant derivatives (as a result of the insertion of a transposon). Exceptional glossy seedlings were isolated from the cross Mutator Glossy8/Glossy8×glossy8-Ref/glossy8-Ref, and had the genotype glossy8-Mu/glossy8-Ref. Sibling wildtype seedlings had the genotype Glossy8/glossy8-Ref. The smaller HindIII-SacI fragment from the putative glossy8 clone (see FIG. 2) hybridized strongly to two bands in HindIII-digested DNA prepared from the glossy and wildtype seedlings. The upper band, which is common to all plants, represents the glossy8-Ref allele. The second (lower) band represents the second allele present in these seedlings (Gl8 in the case of the wildtype seedlings and glossy8-Mu in the glossy seedlings). This second band is larger in plants carrying the glossy8-Mu alleles than in plants carrying their progenitor wildtype Glossy8 allele. These alterations in DNA fragment sizes revealed by the putative glossy8 probe were coincident with mutations at glossy8, thereby demonstrating that the putative glossy8 clone represents the glossy8 gene.

Accordingly, using the procedures above, one can obtain clones of any of the glossy genes of maize and/or confirm the identity of a glossy clone. This procedure may be applied to any organism that has a defined transposon system or is amenable to a heterologous transposon system, and identifiable genetic markers.

EXAMPLE 2

This example sets forth the sequence identified for the insert of a glossy8 cDNA clone, and the method by which the sequence was obtained.

A single copy isolated from the 8.6 kb gl8 genomic clone (i.e., the 3.6 kb HindIII-SacI fragment as shown in FIG. 2) was used to screen a cDNA library according to Sambrook et al., supra. This cDNA library had been prepared with RNA isolated from two-week-old seedlings of the maize inbred line B73. From a total of 800,000 plaques, 13 cDNA clones that could be grouped into three different classes were recovered. These classes of clones have inserts of 1.2 kb, 0.8 kb, and 500 bp in length, respectively. DNA isolated from these clones was double-digested with the restriction enzymes EcoRI and XhoI and then subcloned into pBSK and pBKS plasmid vectors for sequencing. The 0.8 kb cDNA was completely sequenced using an Applied Biosystems 370A Automated DNA sequencer. The partial 5' and 3' nucleotide sequences, confirmed by triplicate sequencing runs, follow:

```
GAGCTGATGC GCACCCTCAT CCGGGTCAAC GTCGAGGGCG TCACGCGTGT CACGCACGCC   60 [SEQ ID NO:1]

GTGCTGCCGG CCATGGTCGA GAGGAAGCGC GGCGCCATTG TCAACATCGG CTCCGGCGCC  120

GCCTCCGTCG TGCCTTCTGA TCCGCTCTAC TCCGTCTACG CCGCTACCAA AGCGTATGTT  180

GACCAATTCT CAAGATGCCT CTATGTTGAG TACAAGAGCA AGGGTATTGA TGTGCAATGC  240

CAGGTGCCCT TATACGTGG                                              259

GCAAGAAGGG GCTGGCCAAG GACGCCAAGA AGAAGGCGCT GTGATTGATG TTTCAGAATG   60 [SEQ ID NO:2]

CATGTTCAGA TTCGCACATT TCCTCATCAC CTGTAGTAGA CACGTGCCTT GCTGTAGTCA  120

CTTTATTAGC TACCATTACC TCCTGAGTCT GTTAAGAATC GAGAATGTCA TTGTTCCATC  180

CGCGGTTATG ATGATGAAAA ATACGATTCT TCAATTCAAA ATGTAACACT AATACGAGTA  240

ATGATGCATG AAATTAACTT GAAGAAGTTG TGCAACTCAG TTGTTTTTCT GAAAAAAAAA  300

AAAAAAAAA                                                         309
```

The sequence displays the 3' poly A tail that is characteristic of cDNAs derived from mRNA. This sequence was compared to the genomic sequence of the glossy8-3142 allele. The 5' end of the cDNA matches the genomic region from the SacI site of the genomic clone (FIG. 2), close to the Mu8 insertion site. The 3' end of the cDNA matches the region of the genomic clone from the XhoI site towards the SacI site. This analysis has, therefore, established that the glossy8 gene is transcribed away from the Mu8 transposon insertion site and towards the left, as can be seen in FIG. 2.

The C-terminal portion of the gl8 protein exhibits a high degree of sequence similarity to β-keto-acyl reductases, which provides suggestive evidence that the glossy8 gene product functions as a reductase in an elongation reaction (or reactions) required for the biosynthesis of cuticular lipids. Further cDNA clones are disclosed in Example 4.

EXAMPLE 3

This example illustrates the endogenous expression of the glossy8 gene in maize, as assessed in a Northern blot experiment.

RNAs were isolated from two-leaf stage seedlings with the genotypes Glossy8/Glossy8 (Q60 F2), glossy8-ref/glossy8-ref and glossy8-3142/glossy8-3142, using the procedure of Dean et al., *EMBO J.*, 4, 3055–3061 (1985). The glossy8-ref and glossy8-3142 alleles had both been backcrossed with the F1 hybrid Q60 for two generations to minimize differences in expression patterns caused by genetic background effect. The 3.6 kb HindIII-SacI fragment from the gl8-3142 genomic clone (FIG. 2) revealed a 1.4-kb gl8 transcript in Northern blots that were prepared using the method disclosed in Sambrook et al., supra. This mRNA was detected in both wildtype and mutant seedlings, but accumulated at higher levels in wildtype seedlings. In wildtype plants, the glossy8 mRNA accumulates to detectable levels at all stages of development and in all organs analyzed, including mature leaf, mature husk, mature ear, endosperm, Q60 F$_2$ seedling root, and mature root.

EXAMPLE 4

This example illustrates methods for the identification of DNA segments that crosshybridize with the glossy8 clone and portions thereof.

Leek and barley libraries were screened to isolate the respective maize gl8 homologs. Hybridization for the first screen was carried out at 50° C. using an 800 bp maize gl8 partial cDNA as the probe. The first screen was washed at 50° C. for 20 minutes each in solutions of 0.1% SDS and decreasing SSPE concentration (1×, 0.5×, 0.2×, and 0.1×). Positives clones were hybridized at 70° C. and washed at 70° C. for 20 minutes each in solutions of 0.1% SDS and decreasing concentrations of SSPE (1×, 0.5×, and 0.2×) in subsequent purifications.

In particular, the barley homolog to maize gl8 was isolated from a sprouted barley-morex cDNA library constructed in the EcoRI site of λ zap II. Phage were plated at a concentration of 40,000 pfu per plate with five plates used. The plates were grown overnight to allow lysis. The plaques were lifted to magna nylon. The filters were hybridized to a 800 bp maize gl8 partial cDNA probe. Filters were washed using standard methods and exposed for two days at −70° C. and a single positive plaque was identified (M1B1). This plaque was purified by a second and third screen using standard methods. A cDNA containing plasmid was excised from purified λ phage by using Stratagene's rapid excision protocol. The plasmid was isolated and retransformed into DH5α. The cDNA was sequenced on both strands using universal and reverse primers on a series of subclones of deletions from the original clone and also sequence-specific primers (CD696 and Bar1) were designed. The cDNA is 1140 bp in length with a 325 amino acid open reading frame. The cDNA appears to be full-length based on a 5' methionine and homologies to similar genes in databases.

The sequence of the barley homolog of gl8 follows:

```
   1 GAATTCCCCG CTCCCTACCG CGGATCGAGC CAACTCACCC CCAAACCCAG [SEQ ID NO:3]
  51 CAAGCACGAT GGCCGGCACG TGCGCCCACG TCGAGTTCCT CCGCGCGCAG
 101 CCGGCGTGGG CGCTGGCCCT CGCGGCCGTC GGCCTCCTCG TCGCCGCCCG
 151 CGCCGCCCTT CGCCTCGCCC TCTGGGTCTA CGCCGCCTTC CTCCGCCCCG
 201 GCAAGCACCT GCGCCGCCGC TACGGGCCCT GGGCCGTCGT CACCGGCGCC
 251 ACCGACGGCA TCGGCCGCGC CATCGCCTTC CGCCTCGCCG CCTCCGGCCT
 301 CGGCCTCGTG CTCGTCGGCC GCAACCCGGA CAAGCTCGCC GCCGTCTCCC
 351 AGGAGATCAG GGCCAAGTAC CCCAAGACCG AGGTCCGCAC CTTCGTGCTC
 401 GACTTCGCCT CCGAGGGGCT CGCCGCCGGG GTGGAGGCGC TCAAGGACTC
 451 CATCCGGGGC CTCGACGTCG GCGTGCTCGT CAACAACGCC GGGGTCTCGT
 501 ACCCGTACGC CCGCTACTTC CACGAGGTGG ACGAGGAGCT CATGCGGAGC
 551 CTCATCCGGG TCAACGTCGA GGGCGTAACG CGGGTCACCC ACGCCGTGCT
 601 CCCGGGCATG GTCGACAGGA AGCGTGGCGC AATCGTCAAC ATCGGCTCCG
 651 GTGCTGCCTC TGTCGTGCCG TCCGATCCAC TCTACTCCGT CTACGCCGCC
 701 ACCAAAGCGT ACGTTGACCA GTTCTCAAGA TGCCTCTATG TTGAGTACAA
 751 GGGTAAGGGC ATCGATGTAC AATGCCAGGT GCCCTTGTAC GTGGCAACAA
 801 AGATGGCATC AATCAGGAGG TCTTCCTTCC TTGTGCCATC CGCGGACACC
 851 TATGCTCGTG CTGCTATTCG CCACATTGGC TATGAGCCGA GGTGCACACC
 901 GTACTGGCCA CACTCTGTTC TGTGGTTCTT GATCTCCCTT CTCCCAGAGT
 951 CGCTGGTGGA CAGTACGCGC CTCAGCATGT GCATCAAAAT CCGCAAGAAG
1001 GGGCAGGCTA AGGATGCCAA GAAGAAAGCG CAGTGATGAT TCATTGTTGA
1051 GATCTGCCAT GTTTGTTCGT CATGTGTAAC GAATCAGTAT TTGTAGCTCT
1101 GTTGTCGGCA TTTCAACATC ATTACCTTCG CGGAATTC
```

The amino acid sequence derived from SEQ ID NO:3 follows:

```
Met Ala Gly Thr Cys Ala His Val Glu Phe Leu Arg Ala Gln Pro Ala  [SEQ ID NO:4]
 1               5                  10                  15

Trp Ala Leu Ala Leu Ala Ala Val Gly Leu Leu Val Ala Ala Arg Ala
                20                  25                  30

Ala Leu Arg Leu Ala Leu Trp Val Tyr Ala Ala Phe Leu Arg Pro Gly
                35                  40                  45

Lys His Leu Arg Arg Arg Tyr Gly Pro Trp Ala Val Val Thr Gly Ala
         50                  55                  60

Thr Asp Gly Ile Gly Arg Ala Ile Ala Phe Arg Leu Ala Ala Ser Gly
65                   70                  75                  80

Leu Gly Leu Val Leu Val Gly Arg Asn Pro Asp Lys Leu Ala Ala Val
                    85                  90                  95

Ser Gln Glu Ile Arg Ala Lys Tyr Pro Lys Thr Glu Val Arg Thr Phe
                100                 105                 110

Val Leu Asp Phe Ala Ser Glu Gly Leu Ala Ala Gly Val Glu Ala Leu
             115                 120                 125

Lys Asp Ser Ile Arg Gly Leu Asp Val Gly Val Leu Val Asn Asn Ala
```

-continued

```
                130                 135                 140
Gly Val Ser Tyr Pro Tyr Ala Arg Tyr Phe His Glu Val Asp Glu Glu
145                 150                 155                 160

Leu Met Arg Ser Leu Ile Arg Val Asn Val Glu Gly Val Thr Arg Val
                165                 170                 175

Thr His Ala Val Leu Pro Gly Met Val Asp Arg Lys Arg Gly Ala Ile
                180                 185                 190

Val Asn Ile Gly Ser Gly Ala Ala Ser Val Val Pro Ser Asp Pro Leu
                195                 200                 205

Tyr Ser Val Tyr Ala Ala Thr Lys Ala Tyr Val Asp Gln Phe Ser Arg
                210                 215                 220

Cys Leu Tyr Val Glu Tyr Lys Gly Lys Gly Ile Asp Val Gln Cys Gln
225                 230                 235                 240

Val Pro Leu Tyr Val Ala Thr Lys Met Ala Ser Ile Arg Arg Ser Ser
                245                 250                 255

Phe Leu Val Pro Ser Ala Asp Thr Tyr Ala Arg Ala Ala Ile Arg His
                260                 265                 270

Ile Gly Tyr Glu Pro Arg Cys Thr Pro Tyr Trp Pro His Ser Val Leu
                275                 280                 285

Trp Phe Leu Ile Ser Leu Leu Pro Glu Ser Leu Val Asp Ser Thr Arg
                290                 295                 300

Leu Ser Met Cys Ile Lys Ile Arg Lys Lys Gly Gln Ala Lys Asp Ala
305                 310                 315                 320

Lys Lys Lys Ala Gln
                325
```

The leek homolog was isolated from screening a leek epidermal cDNA library with the partial maize gl8 cDNA as the probe, using standard methods. DNA was extracted from purified plaques and digested with EcoRI and XhoI and ligated into the EcoRI/XhoI sites of pBSK. Both strands of the cDNA were sequenced using partial deletion subclones and a gene-specific primer (leek1). The leek cDNA clone is 872 bp in length.

The double-stranded sequence of the cDNA insert [SEQ ID NOS:5 and 6] and the translated first 200 amino acids [SEQ ID NO:7] for the leek glossy8 homolog follow:

```
GAATTCGGCA CGAGAGCTTT TTTCTCAAGT AAATATATTC AGAATAGTGA AAACAAGAAA   60 [SEQ ID NO:5]
ACACAACCGT ATAAAGTACA ACCACAAATA CGACGAACAC AAGAGTGCTT AACCACTTAA  120
ACTTCATAAG ACAATTATTT GTAAAGGAAA ACAAAAGCGT AAGATAAATT AAAGGGCGAT  180
CTACAGATCC TTCTTCTTGG CATCCTTGAG CTGCCCCTTT GTGCGGATAC CAAGGCAGAA  240
ACCAAGGCGC CAGTTGTCAA TAGCTGATTC GGGGAGAAGG GATAGCAGGC ACCAAATAGC  300
AGAGTGTGGC CAGTACGGAG TGCATCTAGG CTCATAGCCT ATCCATCTTA AGGCGGCTTT  360
GGCGTAGGTG TCCGATGATG GTACCATGAA TGACGACCTT CGGATTGACG CCATTTTTGT  420
TGCTACATAC AAGGGTACCT GGCACTGAAC ATCTATTCCC TTGCTTTTGT ATTCTACAAA  480
AAGGCATCTT GAGAATTGAT CAACATACGC TTTTGTAGCA GCGTACACCG CATAAAGCGG  540
GTCGGACGGA ATAACAATTG CAGCACCCGA CCCGATATTA ACAATAGCAC CTTTCTTCCT  600
TTCGATCATG CCCGGAAGCA CAGCATGCGT AACCCTAGTA ACTCCCTCCA CATTTACCTT  660
AATCAAATTC CTCAACAGCT CATCGTCGAC TTCGTGAAAA TATCGTGCAT ACGGATACGA  720
CACGCCCGCG TTATTAACCA AAACACCAAC ATCTTTTCCC TTGATACAT CCTTAATCCT  780
TTCGACACCT TCCACCAAAT CGCCTGAAAA GTCCACAACT ACAGTCTCGA CTTTAATCCC  840
GCTGTTTTTA GACAAAATCT CGTGCCGAAT TC                                872
```

-continued

```
GAATTCGGCA CGAGATTTTG TCTAAAAACA GCGGGATTAA AGTCGAGACT GTAGTTGTGG    60    [SEQ ID NO:6]

ACTTTTCAGG CGATTTGGTG GAAGGTGTCG AAAGGATTAA GGATGCTATC AAGGGAAAAG   120

ATGTTGGTGT TTTGGTTAAT AACGCGGGCG TGTCGTATCC GTATGCACGA TATTTTCACG   180

AAGTCGACGA TGAGCTGTTG AGGAATTTGA TTAAGGTAAA TGTGGAGGGA GTTACTAGGG   240

TTACGCATGC TGTGCTTCCG GGCATGATCG AAAGGAAGAA AGGTTGCTAT TGTTAATATC   300

GGGTCGGGTG CTGCAATTGT TATTCCGTCC GACCCGCTTT ATGCGGTGTA CGCTGCTACA   360

AAAGCGTATG TTGATCAATT CTCAAGATGC CTTTTTGTAG AATACAAAAG CAAGGGAATA   420

GATGTTCAGT GCCAGGTACC CTTGTATGTA GCAACAAAAA TGCGTCAATC CGAAGGTCGT   480

CATTCATGGT ACCATCATCG GACACCTACG CCAAAGCCGC CTTAAGATGG ATAGGCTATG   540

AGCCTAGATG CACTCCGTAC TGGCCACACT CTGCTATTTG GCGCCTGCTA TCCCTTCTCC   600

CCGAATCAGC TATTGACAAC TGGCGCCTTG GTTTCTGCCT TGGTATCCGC ACAAAGGGGC   660

AGCTCAAGGA TGCCAAGAAG AAGGATCTGT AGATCGCCCT TTAATTTATC TTACGCTTTT   720

GTTTTCCTTT ACAAATAATT GTCTTATGAA GTTTAAGTGG TTAAGCACTC TTGTGTTCGT   780

CGTATTTGTG GTTGTACTTT ATACGGTTGT GTTTTCTTGT TTTCACTATT CTGAATATAT   840

TTACTTGAGA AAAAGCTCT CGTGCCGAAT TC                                  872
```

```
    Ile Arg His Glu Ile Leu Ser Lys Asn Ser Gly Ile Lys Val Glu Thr       [SEQ ID NO:7]
    1               5                   10                  15

Val Val Val Asp Phe Ser Gly Asp Leu Val Glu Gly Val Glu Arg Ile
                    20                  25                  30

Lys Asp Ala Ile Lys Gly Lys Asp Val Gly Val Leu Val Asn Asn Ala
                35                  40                  45

Gly Val Ser Tyr Pro Tyr Ala Arg Tyr Phe His Glu Val Asp Asp Glu
            50                  55                  60

Leu Leu Arg Asn Leu Ile Lys Val Asn Val Glu Gly Val Thr Arg Val
    65                  70                  75                  80

Thr His Ala Val Leu Pro Gly Met Ile Glu Arg Lys Lys Gly Ala Ile
                    85                  90                  95

Val Asn Ile Gly Ser Gly Ala Ala Ile Val Ile Pro Ser Asp Pro Leu
                    100                 105                 110

Tyr Ala Val Tyr Ala Ala Thr Lys Ala Tyr Val Asp Gln Phe Ser Arg
                    115                 120                 125

Cys Leu Phe Val Glu Tyr Lys Ser Lys Gly Ile Asp Val Gln Cys Gln
                    130                 135                 140

Val Pro Leu Tyr Val Ala Thr Lys Met Ala Ser Ile Arg Arg Ser Ser
    145                 150                 155                 160

Phe Met Val Pro Ser Ser Asp Thr Tyr Ala Lys Ala Ala Leu Arg Trp
                    165                 170                 175

Ile Gly Tyr Glu Pro Arg Cys Thr Pro Tyr Trp Pro His Ser Ala Ile
                    180                 185                 190

Trp Cys Leu Leu Ser Leu Leu Pro
                195                 200
```

Screening the GenBank database for homologous sequences to the maize glossy8 amino acid sequence also allowed identification of a related Arabidopsis sequence. The algorithm Blast identified an expressed sequence tag (EST), which is a randomly sequenced cDNA identified as Clone ID 105H4T7, GenBank ID T22476, and NCBI ID 312378. The Arabidopsis EST was obtained from the Arabidopsis Biological Resource Center DNA Stock Center. Dideoxy sequencing of both strands of purified plasmid from all three homologs was performed. Universal and reverse primers were used on the native clones and on subclones from the original clone, where convenient. Gene-specific primers were designed as necessary to complete double-stranded sequencing.

In particular, the Arabidopsis homolog 105H4T7 was sequenced using universal, reverse, and designed primers (AR612 and AR675). The clone was 896 bp long with a 253 amino acid open reading frame. Here follow the nucleotide and amino acid sequences of the Arabidopsis gl8 homolog:

```
GAC CCA CGC GTC CGG TTA GCC CAG AAA GGT CTT AAC CTT ATA CTC GTT    48 [SEQ ID NO:8]
GCT CGT AAC CCA GAC AAG CTC AAA GAT GTC TCT GAT TCC ATC AGA TCT    96
AAG TAT AGT CAA ACT CAG ATC TTG ACC GTT GTG ATG GAT TTC TCT GGA   144
GAT ATT GAT GAA GGT GTG AAA CGG ATT AAG GAG AGT ATT GAA GGA TTA   192
GAT GTT GGG ATT TTG ATT AAT AAT GCT GGC ATG TCT TAT CCT TAT GCT   240
AAG TAT TTT CAT GAG GTT GAT GAA GAG TTG ATC AAT AAC TTG ATT AAG   288
ATC AAT GTT GAA GGA ACT ACT AAA GTT ACT CAA GCT GTG TTG CCT AAT   336
ATG CTT AAG AGG AAG AAA GGT GCT ATT ATT AAT ATG GGT TCT GGT GCT   384
GCT GCT CTT ATT CCT TCT TAT CCT TTT TAC TCT GTT TAT GCT GGT GCT   432
AAA ACG TAC GTG GAT CAG TTC ACA AAG TGT CTA CAT GTT GAG TAT AAG   480
AAG AGT GGG ATT GAT GTT CAA TGC CAG GTT CCC TTG TAT GTT GCA ACA   528
AAG ATG ACA AAA ATA AGA AGA GCA TCC TTC TTA GTT GCA TCA CCA GAG   576
GGT TAC GCA AAG GCA GCA CTG CGT TTT GTA GGC TAT GAA GCA CAA TGC   624
ACA CCG TAC TGG CCT CAC GCT CTC ATG GGT GCA GTT GTC TCT GCA TTG   672
CCC GAA AGC GTT TTT GAA TCA TTT AAC ATC AAG AGA TGC CTC CAG ATC   720
CGG AAG AAG GGT CTC CAA AAA GAC TCC ATG AAG AAA GAA TGAATCTTCC   769
AGGTTTAAGT TACTACCAAG AATTCCTTC TTCTGAAGTT GTTGGTTTCT TGAAAAGCTT   829
CTGTTCTGAA TCTTTTGTAA GACTTGTACT CTTTAGTTTT CTAAGTTTTT TAAAAAAAA   889
AAAAAAA
```

```
Asp Pro Arg Val Arg Leu Ala Gln Lys Gly Leu Asn Leu Ile Leu Val    [SEQ ID NO:9]
1               5                   10                  15
Ala Arg Asn Pro Asp Lys Leu Lys Asp Val Ser Asp Ser Ile Arg Ser
            20                  25                  30
Lys Tyr Ser Gln Thr Gln Ile Leu Thr Val Val Met Asp Phe Ser Gly
        35                  40                  45
Asp Ile Asp Glu Gly Val Lys Arg Ile Lys Glu Ser Ile Glu Gly Leu
50                  55                  60
Asp Val Gly Ile Leu Ile Asn Asn Ala Gly Met Ser Tyr Pro Tyr Ala
65                  70                  75                  80
Lys Tyr Phe His Glu Val Asp Glu Glu Leu Ile Asn Asn Leu Ile Lys
        85                  90                  95                  100
Ile Asn Val Glu Gly Thr Thr Lys Val Thr Gln Ala Val Leu Pro Asn
                100                 105                 110
Met Leu Lys Arg Lys Lys Gly Ala Ile Ile Asn Met Gly Ser Gly Ala
            115                 120                 125
Ala Ala Leu Ile Pro Ser Tyr Pro Phe Tyr Ser Val Tyr Ala Gly Ala
        130                 135                 140
Lys Thr Tyr Val Asp Gln Phe Thr Lys Cys Leu His Val Glu Tyr Lys
145                 150                 155                 160
Lys Ser Gly Ile Asp Val Gln Cys Gln Val Pro Leu Tyr Val Ala Thr
                165                 170                 175
Lys Met Thr Lys Ile Arg Arg Ala Ser Phe Leu Val Ala Ser Pro Glu
            180                 185                 190
Gly Tyr Ala Lys Ala Ala Leu Arg Phe Val Gly Tyr Glu Ala Gln Cys
```

-continued

```
                    195                 200                 205
Thr Pro Tyr Trp Pro His Ala Leu Met Gly Ala Val Val Ser Ala Leu
    210                 215                 220

Pro Glu Ser Val Phe Glu Ser Phe Asn Ile Lys Arg Cys Leu Gln Ile
225                 230                 235                 240

Arg Lys Lys Gly Leu Gln Lys Asp Ser Met Lys Lys Glu
                245                 250
```

Accordingly, using standard hybridization methods of cDNA libraries from other organisms and standard computer search methods of a sequence databank, related or homologous nucleic acids and polypeptides were identified with respect to maize glossy8.

EXAMPLE 5

This example sets forth the DNA and amino acid sequences of the maize glossy1 gene and glossy1 homologs from other species.

A cDNA clone was isolated using the methods set forth in Example 2, and as further elucidated in Sambrook et al., supra. Specifically, a cDNA library made from mRNA isolated from seedlings of the maize inbred line B73 was screened by hybridization using as a probe a mixture of fragments A and B isolated from the 12.5-kb HindIII clone of the g11-755048 clone. Fragment A is a 600 bp BamHI/SalI fragment located approximately 800 bp from the Mu1 transposon in this clone. Fragment B is a 700 bp SacI fragment located approximately 1 kb on the other side of the Mu1 transposon. From a total of 500,000 recombinant phage that were screened, two classes of cDNA clones were isolated. One class contains a 0.8 kb cDNA insert and the other class contains a 1.6 kb insert. Restriction mapping and cross-hybridization experiments established that the 0.8 kb cDNA is a partial clone of the 1.6 kb cDNA. All subsequent investigations were performed using the longer 1.6 kb cDNA clone.

The partial 5' and 3' sequences of the cDNA insert and the translated amino acids of the maize glossy1 gene follow:

```
GAATTCGGCA CGAGGTCCAC GGTCCACACA CGCCTTCCTT ATATCGGCGC TCACGGTTCT   60 [SEQ ID NO:10]
ATAAAAAAAA CACAGTACGA GCAGAGCAAG GCGGCCGTGA GCTGAGCTGA GGGAAGGACG  120
ACGTACGGCA CAGTTGCTAG CCCGGCCGCC GGAGCTCTCC GTGATCTGGG CCGCCAGCAA  180
CAGCATGGGT GCCGCGCTCT TGGCTTCTTG GCCATGGGAC AACCTCGGCT TCTACAAGTA  240
CGTCCTGTAC GGGCCGCTGG TGGGCAAGGC GGTGGCGTCA CGGGCGTGGG AGGCGGCGAG  300
CCCCGACCGC TGGATCCTCC TCCTGCTCCT CCTCTTCGGC CTCCGCGCGC TCACCTACCA  360
GCTCTGGAGC TCCTTCAGCA ACATGCTCTT CGCCACACGC CGGCGCCGCG TCGTCCGCGA  420
CGGCGTCGAC TTCGACCAGA TCGACAAGGA GTGGGACTGG GACAACTTCC TGATCCTGCA  480
CGCCCTGATG GCGGCCGCGG CGCTGTGCGC GTTCCCGTCG CTGCGGCATC TCCCGGCGTG  540
GGACGGCCGG GGGTTCGCCG TCGCGCTCGT CGCCCACGCG GCGGCCACCG AGCCCCTCTC  600
CTACCTGGCG CACAGGGCGC TCCACGGCAG CAGCGGCCGC CTCTACGCGC GCTACCACTC  660
GCTGCACCAC TCCAGCAGGG TGCCGCAGCC GTTCACGGCG GGGCTGGCCA CGCCGCTGGA  720
GCACGTGGCG CTGGGCGCGC TCATGTCGCT GCCCCTCGCG GCCGCGCGCG CCGCCGGGTG  780
CGCCTCCGTC GCGCTCGCCT TCGCCTACGT GCTCGCCTTC GACTCCCTCC GCGCCATGGG  840
CCACTGCAAC GTCGAGGTCG TCCCGGCCTC GCTCTTCCGG GCCATCCCGG CCCTCAGATA  900
CGTTCTCTAC ACCCCGACGT ACGTACCACG CGATTCACCA CACCAAGAAG              950
AATCGACCGA CGCTCGTGGG ACATGCAGAG GAAGATGAGC GCAGGTACAC ACGTCGTCTC   60 [SEQ ID NO:11]
GTTTTATGTC CCTGGTCCAT GACAGGCCAC CAAACTACCT ATATTGGACT AACCCATTTT  120
AGCTTTAACA ACCTTACTAG CTAAGGCATC CACACACACA TACCCATACA ACTTAGCAAT  180
CCTGCACTAG CCGGAACACT GACACTGAAA CAAAGAGCGG ACCCCTTTGA CCAGAACTGC  240
CTAGTAAACA GACATCAAGA AAGAGTGTTA GGCAACCAGC CGCTACAGAC GAGCTAAACA  300
TCCACCAACG AGCTCTTTCA CCACCTGCGC AACTTGCTCT GTTGTTCTCT GTTGTCCATT  360
GAAGATTATG TTGTTGCTTT CCAACCATAC GCTCCACCAG AAGTAAATTA GTAGGCCATC  420
```

-continued

```
GAAACTTTTT CTTGATTGCT TGCTATAGAG CATCCTCAGT CTATGCCACC AAGTGTATAG  480

GGTTCCCGTC TTTGGAGTAC CGTCTAGGAA CCACAGATCG GTCCAAGACA AGATCATGCT  540

CCACACTTCC TCATATATCA CCAAAGCAAA AAAAAAAAAA AAAAA                 585
```

```
    Met Glu Ala Ala Leu Leu Ala Ser Trp Pro Trp Asp Asn Leu Gly Phe   [SEQ ID NO:12]
    1               5                   10                  15

Tyr Lys Tyr Val Leu Tyr Gly Pro Leu Val Gly Lys Ala Val Ala Ser
                    20                  25                  30

Arg Ala Trp Glu Ala Ala Ser Pro Asp Arg Trp Ile Leu Leu Leu Leu
                35                  40                  45

Leu Leu Phe Gly Leu Arg Ala Leu Thr Tyr Gln Leu Trp Ser Ser Phe
        50                  55                  60

Ser Asn Met Leu Phe Ala Thr Arg Arg Arg Val Val Arg Asp Gly
    65                  70                  75                  80

Val Asp Phe Asp Gln Ile Asp Lys Glu Trp Asp Trp Asp Asn Phe Leu
                    85                  90                  95

Ile Leu His Ala Leu Met Ala Ala Ala Leu Cys Ala Phe Pro Ser
                    100                 105                 110

Leu Arg His Leu Pro Ala Trp Asp Gly Arg Gly Phe Ala Val Ala Leu
                115                 120                 125

Val Ala His Ala Ala Thr Glu Pro Leu Ser Tyr Leu Ala His Arg
        130                 135                 140

Ala Leu His Glu Ser Ser Gly Arg Leu Tyr Ala Arg Tyr His Ser Leu
    145                 150                 155                 160

His His Ser Ser Arg Val Pro Gln Pro Phe Thr Ala Gly Leu Ala Thr
                    165                 170                 175

Pro Leu Glu His Val Ala Leu Gly Ala Leu Met Ser Leu Pro Leu Ala
                180                 185                 190

Ala Ala Arg Ala Ala Gly Cys Ala Ser Val Ala Leu Ala Phe Ala Tyr
                195                 200                 205

Val Leu Ala Phe Asp Ser Leu Arg Ala Met Gly His Cys Asn Val Glu
        210                 215                 220

Val Val Pro Ala Ser Leu Phe Arg Ala Ile Pro Ala Leu Arg Tyr Val
    225                 230                 235                 240

Leu Tyr Thr Pro Thr Tyr Val Pro Arg Asp Ser Pro His Gln Glu Gly
                    245                 250                 255

Gly Gln Leu Leu Ser Leu His Ala Ala Val Arg Ser Ala Gly Trp His
                260                 265                 270

Asn Arg Pro Thr Leu Val Gly His Ala Glu Glu Asp Glu Arg Arg Tyr
            275                 280                 285

Thr Arg Arg Leu Val Leu Cys Pro Trp Ser Met Thr Gly His Gln Thr
        290                 295                 300

Thr Tyr Ile Gly Leu Thr His Phe Ser Phe Asn Asn Leu Thr Ser
    305                 310                 315
```

A partial homolog to maize glossy1 was identified from the GenBank database. The partial homolog (Accession No. L33792) is identified in the database as a *Senecio odorus* epidermal mRNA, the 3' end of which has no known function. In comparing the maize sequences recited above with the corresponding Senecio sequences recited below, the two genes can be seen to differ a great deal at their carboxy termini. The Senecio homologous glossy1 sequences follow:

```
AA GGG GAT GAT GAT CTA GCA AAC AAT TGG TGT TTC CAC ATT CTA GTG    47  [SEQ ID NO:13]
ATA AGC TTG CTT AGA TTT AAT CTA TAT ATG TGG TAT ACT AAC ATT TGT   95
```

```
                                        -continued
AAC ATG CTT TTC CTC ACT CGG AAT CGT CGG ATT TTA CAT CAA AGC ATT    143

GAC TTT AAC CAG ATT GAT AAA GAA TGG AAC TGG GAC AAT TTT GTA ATT    191

TTA CAA GCT CTA ATA GCT TCA TTG GCG ATT TAT ATG TTC CCT CAA GAA    239

TTT GCA AAC TTA CCG GTG TGG AAA ACC AAA GGG CTT GTG GCA ATT GTG    287

GTG ATA CAC GTG GTT GTA TCA GAG CCA CTT TAC TAT TGG TTG CAT AGA    335

TTG TTA CAT ACA AAT TAC CTA TTT ACC CCT TAC CAT TCT TTC CAC CAT    383

TCA TCA GCT GTG CCC CAA CCA GTT ACA GTT GGA AGC ACC ACA TTC TTG    431

GAG GAG TTA TTA GTT ACG GCG GTG CTT GGA CTA CCA ATA CTT GGT TGT    479

AGT TTG TCT GGA TAC GGA TCT AAA TCC ATA ATA TAT GGC TAT GTT TTG    527

GTC TTT GAT TTC TTA CGA TGT TTG GGG CAT TCA AAC GTT GAG ATC ATG    575

CCT CAT TGG ATT TTC GAC TAC TTT CCT TTC TTC AGA TTC ATT ATC TAC    623

ACC CCA ACA TAC TAT AGC CTA CAC CAC AGT GAG ATG AAG AGC AAC TAT    671

TGC CTA TTT ATG CCA CTT TAT GAC ACC ATG TGG AAC ACT TTG AAC ACG    719

AAG TCG TGG GGT CTA CAC AAG AAA ATA AGT CTA GAC TCA GGC AAG TCA    767

ACG CGG GTG CCA GAT TTT GTG TTC TTG GCA CAT GTG GTG GAT ATA ACA    815

TCT GCA CTA CAT GTT CCC TTC GTC ATC AGA TCA TTT TCA GCG ATG GCT    863

TAT AGT GCT AGG CTT TTC TTG CTT CCA TTA TGG CCA TTT ACT TTC GCC    911

GTG ATG ATA GTG ATG TGG GCT AGG TCT AAG ACA TTT CTT TTG TCT TCT    959

TAC AAC TTA AGA GGC GGA TTG CAC CAA ACT TGG GTT GTT CCT CGT TTT   1007

GGC TTC CAG TAT TTC TTG CCA TTC GCT TGC CAA GGC ATT AAC AAT CAT   1055

ATT GAG GAG GCC ATT CTT AGA GCT GAC AAA TTG GGT GTG AAG GTC ATT   1103

AGC CTT GCT GCG TTA AAT AAG AAT GAA TCA CTT AAC AGA GGT GGA ACG   1151

TTG TTT GTG AAA AAA CAC CCG AAT TTG AAA GTA CGG GTG GTC CAT GGA   1199

AAT ACA TTG ACA GCC GCT GTT ATC CTC AAT GAG ATT AAT GAA GAC GTG   1247

AAA GAG GTG TTT CTC ACC GGA GCC ACT TCA AAG CTT GGA CGG GCC ATC   1295

GCC CTT TAC CTT TGT CGA CGA GGC GTT CAT GTT CTT ATG TTG ACC CTA   1343

TCA ACG GAG AGA TTT CAA AAC ATC CAA GAA GAA GCA CCA TCA AAA TGC   1391

AGG AAG AAT TTG GTC CAA GTC ACC AAG TAC CAA GCA GCC AAA AAT TGC   1439

AAG ACA TGG GTG ATC GGA AAA TGG ATA ACA CCG GGA CAA CAA CGT TGG   1487

GCG CCA TCA GGA ACT CAT TTT CAT CAG TTT GTG GTG CCA CCC ATT TTA   1535

GCT TTC AGA AGA ACT GCA CCT ACG GAG ACC TTG CCG CTT ATG AAA CTT   1583

CCC GAT GAT GTT GAA GGC CTT GGA TCA TGC GAG TAT ACA ATG GGA AGA   1631

GGA ATA GTG CAT GCA TGC CAT GCC GGA GGG GTT GTA CAT AGC TTG GAA   1679

GGA TGG ACT CAT CAT GAA GTT GGT GCT CTT GAT GTT GAT CGA ATC GAC   1727

GTC GTT TGG AAA GCA GCT TTA AAG CAT GGT CTT CAA TCT GTT TCC AGT   1775

CTT CCC AAA TGATCTTATT TCTAATCATT TGTTTAAATT CATATTTAAT          1824

ATCAGAATCA TTATTTTTTG TTTTACATTC TTGAATTTGG TACTCTTAGT TCGATATTAC 1884

AATATGTATG ATTGCGTATT AATTGGAAAG TAATGCAGAT GTTTATGGAT T         1935

Gly Asp Asp Asp Leu Ala Asn Asn Trp Cys Phe His Ile Leu Val Ile    [SEQ ID NO:14]
       1               5                  10                  15

Ser Leu Leu Arg Phe Asn Leu Tyr Met Trp Tyr Thr Asn Ile Cys Asn
```

-continued

```
                   20                  25                  30
Met Leu Phe Leu Thr Arg Asn Arg Ile Leu His Gln Ser Ile Asp
                35                  40                  45

Phe Asn Gln Ile Asp Lys Glu Trp Asn Trp Asp Asn Phe Val Ile Leu
 50                  55                  60

Gln Ala Leu Ile Ala Ser Leu Ala Ile Tyr Met Phe Pro Gln Glu Phe
 65                  70                  75                  80

Ala Asn Leu Pro Val Trp Lys Thr Lys Gly Leu Val Ala Ile Val Val
                 85                  90                  95

Ile His Val Val Val Ser Glu Pro Leu Tyr Tyr Trp Leu His Arg Leu
                100                 105                 110

Leu His Thr Asn Tyr Leu Phe Thr Pro Tyr His Ser Phe His His Ser
        115                 120                 125

Ser Ala Val Pro Gln Pro Val Thr Val Gly Ser Thr Thr Phe Leu Glu
 130                 135                 140

Glu Leu Leu Val Thr Ala Val Leu Gly Leu Pro Ile Leu Gly Cys Ser
145                 150                 155                 160

Leu Ser Gly Tyr Gly Ser Lys Ser Ile Ile Tyr Gly Tyr Val Leu Val
                165                 170                 175

Phe Asp Phe Leu Arg Cys Leu Gly His Ser Asn Val Glu Ile Met Pro
                180                 185                 190

His Trp Ile Phe Asp Tyr Phe Pro Phe Arg Phe Ile Ile Tyr Thr
        195                 200                 205

Pro Thr Tyr Tyr Ser Leu His His Ser Glu Met Lys Ser Asn Tyr Cys
 210                 215                 220

Leu Phe Met Pro Leu Tyr Asp Thr Met Trp Asn Thr Leu Asn Thr Lys
225                 230                 235                 240

Ser Trp Gly Leu His Lys Lys Ile Ser Leu Asp Ser Gly Lys Ser Thr
                245                 250                 255

Arg Val Pro Asp Phe Val Phe Leu Ala His Val Val Asp Ile Thr Ser
                260                 265                 270

Ala Leu His Val Pro Phe Val Ile Arg Ser Phe Ser Ala Met Ala Tyr
        275                 280                 285

Ser Ala Arg Leu Phe Leu Leu Pro Leu Trp Pro Phe Thr Phe Ala Val
 290                 295                 300

Met Ile Val Met Trp Ala Arg Ser Lys Thr Phe Leu Leu Ser Ser Tyr
305                 310                 315                 320

Asn Leu Arg Gly Arg Leu His Gln Thr Trp Val Val Pro Arg Phe Gly
                325                 330                 335

Phe Gln Tyr Phe Leu Pro Phe Ala Cys Gln Gly Ile Asn Asn His Ile
                340                 345                 350

Glu Glu Ala Ile Leu Arg Ala Asp Lys Leu Gly Val Lys Val Ile Ser
        355                 360                 365

Leu Ala Ala Leu Asn Lys Asn Glu Ser Leu Asn Arg Gly Gly Thr Leu
 370                 375                 380

Phe Val Lys Lys His Pro Asn Leu Lys Val Arg Val His Gly Asn
385                 390                 395                 400

Thr Leu Thr Ala Ala Val Ile Leu Asn Glu Ile Asn Glu Asp Val Lys
                405                 410                 415

Glu Val Phe Leu Thr Gly Ala Thr Ser Lys Leu Gly Arg Ala Ile Ala
                420                 425                 430

Leu Tyr Leu Cys Arg Arg Gly Val His Val Leu Met Leu Thr Leu Ser
        435                 440                 445
```

-continued

```
Thr Glu Arg Phe Gln Asn Ile Gln Glu Glu Ala Pro Ser Lys Cys Arg
        450                 455                 460

Lys Asn Leu Val Gln Val Thr Lys Tyr Gln Ala Ala Lys Asn Cys Lys
465                 470                 475                 480

Thr Trp Val Ile Gly Lys Trp Ile Thr Pro Gly Gln Gln Arg Trp Ala
                485                 490                 495

Pro Ser Gly Thr His Phe His Gln Phe Val Val Pro Pro Ile Leu Ala
            500                 505                 510

Phe Arg Arg Thr Ala Pro Thr Glu Thr Leu Pro Leu Met Lys Leu Pro
        515                 520                 525

Asp Asp Val Glu Gly Leu Gly Ser Cys Glu Tyr Thr Met Gly Arg Gly
530                 535                 540

Ile Val His Ala Cys His Ala Gly Gly Val Val His Ser Leu Glu Gly
545                 550                 555                 560

Trp Thr His His Glu Val Gly Ala Leu Asp Val Asp Arg Ile Asp Val
                565                 570                 575

Val Trp Lys Ala Ala Leu Lys His Gly Leu Gln Ser Val Ser Ser Leu
            580                 585                 590

Pro Lys
```

Other homologous sequences were also identified via the computer database search, namely a rice-derived and an Arabidopsis-derived EST. The rice EST has been cataloged as NCBI ID 72320, EST ID R1CS2751A, Clone ID S2751, and GenBank ID D40658. The organism used was *Oryza sativa*, strain Nipponbase, subspecies Japonica, and the cDNA was made from mRNA isolated from 8-day old rice etiolated shoots. The nucleic acid and amino acid sequences of the rice gl1 homolog follow:

```
AAC ATG CTC TTC TTC ACC CGC CGC CGC CGC GTC GTC GAC GAC GGC GTC      48  [SEQ ID NO:15]
GAC TTC CGC CAG ATC GAC ACC GAG TGG GAC TGG GAT AAC ATG GTG ATC      96
ATG CAA ACC CTA ATC GCG GCG GTG CTG GTC ACC AGC CGT GTC TTC CCT     144
GCC ACG TCG GAT CTC TCG GCG TGG GAC CTA CGT GGG TGG GCC ATC GCT     192
GTG GTG CTG CAC GTG GCC GTT TCA GAG CCG GCC TTC TAC TGG GCC CAC     240
CGG GCC CTC CAT CTG GGC CCA CTC TTC AGC GGG TAC CAC TCC TTG CAC     288
CAC TCC TTC CAA GCC ACC CAA GCT CTC ACA GCT GGG TTC GTG ACG CCA     336
TTG GAG AGC CTG ATC CTG ACG CTG GTG GCG TGG CCC CAC TTG CAG GGC     834
CTT CAT GGC GGG ACA CGG CTC CGT GAG CTG GTC TAT GGA CAC ATC TTC     432
TCT TCG ACT ACT CCG GTC CAT GGG GTA CAG CAA CGT CGA GGT CAT CTC     480
ACA CAA GAC TTC CAG GAT TTT CCC TTT CTC AGA TAC CTC ATC TAC ACA     528
CCA TCG TAT CTT AGC CTA CAC CAC AGG GAG AAG GAC TCC AAT TTC TGC     576
CTG TTC ATG CCT CTC TTT GAT GCC CTG GGA GGG ACC CTC AAC CCC AAG     624
TCT TGG CAG CTT CAG AAG GAG GTT GAC CTA GGA AAG AAC CAT CGG GTG     672
CCG GAC TTT GTG TTC CTG GTG CAC GTG GTG GAC GTG GTG TCG TCG ATG     720
CAC GTG CCA TTC GCG TTC CGA GCG TGC AGC TCG CTG CCG TTC GCG ACG     768
CAC CTC GTC CTT CTC CCG CTC TGG CCC ATC GCC TTC GGC TTC ATG CTC     816
CTC CAG TGG TTC TGC TCC AAG ACC TTC ACT GTC AGC TTC TAT AAG CTC     864
CGC GGC TTC CTC CAC CAG ACC TGG AGC GTG CCC CGC TAC GGC TTC CAG     912
TAT TTC ATC CCT TCG GCG AAG AAG GGC ATC AAT GAG ATG ATC GAG CTC     960
```

-continued

```
GCG ATC CTG AGG GCG GAC AAG ATG GGC GTC AAA GTG CTC AGC CTT GCT      1008

GCA CTC AAC AAG AAT GAG GCG CTC AAT GGG GGT GGC ACG CTG TTC GTC      1056

CGC AAG CAT CCC GAC CTG CGG GTG AGG GTG GTG CAC GGC AAC ACC CTG      1104

ACG GCG GCG GTG ATC CTC AAC GAG ATC CCC GGC GAC GTC GCG GAG GTG      1152

TTC CTC ACC GGT GCG ACG TCG AAG CTC GGC AGA GCC ATC GCT CTC TAC      1200

TTC TGT AGG AAG AAG ATC AGA GTC TTG ATG CTG ACA CTG TCA ACG GAG      1248

AGG TTC ATG AAT ATT CAG AGG GAG GCC CCT GCG GAG TTC CAG CAG TAT      1296

CTG GTC CAG GTC ACC AAG TAC CAG GCT GCA CAG AAT TGC AAG ACG TGG      1344

ATC GTG GGG AAG TGG CTG TCG CCG AGG GAG CAG CGG TGG GCG CCG GCG      1392

GGG ACG CAC TTC CAC CAG TTC GTG GTG CCG CCG ATC ATC GGG TTC CGG      1440

CGG GAC TGC ACG TAC GGG AAG CTC GCC GCG ATG AGG CTG CCG GAG GAC      1488

GTG GAG GGG CTG GGG ACG TGC GAG TAC ACC ATG GGC CGC GGC GTC GTG      1536

CAC GCG TGC CAC GCC GGC GGC GTC GTC CAC TTC CTG GAG GGG TGG GAC      1584

CAC CAC GAG GTC GGC GCC ATC GAC GTC GAC CGG ATC GAC GCC GTC TGG      1632

AAC GCC GCG CTC AGG CAC GGC CTC ACG CCG GCG TGAACGCCGG CGACGGCGAC    1685

GGCGGCTAGT AGTAACTACG TACAGCACGG GGACGCCGAA TAACTTTCGT GTTGTGCGTG    1745

TGTGTCGATC GATTGTACGT TGCATTGTTC GCTCGCCCGG CTAGCTTAAT TAATTATCGG    1805

GCGTGCTTGT GTTGTGTGTT GATAGCTAGC GTCGTACGTA AGAATACCGC AGAAATGACA    1865

AGAAAGAATG GATGATTCCT CGTAAAAAAA AAAAAAAA                            1903
```

Asn Met Leu Phe Phe Thr Arg Arg Arg Val Val Asp Asp Gly Val    [SEQ ID NO:16]
1               5                   10                  15

Asp Phe Arg Gln Ile Asp Thr Glu Trp Asp Trp Asp Asn Met Val Ile
                20                  25                  30

Met Gln Thr Leu Ile Ala Ala Val Leu Thr Ser Arg Val Phe Pro
        35                  40                  45

Ala Thr Ser Asp Leu Ser Ala Trp Asp Leu Arg Gly Trp Ala Ile Ala
    50                  55                  60

Val Val Leu His Val Ala Val Ser Glu Pro Ala Phe Tyr Trp Ala His
65                  70                  75                  80

Arg Ala Leu His Leu Gly Pro Leu Phe Ser Arg Tyr His Ser Leu His
                85                  90                  95

His Ser Phe Gln Ala Thr Gln Ala Leu Thr Ala Gly Phe Val Thr Pro
                100                 105                 110

Leu Glu Ser Leu Ile Leu Thr Leu Val Ala Trp Pro His Leu Gln Gly
            115                 120                 125

Leu His Gly Gly Thr Arg Leu Arg Glu Leu Val Tyr Gly His Ile Ser
    130                 135                 140

Ser Ser Thr Thr Pro Val His Gly Val Gln Gln Arg Arg Gly His Leu
145                 150                 155                 160

Thr Gln Asp Phe Gln Asp Phe Pro Phe Leu Arg Tyr Leu Ile Tyr Thr
                165                 170                 175

Pro Ser Tyr Leu Ser Leu His His Arg Glu Lys Asp Ser Asn Phe Cys
            180                 185                 190

Leu Phe Met Pro Leu Phe Asp Ala Leu Gly Gly Thr Leu Asn Pro Lys
        195                 200                 205

Ser Trp Gln Leu Gln Lys Glu Val Asp Leu Gly Lys Asn His Arg Val
    210                 215                 220

-continued

```
Pro Asp Phe Val Phe Leu Val His Val Asp Val Val Ser Ser Met
225                 230                 235                 240

His Val Pro Phe Ala Phe Arg Ala Cys Ser Ser Leu Pro Phe Ala Thr
                245                 250                 255

His Leu Val Leu Leu Pro Leu Trp Pro Ile Ala Phe Gly Phe Met Leu
            260                 265                 270

Leu Gln Trp Phe Cys Ser Lys Thr Phe Thr Val Ser Phe Tyr Lys Leu
        275                 280                 285

Arg Gly Phe Leu His Gln Thr Trp Ser Val Pro Arg Tyr Gly Phe Gln
    290                 295                 300

Tyr phe Ile Pro Ser Ala Lys Lys Gly Ile Asn Glu Met Ile Glu Leu
305                 310                 315                 320

Ala Ile Leu Arg Ala Asp Lys Met Gly Val Lys Val Leu Ser Leu Ala
                325                 330                 335

Ala Leu Asn Lys Asn Glu Ala Leu Asn Gly Gly Thr Leu Phe Val
            340                 345                 350

Arg Lys His Pro Asp Leu Arg Val Arg Val Val His Gly Asn Thr Leu
        355                 360                 365

Thr Ala Ala Val Ile Leu Asn Glu Ile Pro Gly Asp Val Ala Glu Val
    370                 375                 380

Phe Leu Thr Gly Ala Thr Ser Lys Leu Gly Arg Ala Ile Ala Leu Tyr
385                 390                 395                 400

Phe Cys Arg Lys Lys Ile Arg Val Leu Met Leu Thr Leu Ser Thr Glu
                405                 410                 415

Arg Phe Met Asn Ile Gln Arg Glu Ala Pro Ala Glu Phe Gln Gln Tyr
            420                 425                 430

Leu Val Gln Val Thr Lys Tyr Gln Ala Ala Gln Asn Cys Lys Thr Trp
        435                 440                 445

Ile Val Gly Lys Trp Leu Ser Pro Arg Glu Gln Arg Trp Ala Pro Ala
    450                 455                 460

Gly Thr His Phe His Gln Phe Val Val Pro Pro Ile Ile Gly Phe Arg
465                 470                 475                 480

Arg Asp Cys Thr Tyr Gly Lys Leu Ala Ala Met Arg Leu Pro Glu Asp
                485                 490                 495

Val Glu Gly Leu Gly Thr Cys Glu Tyr Thr Met Gly Arg Gly Val Val
            500                 505                 510

His Ala Cys His Ala Gly Gly Val Val His Phe Leu Glu Gly Trp Asp
        515                 520                 525

His His Glu Val Gly Ala Ile Asp Val Asp Arg Ile Asp Ala Val Trp
    530                 535                 540

Asn Ala Ala Leu Arg His Gly Leu Thr Pro Ala
545                 550                 555
```

The Arabidopsis-derived EST, believed to be a glossy1 homolog based on preliminary sequencing, was obtained and sequenced in its entirety using standard methods. The nucleic acid and deduced amino acid sequences follow:

```
ACGGTATA ATG GCC ACA AAA CCA GGA GTC CTC ACC GAT TGG CCT TGG ACA      50 [SEQ ID NO:17]

CCC CTC GGA AGT TTC AAG TAC ATC GTA ATA GCA CCA TGG GCT GTC CAT      98

AGC ACA TAC AGG TTT GTG ACA GAT GAT CCA GAG AAG AGG GAT CTC GGG     146

TAC TTC CTT GTG TTC CCC TTC TTG CTC TTC AGA ATT CTG CAC AAC CAG     194

GTT TGG ATC TCT CTG TCC CGT TAC TAT ACG TCC TCG GGA AAG AGA CGC     242
```

-continued

```
ATC GTC GAC AAG GGA ATC GAC TTC AAT CAG GTC GAC AGG GAG ACC AAC        290
TGG GAT GAC CAA ATA TTG TTC AAC GGA GTG CTG TTC TAT ATA GGC ATC        338
AAC CTA TTG GCG GAG GGC AAA CAA CTT CCC TGG TGG AGA ACT GAG GGA        386
GTG TTG ATG GGA GCG CTT ATT CAC ACC GGA CCG GTG GAG TTC CTC TAT        434
TAT TGG GTC CAC AAA GCT CTC CAC CAT CAC TTT CTT TAT TCC CGC TAC        482
CAT TCC CAC CAC CAC TCC TCT ATC GTC ACT GAG CCC ATC ACT TCG GTG        530
ATA CAT CCG TTT GCG GAG CAC ATA GCA TAC TTC ATC CTC TTC GCG ATA        578
CCA CTA CTT ACC ACG TTG GTA ACA AAA ACG GCG TCA ATA ATT TCG TTC        626
GCC GGA TAC ATA ATC TAC ATA GAC TTC ATG AAC AAC ATG GGA CAC TGC        674
AAC TTC GAG CTA ATC CCT AAG CGC CTT TTC CAC CTC TTT CCT CCC CTC        722
AAG TTC CTC TGT TAC ACC CCC TCA TAC CAC TCG CTG CAC CAC ACG CAG        770
TTC CGG ACC AAC TAC TCC CTC TTC ATG CCC TTG TAT GAC TAC ATC TAC        818
GGC ACA ATG GAT GAA AGC ACG GAT ACG TTG TAC GAG AAA ACT CTA GAA        866
AGA GGA GAT GAT AGA GTG GAC GTG GTG CAC TTA ACT CAC CTG ACG ACG        914
CCA GAA TCC ATA TAC CAT TTG CGC ATT GGC TTG CCC TCA TTT GCC TCC        962
TAC CCC TTC GCT TAT AGA TGG TTC ATG CGC CTT TTG TGG CCT TTC ACC       1010
TCT CTC TCC ATG ATA TTC ACG CTC TTC TAC GCC CGC CTC TTT GTC GCT       1058
GAG AGA AAC TCC TTC AAC AAG CTC AAC TTG CAG TCT TGG GTG ATA CCT       1106
AGA TAT AAT CTA CAG TAC TTG TTA AAA TGG AGG AAA GAA GCG ATC AAT       1154
AAC ATG ATT GAG AAA GCG ATA CTG GAG GCA GAT AAG AAA GGA GTG AAG       1202
GTG CTT AGT CTG GGT CTC ATG AAC CAA GGG GAG GAG CTT AAC AGG AAC       1250
GGA GAG GTG TAT ATC CAC AAC CAT CCA GAT ATG AAA GTG AGA CTG GTC       1298
GAC GGC AGT AGA TTA GCA GCA GCT GTT GTG ATC AAC AGT GTA CCC AAA       1346
GCA ACT ACA AGC GTC GTG ATG ACA GGC AAT CTC ACT AAG GTT GCC TAC       1394
ACC ATC GCC TCT GCT CTC TGC CAG AGA GGC GTT CAG GTC TCC ACT CTG       1442
CGC CTA GAC GAG TAT GAG AAA ATA AGA TCA TGC GTT CCA CAA GAA TGC       1490
AGA GAC CAT TTG GTC TAT TTA ACC TCT GAA GCA CTC TCA TCA AAC AAG       1538
GTA TGG CTG GTG GGA GAA GGA ACA ACA AGA GAA GAG CAG GAA AAA GCC       1586
ACA AAA GGG ACA TTG TTT ATA CCA TTC TCA CAG TTC CCC CTC AAG CAG       1634
TTA CGT AGC GAT TGT ATC TAT CAT ACC ACA CCA GCA TTG ATA GTT CCA       1682
AAA TCT CTG GTG AAT GTC CAC TCC TGT GAG AAC TGG TTA CCG AGA AAG       1730
GCG ATG AGT GCA ACT AGA GTG GCC GGC ATA TTG CAC GCC TTA GAA GGA       1778
TGG GAA ACG CAT GAG TGT GGC ACA TCC CTT CTT CTC TCG GAT TTG GAC       1826
AAA GTA TGG GAA GCC TGT CTC AGC CAC GGC TTC CAG CCT CTC CTC CTT       1874
CCA CAT CAT TAAACTCCA ACCTTGGAAG ATTTTTGGAG AATGAGAGCG              1923
ACACGCTCTG TGCTTCTTTT CCTTATGATC CAGCTCTTCC ACGCACACAT GAACTATGAA   1983
ACATATATAA AGCGCACACA TTTTATGTTT TACGCACACA TATATTTATG CATATCAAGC   2043
TTTTGGTGAT TATGGTATTG ATAGAGTCAA ATTAAGCTCG GTGACTATGG TATTAATAAG   2103
AGTACTATTT CCTTAAAAAA AAAAAAAAAA AA                                 2135
Met Ala Thr Lys Pro Gly Val Leu Thr Asp Trp Pro Trp Thr Pro Leu      [SEQ ID NO:18]
1               5                  10                  15
```

-continued

```
Gly Ser Phe Lys Tyr Ile Val Ile Ala Pro Trp Ala Val His Ser Thr
             20                  25                  30

Tyr Arg Phe Val Thr Asp Asp Pro Glu Lys Arg Asp Leu Gly Tyr Phe
         35                  40                  45

Leu Val Phe Pro Phe Leu Leu Phe Arg Ile Leu His Asn Gln Val Trp
     50                  55                  60

Ile Ser Leu Ser Arg Tyr Tyr Thr Ser Ser Gly Lys Arg Arg Ile Val
 65                  70                  75                  80

Asp Lys Gly Ile Asp Phe Asn Gln Val Asp Arg Glu Thr Asn Trp Asp
                 85                  90                  95

Asp Gln Ile Leu Phe Asn Gln Val Leu Phe tyr Ile Gly Ile Asn Leu
             100                 105                 115

Leu Ala Glu Gly Lys Gln Leu Pro Trp Trp Arg Thr Asp Gly Val Leu
         115                 120                 125

Met Gly Ala Leu Ile His Thr Gly Pro Val Glu Phe Leu Tyr Tyr Trp
     130                 135                 140

Val His Lys Ala Leu His His Phe Leu Tyr Ser Arg Tyr His Ser
 145                 150                 155                 160

His His His Ser Ser Ile Val Thr Glu Pro Ile Thr Ser Val Ile His
                 165                 170                 175

Pro Phe Ala Glu His Ile Ala Tyr Phe Ile Leu Phe Ala Ile Pro Leu
             180                 185                 190

Leu Thr Thr Leu Val Thr Lys Thr Ala Ser Ile Ile Ser Phe Ala Gly
         195                 200                 205

Tyr Ile Ile Tyr Ile Asp Phe Met Asn Asn Met Gly His Cys Asn Phe
     210                 215                 220

Glu Leu Ile Pro Lys Arg Leu Phe His Leu Phe Pro Pro Leu Lys Phe
 225                 230                 235                 240

Leu Cys Tyr Thr Pro Ser Tyr His Ser Leu His His Thr Gln Phe Arg
                 245                 250                 255

Thr Asn Tyr Ser Leu Phe Met Pro Leu Tyr Asp Tyr Ile Tyr Gly Thr
             260                 265                 270

Met Asp Glu Ser Thr Asp Thr Leu Tyr Glu Lys Thr Leu Glu Arg Gly
         275                 280                 285

Asp Asp Arg Val Asp Val Val His Leu Thr His Leu Thr Thr Pro Glu
     290                 295                 300

Ser Ile Tyr His Leu Arg Ile Gly Leu Pro Ser Phe Ala Ser Tyr Pro
 305                 310                 315                 320

Phe Ala Tyr Arg Trp Phe Met Arg Leu Leu Trp Pro Phe Thr Ser Leu
                 325                 330                 335

Ser Met Ile Phe Thr Leu Phe Tyr Ala Arg Leu Phe Val Ala Glu Arg
             340                 345                 350

Asn Ser Phe Asn Lys Leu Asn Leu Gln Ser Trp Val Ile Pro Arg Tyr
         355                 360                 365

Asn Leu Gln Tyr Leu Leu Lys Trp Arg Lys Glu Ala Ile Asn Asn Met
     370                 375                 380

Ile Glu Lys Ala Ile Leu Glu Ala Asp Lys Lys Gly Val Lys Val Leu
 385                 390                 395                 400

Ser Leu Gly Leu Met Asn Gln Gly Glu Glu Leu Asn Arg Asn Gly Glu
                 405                 410                 415

Val Tyr Ile His Asn His Pro Asp Met Lys Val Arg Leu Val Asp Gly
             420                 425                 430

Ser Arg Leu Ala Ala Ala Val Val Ile Asn Ser Val Pro Lys Ala Thr
```

```
                                            -continued
                435                 440                 445

Thr Ser Val Val Met Thr Gly Asn Leu Thr Lys Val Ala Tyr Thr Ile
        450                 455                 460

Ala Ser Ala Leu Cys Gln Arg Gly Val Gln Val Ser Thr Leu Arg Leu
    465                 470                 475                 480

Asp Glu Tyr Glu Lys Ile Arg Ser Cys Val Pro Gln GLu Cys Arg Asp
                    485                 490                 495

His Leu Val Tyr Leu Thr Ser Glu Ala Leu Ser Ser Asn Lys Val Trp
                    500                 505                 510

Leu Val Gly Glu Gly Thr Thr Arg Glu Glu Gln Glu Lys Ala Thr Lys
            515                 520                 525

Gly Thr Leu Phe Ile Pro Phe Ser Gln Phe Pro Leu Lys Gln Leu Arg
            530                 535                 540

Ser Asp Cys Ile Tyr His Thr Thr Pro Ala Leu Ile Val Pro Lys Ser
    545                 550                 555                 560

Leu Val Asn Val His Ser Cys Glu Asn Trp Leu Pro Arg Lys Ala Met
                    565                 570                 575

Ser Ala Thr Arg Val Ala Gly Ile Leu His Ala Leu Glu Gly Trp Glu
                580                 585                 590

Thr His Glu Cys Gly Thr Ser Leu Leu Leu Ser Asp Leu Asp Lys Val
            595                 600                 605

Trp Glu Ala Cys Leu Ser His Gly Phe Gln Pro Leu Leu Leu Pro His
        610                 615                 620

His
    625
```

Accordingly, using standard computer search methods of a sequence databank, related or homologous nucleic acids and polypeptides, which had been previously described with respect to sequence only, were correlated to gl1. It is of interest to note that, but for the results disclosed herein, the identified homologs had no known function.

EXAMPLE 6

This example sets forth the procedures used to clone the CER2 locus of Arabidopsis.

Figure 3:
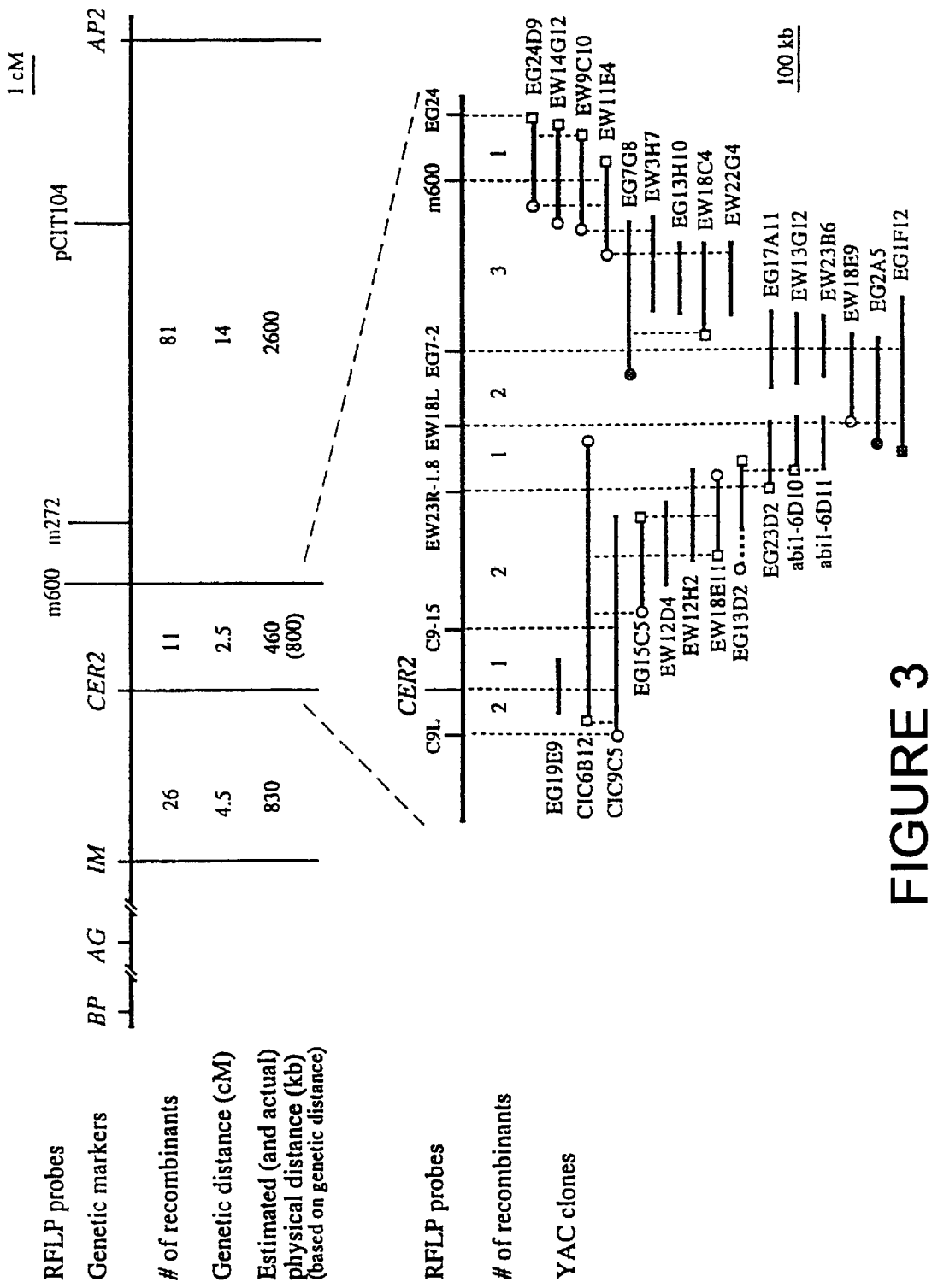
FIG. 3 is a partial genetic map of Arabidopsis as it correlates to a physical map for the region between the cer2 and 600 genetic markers. This figure further provides the relative positions of certain RFLP probes in this region and the identification of YACs that cover this region, all of which were used to accomplish a chromosome walk to the CER2 locus.

The CER2 locus was cloned using a standard method of genetic engineering called "chromosome walking," using the method of Bender et al., supra. This method requires the availability of known genetic markers of the subject organism, here Arabidopsis, which are shown in FIG. 3. As can be seen in FIG. 3, chromosome 4 has known RFLP and visible genetic markers in the region that includes CER2, which is situated between the visible markers IM and AP2 (Koorneef, in *Genetic Maps* (S. J. O'Brien, ed., Cold Spring Harbor Laboratory Press, Cold Spring Harbor, N.Y., 1987), pp. 742–745); estimated genetic and physical distances are recited thereon as well. In the conduct of the present work, recombinants having crossover events noted between the recited markers were identified, the numbers of which are recited in the figure. The genetic distances are estimated based on a subset of the recombinants.

As a first step in cloning the CER2 locus via chromosome walking, F3 families segregating for the genetic markers AG, IM, CER2, and AP2 were screened for genetic recombinants, as follows: A Landsberg erecta (Ler) genetic marker line that carries the recessive markers BREVIPEDI-CELLUS (BP), ECERIFERUM2 (CER2), and APETALA2 (AP2) (Koorneef, supra) was crossed to a Columbia stock that carries the mutant IMMUTANS (IM) (Wetzel et al., *Plant J.*, 6, 161–175 (1994)). The resulting F1 plants were allowed to self-pollinate, and were grown at 23° C., under 16 hours of daylight and 8 hours of dark (same growing conditions used for all of the plants). Individual F3 families were scored for recombinant phenotypes, using the aforementioned markers, which are readily recognized by ordinary artisans. CAPS mapping using primers based on the AGAMOUS (AG) sequence (see Konieczny et al., *Plant J.*, 4, 403–410 (1993) for primer sequences and conditions for assay) was used in some instances to score F2 plants and thereby identify recombinants with break points between AG and CER2. The selected F2 plants were allowed to self-pollinate. Analysis of the resulting F3 families provided genotypic data for the IM locus. The cer2-2 mutant allele (Stock #CS8) was generated via EMS mutagenesis of the Ler ecotype (Koorneef et al., supra) and was obtained from the Arabidopsis Biological Resource Center at Ohio State University, Columbus, Ohio.

To more precisely map the locations of these recombination breakpoints, plants carrying these recombinant chromosomes were analyzed with several RFLP markers. Of the 92 recombinants between CER2 and AP2, 11 occurred between CER2 and m600. Based on these results, the RFLP marker m600 is approximately 2.5 centiMorgans (cM) from CER2. Assuming a value of 185 kilobases (kb) per cM for Arabidopsis chromosome 4 (Schmidt et al., *Science*, 270, 480–483 (1995)), this interval is estimated to be approximately 460 kb.

For the RFLP and other analyses and procedures used in the identification and elucidation of the present invention, a variety of standard nucleic acid chemical techniques were applied. For example, Arabidopsis DNA was isolated from 20–30 day old plants using a modified CTAB procedure, as disclosed in Saghai-Marroof et al. (*Proc. Natl. Acad. Sci. USA*, 81, 8014–8018 (1984)). Digestions with restriction endonucleases were conducted according to manufacturers' specifications. For Southern blot analysis, 0.5 μg aliquots of digested genomic DNA were loaded per lane and subjected to electrophoresis through an agarose gel. RNA was isolated from the aerial parts of soil-grown adult plants, including leaves, stems, young siliques, and inflorescences, using the method of Dean et al. (*EMBO J.*, 4, 3055–3061 (1985)). Poly A-enriched RNA was isolated using PolyATract mRNA Isolation System III™ (Promega, Madison, Wis.). For Northern blot analysis, 15 μg RNA and/or 150 ng poly A-enriched RNA aliquots were loaded per lane and subjected to electrophoresis. Probe preparation, electrophoresis, gel blotting, and hybridizations were conducted according to standard procedures (Sambrook et al., supra).

Four clones (namely, EG24D9, EW14G12, EW9C10, and EW11E4; shown in FIG. 3) that contain sequences homologous to m600 were identified by screening a number of Arabidopsis YAC libraries, namely the EG1, EW, ABI-1, and CIC YAC libraries (Grill et al., *Mol. Gen. Genet.*, 226, 484–490 (1991); Ward et al., *Plant Mol. Biol.*, 14, 561–568 (1990); and Creusot et al., *Plant J.*, 8, 763–770 (1995)), using the method of Gibson et al., supra. Yeast chromosomes were separated as described in Ausubel et al., *Current Protocols in Molecular Biology* (John Wiley & Sons, Inc., 1994). The YAC DNA from agarose slices was purified by electroelution (Sambrook et al., supra) or using the GeneClean™ Kit (BIO 101, Inc., Vista, Calif.). Both ends of these YACS were subcloned via either plasmid rescue, as described in Burke et al., supra, or lambda subcloning. For lambda subcloning, the recovered YAC DNA was digested using the restriction enzyme HindIII and ligated to the lambda insertion vector NM1149 (Murray, supra) and in vitro packaged using Gigapack®II (Stratagene, La Jolla, Calif.). To isolate the subclones containing the YAC ends, the resulting lambda subclone libraries were screened using DNA fragments of pYAC4 flanking the cloning site as centromeric (i.e., the 0.5 kb HindIII/EcoRI fragment) and VRA3-containing end (i.e., the 3 kb HindITl/EcoRI fragment) specific probes, following standard procedures (Sambrook et al., supra).

The identified YACS were oriented relative to the genetic map and each other by using the subcloned YAC ends as RFLF markers to analyze the collection of genetic recombinants and in cross-hybridization experiments involving the other YACS. The YAC end closer to the CER2 locus was then used to isolate another set of YACS closer to the CER2 locus. This cycle was repeated seven times, the results of which are depicted in FIG. 3, for the blown-up area between CER2 and m600. In FIG. 3, the open circles and squares represent the left ends and right ends of the YACS, respectively. The shaded circles and squares indicate YAC ends having repetitive sequences. The dashed line of YAC clones represents a chimeric YAC clone.

YAC CIC9C5 was subcloned into the lambda insertion vector NM1149 as HindIII fragments of up to 8.5 kb in size. The resulting DNA fragments were used as RFLP markers, using the methods just discussed, to analyze recombinants. These analyses established that two of the 26 recombinants between IM and CER2 have recombination breakpoints between marker C9L (the centromeric end of YAC CIC9C5) and CER2. Similarly, one of the 11 recombinants between CER2 and m600 has a breakpoint between CER2 and marker C9-15, which lies approximately 150 kb from the centrometric end of CIC9C5. The CER2 locus is, therefore, located within an approximately 150 kb interval of YAC CIC9C5. The ends of this interval are defined by the positions of markers C9L and C9-15 on YAC CIC9C5.

To more precisely define the chromosomal region that contains the CER2 gene, DNA fragments from the interval defined by the probes C9L and C9-15 were tested for their ability to complement the cer2 mutation. A lambda genomic library prepared with DNA from wild-type Arabidopsis ecotype Landsberg erecta (Ler) (Voytas et al., *Genetics*, 126, 713–721 (1990)) was screened using standard procedures (Sambrook et al., supra) and the subcloned DNA fragments contained within the CIC9C5 interval. The inserts of the lambda genomic clones were subcloned into the binary vector pBI121 as overlapping fragments and used to transform Arabidopsis plants homozygous for the cer2-2 allele. Initially, the complementation test was performed using an Agrobacterium-mediated Arabidopsis root explant transformation system, described by Huang et al. (*Plant Mol. Bio. Reporter*, 10, 372–383 (1992)). Although transgenic plants were obtained, the resulting plants seldom initiated roots and cuticular wax deposition was noted to be strongly influenced by tissue culture conditions. Thus, the CER2 phenotype was not easily scored on the resulting regenerated plants. An in planta transformation procedure according to Bechtold et al. (*C.R. Acad. Sci. Paris, Life Sciences*, 316, 1194–1199 (1993)) was used to successfully generate transgenic seed at a rate of approximately one in 150 seeds.

Two small overlapping genomic fragments (pG1H and pG1RSc) isolated from the lambda genomic clone G1 (illustrated in FIG. 4A) have been shown to complement the cer2-2 mutant phenotype. Eight out of 10 transgenic plants carrying pG1H and 8 out of 9 transgenic plants carrying pG1RSc exhibited a phenotype indistinguishable from the wild type plant, as examined by the unaided eye.

Figures 4A, 4B, 4C:
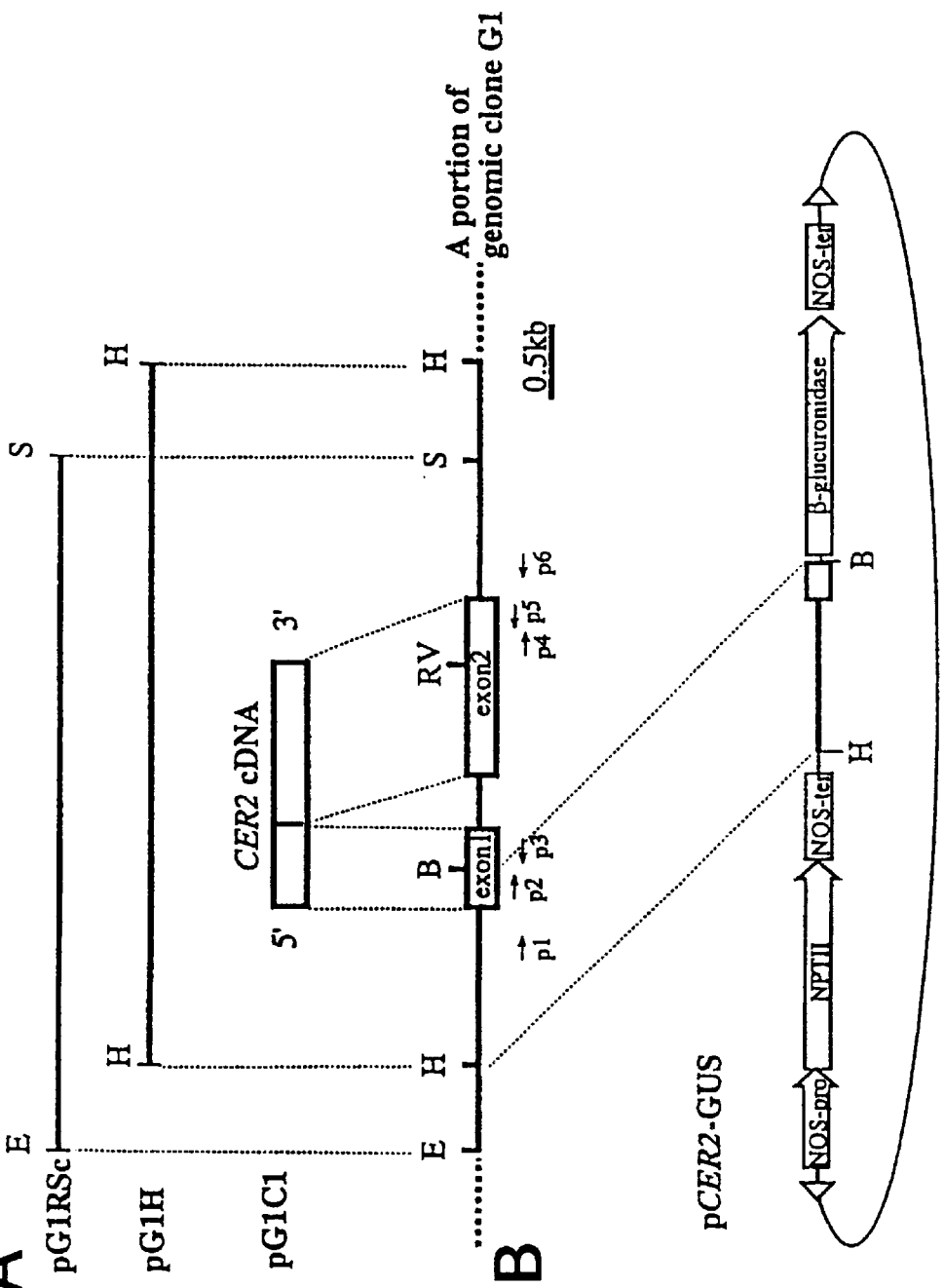
FIGS. 4A, 4B, and 4C are diagrammatic drawings of CER2-containing clones.

One of the genomic DNA fragments capable of complementing the mutant phenotype, pG1H, was partially sequenced using standard methods, and was reported to GenBank (GenBank Accession #U40894). One end of pG1H contains the 3' half of the ATR1 gene, which encodes an NADPH-cytochrome P450 reductase GenBank Accession #X66016). Adjacent to the ATR1 gene is a sequence with near-identity to the Arabidopsis EST 154C7T7 (GenBank Accession #T76511). This 1.4-kb cDNA (EST 154C7T7) was obtained from the Arabidopsis Biological Resource Center and subcloned into pbI121, such that its transcription is under the control of the CaMV 35S promoter (FIG. 4A). The resulting construct (pG1C1) was transformed into plants homozygous for the cer2-2 allele and was found to be sufficient to complement the cer2 mutant phenotype. The EST 154C7T7, therefore, includes the CER2 coding region, or a portion thereof.

Cuticular wax crystals on stems of wild-type, mutant, and transgenic plants were examined via scanning electronic microscopy (SEM). SEM examination of stem cuticular wax crystals was conducted at the Iowa State University Microscopy Facility. The samples were frozen in liquid nitrogen using EM Scope SP2000A cryo-system, coated with gold, and observed using Joel JSM-35 scanning electron microscope at 15 kv. Samples from two Ler wild type plants, one each of the cer2-2 mutant plant, the transgenic plant harboring pG1H and pG1RSc, and two transgenic plants harboring pG1C1 were examined. The SEM results demonstrated that wild-type plants produce a large number of condensed tube-shaped wax crystals. In contrast, mutant plants produce relatively few crystals. Four transgenic plants carrying a CER2 genomic fragment (the pG1H or PG1RSc constructs, FIG. 4A) or constitutively expressing the CER2 cDNA (construct pG1C1, FIG. 4A) produced wax crystals in numbers similar to those on wild-type plants. Although the crystals present on the plant carrying the pG1H construct differed somewhat in shape from those present on wild-type plants, in the remaining three instances, the shape of the wax crystals was similar to wild-type. Accordingly, the CER2 locus was identified and substantially characterized at the level of identifiable portions of the Arabidopsis genome, and such portions were shown capable of reversing the effect of a known mutation at the CER2 locus.

EXAMPLE 7

This example sets forth the sequence identified for the insert of a CER2 cDNA, the corresponding genomic DNA, and a CER2-containing region of pG1H, as well as further characterization of these CER2 sequences.

The CER2 genomic clone G1 was subcloned into PBKS+ and pBKS+ (Stratagene, La Jolla, Calif.). The cDNA clone was subcloned into pGem3fz(+) (Promega, Madison, Wis.). PCR-amplified fragments were purified by electroelution (Sambrook et al., 1989) and directly sequenced. DNA sequencing was performed at the Iowa State University Nucleic Acid Facility using the double-stranded dye terminator technique on an ABI 373 Automated DNA Sequencer (Applied Biosystems, Foster City, Calif.). Both DNA strands were sequenced. Sequence comparisons and analyses were performed using the GCG sequence analysis software package (Version 8, 1994, Genetics Computer Group, Inc., Madison, Wis.) and the PSORT, TMpred, Blast, FASTA algorithms, as described previously (Nakai et al., *Genomics*, 14, 897–911 (1992); Hofmann et al., *Biol. Chem.*, 374, 166 (1993); Altschul et al., *J. Mol. Biol.*, 215, 403–410 (1990); and Pearson et al., *Proc. Natl. Acad. Sci. USA*, 85, 2444–2448 (1988)).

The sequence of the CER2 cDNA insert was:

```
   1 CACAAAAATA AAATGGAGGG AAGCCCAGTG ACCAGTGTCA GGCTCTCTTC[SEQ ID NO:19]

51 GGTGGTGCCT GCTTCTGTGG TAGGTGAGAA CAAGCCACGA CAGCTCACAC

101 CCATGGACTT AGCCATGAAG CTCCACTACG TCCGAGCCGT CTACTTCTTC

151 AAGGGTGCAC GTGACTTCAC TGTCGCCGAC GTGAAGAACA CCATGTTTAC

201 TCTACAGTCT CTACTCCAAT CTTATCACCA CGTCTCAGGT CGGATCCGGA

251 TGTCCGACAA CGACAACGAC ACTTCAGCTG CAGcCATACC TTACATTCGC

301 TGCAACGACA GTGGCATACG CGTGGTCGAG GCCAACGTCG AAGAGTTCAC

351 AGTGGAGAAG TGGCTCGAGT TGGACGACCG TTCCATTGAC CACCGATTCC

401 TTGTCTACGA TCACGTTCTT GGTCCTGATC TTACCTTCTC GCCACTCGTT

451 TTCCTCCAGA TAACTCAGTT TAAATGTGGT GGGCTCTGTA TTAAATTGAG

501 TTGGGCCCAT ATTCTTGGAG ACGTGTTTTC AGCATCAACG TTCATGAAAA

551 CACTTGGACA GCTGGTATCG GGTCATGCCC CAACAAAACC GGTTTACCCG

601 AAAACCCCCG AACTAACCTC TCATGCTCGT AATGATGGTG AAGCTATTTC

651 CATTGAAAAG ATAGATTCGG TTGGCGAGTA TTGGTTACTT ACCAATAAAT

701 GCAAGATGGG GAGACACATT TTTAATTTTA GCCTCAACCA CATTGATAGC

751 TTGATGGCCA AGTACACCAC GCGAGACCAA CCTTTCTCGG AGGTTGATAT

801 TTTGTATGCA TTGATATGGA AGTCGCTACT GAATATCCGC GGCGAAACAA

851 ACACGAATGT TATAACAATT TGTGACCGTA AAAAGTCTTC AACCTGTTGG

901 AACGAGGACT TGGTAATAAG CGTAGTGGAA AAGAATGACG AAATGGTTGG

951 GATATCCGAA CTAgCTGCAC TGATTGCTGG TGAAAAAAGA GAAGAAaACG

1001 GTGCGATCAA GAGGATGATA GAACAAGATA AAGGCTCTTC GGATTTTTTC

1051 ACGTACGGTg CAAATTTAAC GTTTGTGAAT CTTGATGAAA TAGATATGTA

1101 TGAACTTGAG ATCAACGGAG GGAAGCCGGA TTTCGTAAAC TACACGATTC

1151 ATGGGGTCGG AGACAAAGGT GTTGTTTTGG TTTTTCCCAA GCAAAACTTT

1201 GCAAGGATTG TAAGTGTAGT GATGCCTGAA GAAgACCTTG CAAAACTCAA

1251 GGAGGAGGTG ACTAATATGA TTATATAACT TTGTATCTTC TTCTTGTTGT

1301 TATACATAAA TGCTGTTTTT TACTCTTTGT AATTTCATTA TCGAATTGTT

1351 GGGAAgCCTA TCAATAAATT GTTTGAACTG TTTAAAAAAA AAAAAAAAAA

1401 AAAAAAA
```

The corresponding genomic clone for CER2 was found to have the following sequence.

```
           GAGGGCGCAA TTAGGAGTAG ATTGGTTGGC AATAGGGATG TTCTCTACCA[SEQ ID NO:20]
     51 AAAATTTTAC TGTTTTTTCG CAAGATTTAG TTATCGTACA ATTATGTAAA
    101 ATCATTATCA GGAAATTTGT TGCATGATTG TGTTTGAGGT GGAAATGAAC
    151 CGCATCCGTA TTAAGATCAT TTTTGCTGGT GGAAACAATG TTACCAGGAA
    201 ACTGAACTTG GTTTTTTATA GATTAATGTG ACTTGTTAGG TACCGTAATA
    251 TAATACTAGT TGGCTACGAC ACGTACATGT GCGTTTATTG CTTGAAGCCA
    301 ATAAGGACAA GGTGGACGTA ATAAAGTGTG CTTGTTGTTG GATGGATCTG
    351 AATATGATGA CTCAACTGTC CAACTCTAAT GTTGTTGCTA AAGACCCAAA
    401 TCCCACCCAC ATTTAATGTT GCCGTCACGG AAACAGTTTT CCCAACTGTC
    451 CTAAATCAGT GATACCCATG CCTATTCTGA ACTCAACTCT CTTTCGAAAC
    501 TCAATCCTTA TATAACACAT CCCATTTAAG CCTATAAGCT ACACATATCA
    551 GCTCTCTCAC AAAAATAAAA TGGAGGGAAG CCCAGTGACC AGTGTCAGGC
    601 TCTCTTCGGT GGTGCCTGCT TCTGTGGTAG GTGAGAACAA gCCACGACAG
    651 CTCACACCCA TGGACTTAGC CATGAAGCTC CACTACGTCC GAGCCGTCTA
    701 CTTCTTCAAG GGTGCACGTG ACTTCACTGT CGCCGACGTG AAGAACACCA
    751 TGTTTACTCT ACAGTCTCTA CTCCAATCTT ATcaCCACGT CTCAGGTCGG
    801 ATCCGGATGT CCGACAACgA cAACGACACT TCAGCTGCAG CCATACCTTA
    851 CATTCGCTGC AACGACAGTG GCATACGCGT GGTCGAGGCC AACGTCGAAG
    901 AGTTCACAGT GGaGAAGTGG CTCGAGTTGG ACGACCGTTC CATTGACCAC
    951 CGATTCCTTG TCTACGATCA CGTTCTTGGT CCTGATCTTA CCTTCTCGCC
   1001 ACTCGTTTTC CTCCAGGTAA ACACACATAC ACAAATTTTA GTATAATATA
   1051 ATGGATTATT TAAGTTCACA TGCAACGAAA ACGGCTGATT CTCCCACGAA
   1101 CTTAGTTTCT TTCTTAGTTA CTAACTATCA AACATTCGTT TCAAATTCTT
   1151 TCCAATCATT AGCTTAATTA ATAATTATGA AATGAATATT TAATATAACC
   1201 GTGGAACTTG AAGAGAAAAT ATTTTTTACA TGTGAAATTG ATTCTTCACT
   1251 ATATATGATC AGGTTAGATT CTGTGTGTGT GTGTGTGTGT GTTTTTTTTT
   1301 TGTCCAAATC AGGCTAGCTA GAGTAAACTA AATTTTTTAC TTTGAAATTC
   1351 GTTTTTCAGA TAACTCAGTT TAAATGTGGT GGGCTCTGTA TTGGGTTGAG
   1410 TTGGGCCCAT ATTCTTGGAG ACGTGTTTTC AGCATCAACG TTCATGAAAA
   1451 CACTTGGACA GCTGGTATCG GGTCATGCCC CAACAAAACC GGTTTACCCG
   1501 AAAACCCCCG AACTAACCTC TCATGCTCGT AATGATGGTG AAGCTATTTC
   1551 CATTGAAAAG ATAGATTCGG TTGGCGAGTA TTGGTTACTT ACCAATAAAT
   1601 GCAAGATGGG GAGACACATT TTTAATTTTA GCCTCAACCA CATTGATAGC
   1651 TTGATGGCCA AGTACACCAC GCGAGACCAA CCTTTCTCGG AGGTTGATAT
   1701 TTTGTATGCA TTGATATGGA AGTCGCTACT GAATATCCGC GGCGAAACAA
   1751 ACACGAATGT TATAACAATT TGTGACCGTA AAAAGTCTTC AACCTGTTGG
   1801 AACGAGGACT TGGTAATAAG CGTAGTGGAA AAGAATGACG AAATGGTTGG
   1851 GATATCCGAA CTAgCTGCAC TGATTGCTGG TGAAAAAAGA GAAGAAaaCG
```

```
-continued
1901 GTgCGATCAA GAGGATGATA GAACAAGATA AAGGCTCTTC GGATTTTTTC

1951 ACGTACGGTG CAAATTTAAC GTTTGTGAAT CTTGATGAAA TAGATATGTA

2001 TGAACTTGAG ATCAACGGAG GGAAGCCGGA TTTCGTAAAC TACACGATTC

2051 ATGGGGTCGG AGATAAAGGT GTTGTTTTGG TTTTTCCCAA GCAAAACTTT

2101 GCAAGGATTG TAAGTGTAGT GATGCCTGAA GAAGACCTTG CAAAACTCAA

2151 GGAGGAGGTG ACTAATATGA TTATATAACT TTGTATCTTC TTCTTGTTGT

2201 TATACATAAA TGCTGTTTTT TACTCTTTGT AATTTCATTA TCGAATTGTT

2251 GGGAAGCCTA TCAATAAATT GTTTGAACTG TTTACTTTTC CTGTCGCTTT

2301 ATTATTGCGT CACACCATCC AAAGTTTACA ATGTGGACTC TTATATTTTC

2351 TACTCCGTAA AATCAACTTT AGAGCTATCA AGATTGGATC ATTTGCATGG

2401 GATTTGGAGT GAAAAGATAA ATTGTTCTTG TTTGGTGTCA CTGATTCACA

2451 ATGATGATCC ACTATCGACA GTAGAAAGCA TGATGATGAA ATCTTGGGTA

2501 TCTTCTCTCA ATTTTATCAC TCTCACAGAT TTATTTTGT
```

As noted in Example 6, an Arabidopsis EST labeled 154C7T7 was also identified as having a homologous sequence to that of CER2. To provide additional evidence that this clone represents a new full-length cDNA, the region of pG1H that includes the CER2 coding region was sequenced as follows:

```
ATAAGGACAA GGTGGACGTA ATAAAGTGTG CTTGTTGTTG GATGGATCTG AATATGATGA        60 [SEQ ID NO:22]

CTCAACTGTC CAACTCTAAT GTTGTTGCTA AAGACCCAAA TCCCACCCAC ATTTAATGTT       120

GCCGTCACGG AAACAGTTTT CCCAACTGTC CTAAATCAGT GATACCCATG CCTATTCTGA       180

ACTCAACTCT CTTTCGAAAC TCAATCCTTA TATAACACAT CCCATTTAAG CCTATAAGCT       240

ACACATATCA GCTCTCTCAC AAAAATAAA ATG GAG GGA AGC CCA GTG ACC AGT        293
                                  Met Glu Gly Ser Pro Val Thr Ser
                                   1               5

GTC AGG CTC TCT TCG GTG GTG CCT GCT TCT GTG GTA GGT GAG AAC AAG        341
Val Arg Leu Ser Ser Val Val Pro Ala Ser Val Val Gly Glu Asn Lys
     10              15                  20

CCA CGA CAG CTC ACA CCC ATG GAC TTA GCC ATG AAG CTC CAC TAC GTC        389
Pro Arg Gln Leu Thr Pro Met Asp Leu Ala Met Lys Leu His Tyr Val
 25              30                  35                  40

CGA GCC GTC TAC TTC TTC AAG GGT GCA CGT GAC TTC ACT GTC GCC GAC        437
Arg Ala Val Tyr Phe Phe Lys Gly Ala Arg Asp Phe Thr Val Ala Asp
             45                  50                  55

GTG AAG AAC ACC ATG TTT ACT CTA CAG TCT CTA CTC CAA TCT TAT CAC        485
Val Lys Asn Thr Met Phe Thr Leu Gln Ser Leu Leu Gln Ser Tyr His
                 60                  65                  70

CAC GTC TCA GGT CGG ATC CGG ATG TCC GAC AAC GAC AAC GAC ACT TCA        533
His Val Ser Gly Arg Ile Arg Met Ser Asp Asn Asp Asn Asp Thr Ser
             75                  80                  85

GCT GCA GCC ATA CCT TAC ATT CGC TGC AAC GAC AGT GGC ATA CGC GTG        581
Ala Ala Ala Ile Pro Tyr Ile Arg Cys Asn Asp Ser Gly Ile Arg Val
         90                  95                 100

GTC GAG GCC AAC GTC GAA GAG TTC ACA GTG GAG AAG TGG CTC GAG TTG        629
Val Glu Ala Asn Val Glu Glu Phe Thr Val Glu Lys Trp Leu Glu Leu
        105                 110                 115                 120

GAC GAC CGT TCC ATT GAC CAC CGA TTC CTT GTC TAC GAT CAC GTT CTT        677
Asp Asp Arg Ser Ile Asp His Arg Phe Leu Val Tyr Asp His Val Leu
                125                 130                 135

GGT CCT GAT CTT ACC TTC TCG CCA CTC GTT TTC CTC CAG GTAAACACAC        726
Gly Pro Asp Leu Thr Phe Ser Pro Leu Val Phe Leu Gln
```

-continued

```
         140             145
ATACACAAAT TTTAGTATAA TATAATGGAT TATTTAAGTT CACATGCAAC GAAAACGGCT       786 [SEQ ID NO:23]

GATTCTCCCA CGAACTTAGT TTCTTTCTTA GTTACTAACT ATCAAACATT CGTTTCAAAT       846

TCTTTCCAAT CATTAGCTTA ATTAATAATT ATGAAATGAA TATTTAATAT AACCGTGGAA       906

CTTGAAGAGA AAATATTTTT TACATGTGAA ATTGATTCTT CACTATATAT GATCAGGTTA       966

GATTCTGTGT GTGTGTGTGT GTGTGTTTTT TTTTTGTCCA AATCAGGCTA GCTAGAGTAA      1026

ACTAAATTTT TTACTTTGAA ATTCGTTTTT CAG ATA ACT CAG TTT AAA TGT GGT      1080
                                    Ile Thr Gln Phe Lys Cys Gly
                                     1               5

GGG CTC TGT ATT GGG TTG AGT TGG GCC CAT ATT CTT GGA GAC GTG TTT        1128
Gly Leu Cys Ile Gly Leu Ser Trp Ala His Ile Leu Gly Asp Val Phe
         10              15              20

TCA GCA TCA ACG TTC ATG AAA ACA CTT GGA CAG CTG GTA TCG GGT CAT        1176
Ser Ala Ser Thr Phe Met Lys Thr Leu Gly Gln Leu Val Ser Gly His
     25              30              35

GCC CCA ACA AAA CCG GTT TAC CCG AAA ACC CCC GAA CTA ACC TCT CAT        1224
Ala Pro Thr Lys Pro Val Tyr pro Lys Thr Pro Glu Leu Thr Ser His
40              45              50              55

GCT CGT AAT GAT GGT GAA GCT ATT TCC ATT GAA AAG ATA GAT TCG GTT        1272
Ala Arg Asn Asp Gly Glu Ala Ile Ser Ile Glu Lys Ile Asp Ser Val
             60              65              70

GGC GAG TAT TGG TTA CTT ACC AAT AAA TGC AAG ATG GGG AGA CAC ATT        1320
Glu Glu Tyr Trp Leu Leu Thr Asn Lys Cys Lys Met Gly Arg His Ile
         75              80              85

TTT AAT TTT AGC CTC AAC CAC ATT GAT AGC TTG ATG GCC AAG TAC ACC        1368
Phe Asn Phe Ser Leu Asn His Ile Asp Ser Leu Met Ala Lys Tyr Thr
     90              95              100

ACG CGA GAC CAA CCT TTC TCG GAG GTT GAT ATT TTG TAT GCA TTG ATA        1416
Thr Arg Asp Gln Pro Phe Ser Glu Val Asp Ile Leu Tyr Ala Leu Ile
105             110             115

TGG AAG TCG CTA CTG AAT ATC CGC GGC GAA ACA AAC ACG AAT GTT ATA        1464
Trp Lys Ser Leu Leu Asn Ile Arg Gly Glu Thr Asn Thr Asn Val Ile
120             125             130             135

ACA ATT TGT GAC CGT AAA AAG TCT TCA ACC TGT TGG AAC GAG GAC TTG        1512
Thr Ile Cys Asp Arg Lys Lys Ser Ser Thr Cys Trp Asn Glu Asp Leu
             140             145             150

GTA ATA AGC GTA GTG GAA AAG AAT GAC GAA ATG GTT GGG ATA TCC GAA        1560
Val Ile Ser Val Val Glu Lys Asn Asp Glu Met Val Gly Ile Ser Glu
         155             160             165

CTA GCT GCA CTG ATT GCT GGT GAA AAA AGA GAA GAA AAC GGT GCG ATC        1608
Leu Ala Ala Leu Ile Ala Gly Glu Lys Arg Glu Glu Asn Gly Ala Ile
     170             175             180

AAG AGG ATG ATA GAA CAA GAT AAA GGC TCT TCG GAT TTT TTC ACG TAC        1656
Lys Arg met Ile Glu Gln Asp Lys Gly Ser Ser Asp Phe Phe Thr Tyr
185             190             195

GGT GCA AAT TTA ACG TTT GTG AAT CTT GAT GAA ATA GAT ATG TAT GAA        1704
Gly Ala Asn Leu Thr Phe Val Asn Leu Asp Glu Ile Asp Met Tyr Glu
200             205             210             215

CTT GAG ATC AAC GGA GGG AAG CCG GAT TTC GTA AAC TAC ACG ATT CAT        1752
Leu Glu Ile Asn Gly Gly Lys Pro Asp Phe Val Asn Tyr Thr Ile His
             220             225             230

GGG GTC GGA GAT AAA GGT GTT GTT TTG GTT TTT CCC AAG CAA AAC TTT        1800
Gly Val Gly Asp Lys Gly Val Val Leu Val Phe Pro Lys Gln Asn Phe
         235             240             245

GCA AGG ATT GTA AGT GTA GTG ATG CCT GAA GAA GAC CTT GCA AAA CTC        1848
Ala Arg Ile Val Ser Val Val Met pro Glu Glu Asp Leu Ala Lys Leu
     250             255             260
```

```
                                    -continued
AAG GAG GAG GTG ACT AAT ATG ATT ATA TAACTTTGTA TCTTCTTCTT          1895
Lys Glu Glu Val Thr Asn Met Ile Ile
    265                 270

GTTGTTATAC ATAAATGCTG TTTTTTACTC TTTGTAATTT CATTATCGAA TTGTTGGGAA  1955 [SEQ ID NO:21]

GCCTATCAAT AAATTGTTTG AACTGTTTAC TTTTCCTGTC GCTTTATTAT TGCGTCACAC  2015

CATCCAAAGT TTACAATGTG GACTC                                       2040
```

The DNA sequence of the 1407 nucleotide (nt) EST 154C7T7 disclosed in Example 6 contains a 134 nt 3' untranslated region that includes a putative polyadenylation signal (AATAAA) and a 24-nt poly A tail. The size of this cDNA is indistinguishable from the size of the 1.4-kb transcript detected when it is used as a probe on RNA gel blots (see below). Two putative TATA boxes (TATAAG and TATATA) that exhibit a high degree of similarity to the TATA consensus sequence (Joshi, Nucleic Acid Res., 15, 6643–6653 (1987)) were identified at positions −37 and −61 (relative to the 5' end of the cDNA), respectively. In addition, two putative CAAT boxes were identified at positions −68 and −85. In combination, these data support the view that the EST 145C7T7 cDNA is near full-length. The only sequence polymorphism between the cDNA derived from the Columbia ecotype and the genomic clone derived from the Ler ecotype is a single conservative nucleotide substitution at position +1495.

Figure 5:
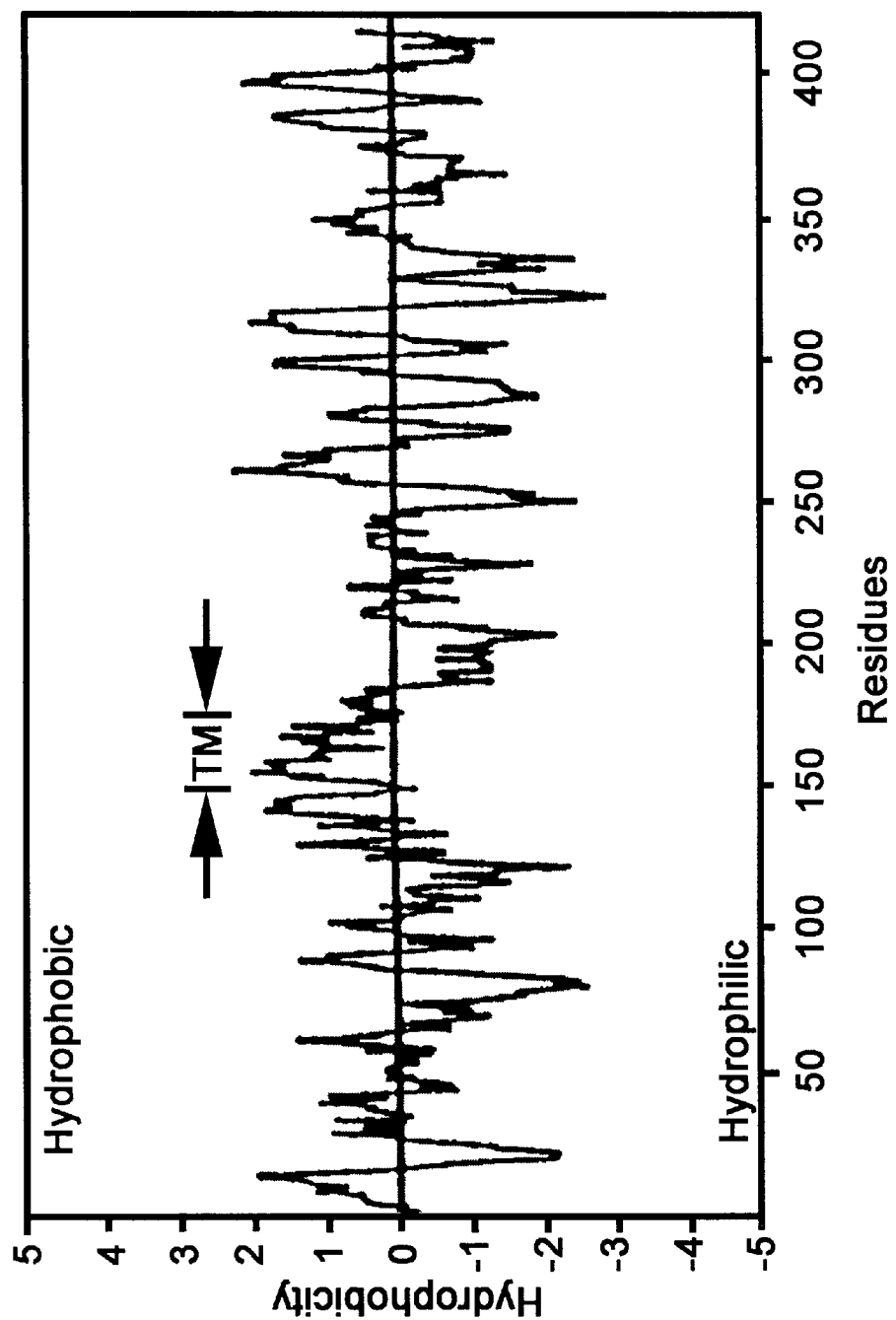
FIG. 5 is a hydrophobicity plot of the deduced CER2 amino acid sequence.

The CER2 cDNA contains an open reading frame that could encode a protein of 421 amino acid residues with a predicted molecular weight of 47 kD. No alternative open reading frames of significant length were identified. Computer-based homology searches using various derivatives of the Blast (Altschul et al., supra) and FASTA (Pearson et al., supra) algorithms have failed to reveal any significant sequence similarities between the deduced CER2 protein and entries in the nonredundant nucleotide and protein databases that have a known biochemical function. However, the deduced CER2 protein exhibits a high level of sequence similarity to that of glossy2 (gl2), a gene that plays an undefined role in cuticular wax biosynthesis in maize (GenBank Accession No. X88779, GI: 949979; SEQ ID NO: 30). The deduced CER2 protein does not contain a recognizable protein targeting signal sequence or a transmembrane domain when analyzed with the PSORT algorithm (Nakai et al., supra). However, the TMpred algorithm (Hofmann and Stoffel (1993)) predicts a putative transmembrane domain (indicated by "TM" in the hydrophobicity plot depicted in FIG. 5) between residues 147 and 172 of the deduced CER2 protein.

CER2-specific PCR primers were used to amplify the CER2-2 mutant allele and the location of respective homologies are represented in FIG. 4B. The primer sequences follow:

p1: 5'-AGGTGGACGTAATAAAGTGTG-3' [SEQ ID NO:24]

p2: 5'-GGTGGTGCCTGCTTCTTTGGTA-3' [SEQ ID NO:25]

p3: 5'-AAATCGAACCACTTCCCCACTG-3' [SEQ ID NO:26]

p4: 5'-GAGGATGATAGAACAAGATAAAGG-3' [SEQ ID NO:27]

p5: 5'-GGCATCACTACACTTACAATCCT-3' [SEQ ID NO:28]

p6: 5'-CAGTGACACCAAACAAGAACAA-3' [SEQ ID NO:29]

The paired primers: p1 and p3, p2 and p5, and p4 and p6 were used to PCR amplify the CER2-2 mutant allele. The primers were synthesized at the Iowa State University Nucleic Acid Facility using a 394 DNA/RNA Synthesizer (Applied Biosystems, Foster City, Calif.). Amplification reactions were conducted in 50 $\mu$l volumes containing 50–100 ng of genomic DNA and 50 mM KCl, 10 mM Tris-HCl, pH 9.0, 0.1% Triton X-100, 1.5 mM MgCl$_2$, 150 $\mu$M dNTP, and 0.5 $\mu$M primers. The reactions were overlaid with 100 $\mu$l of mineral oil and denatured at 94° C. for 1 minute, followed by 30 cycles of denaturation at 94° C. for 45 seconds, annealing at 54° C. (for the pair of p1 and p3) or 58° C. (for the pairs of p2 and p5, p4 and p6) for 45 seconds and extension at 72° C. for 1 to 2 minutes. The reactions were given a final extension at 72° C. for 10 minutes to complete the elongation.

The entire coding region and 300 bp upstream and 100 bp downstream of the CER2-2 gene were sequenced and compared to the sequence of genomic DNA derived from wild-type progenitor (Voytas et al., Genetics, 126, 713–721 (1990)). Based upon this comparison, there is only a single difference between the CER2-2 mutant allele and its wild-type progenitor. This difference is a G to A transition mutation at position +1150 that changes a tryptophan codon to a premature stop codon, resulting in a truncated 295 amino acid peptide. The result therefore further confirms that the identified gene corresponds to the CER2 locus.

The CER2 cDNA was used to hybridize a DNA gel blot containing 500 mg of Ler genomic DNA digested by five different restriction enzymes, namely BglII, EcoRPI, EcoRV, HindIII, and XbaI. Using even relatively low stringency washes (washes in 1×SSC at 65° C. for 40 minutes), a single-copy hybridization pattern was revealed, suggesting that CER2 is a single-copy gene. When this experiment was repeated at even lower stringency (whereby the hybridization was conducted at 45° C. and the final wash was performed with 1×SSC at 45° C.), several weakly hybridizing bonds were revealed, suggesting that some CER2-homologous sequences are present in the Arabidopsis genome.

Accordingly, the CER2-specific sequences have characteristics that are fully consistent with their being the CER2 genes.

EXAMPLE 8

This example sets forth data concerning the accumulation of CER2 mRNA in wild-type and mutant plants, and spatial patterns of expression of the CEP2 gene in a plant.

The CER2 cDNA clone was used as a probe in RNA gel blotting experiments. Total RNA and poly A-enriched RNA were isolated from aerial parts of adult wild-type and mutant plants homozygous for the cer2-2 allele, as discussed in Example 6, and applied to an electrophoretic gel in 15 $\mu$g and 150 ng aliquots, respectively. After the Northern blot was effected, i.e., the RNA was transferred to a solid medium from the electrophoretic gel using standard means, the blot was probed with the cDNA insert of pG1C1. These hybridization experiments revealed a single 1.4-kb mRNA in RNA isolated from a pool of leaves, stems, young siliques, and inflorescences. The amount of steady-state CER2 RNA in the cer2-2 mutant plants is approximately 5 to 10-fold lower than in wild-type plants (lanes labeled WT in FIG. 11).

Based on the phenotype associated with the cer2 mutation, it would be expected that the CER2 mRNA would accumulate in the epidermis of siliques and stems. To test this hypothesis, the 1.243 kb HindIII-BamHI fragment of pG1H that includes positions −1009 to position +234 of the CER2 gene was fused in-frame with the β-glucuronidase reporter gene in the binary vector pB1101.3. The resulting construct (pCER2-GUS; FIG. 8C) was transformed into Arabidopsis Ler ecotype. Samples from six individual transgenic plants (T1) representing at least three independent transformation events were stained for GUS activity with X-Gluc.

Construction of G1H, pG1RSc, pG1C1, and pCER2-GUS, and plant transformation therewith, was accomplished using conventional means, as follows: For the subcloning of pG1H, pG1RSc, and pG1C1, the DNA fragments from the genomic clone G1 and the insert of cDNA clone were inserted into pB1121 (Clontech, Palo Alto, Calif.). To construct pCER2-GUS, the 1.4 kb HindIII/BamHI fragment of pG1H was inserted into the HindIII/BamHI cloning site of pBI101.3 (Clontech, Palo Alto, Calif.), which fragment includes the CER promoter. The resulting plasmids were introduced into Agrobacterium strain C58C1 (Koncz et al., *Mol. Gen. Genet.*, 204, 383–396 (1986)) via freeze/thaw procedure (An et al., in *Plant Molecular Biology Manual*, part A3, pp. 1–9 (Gelvin and Schilperoot, eds., Vilumer Academic Publishers, Vordrecht, 1988)).

Agrobacterium-mediated root explant transformation was conducted according to the procedure of Huang et al., *Plant Mol. Bio. Reporter*, 10, 372–383 (1992). For the in planta transformation, an adaptation of Bechtold et al., *C.R. Acad. Sci. Paris, Life Sciences*, 316, 1194–1199 (1993) was used. The variant aspects with respect to the Bechtol et al. protocol were that seeds harvested from the vacuum infiltration treated plants ($T_0$) in the same pot were bulked. The transgenic plants ($T_1$) from the same bulk were considered to represent at least one independent transformation event.

Histochemical analysis of β-glucuronidase activity in the transformed plants were performed using 5-bromo-4-chloro-3-indolyl-β-D-glucuronic acid, as described by Jefferson, *Plant Mol. Biol Rep.*, 5, 387–405 (1987). The cross-section of the stems was performed by freehand, and then subjected, along with the other structures, to the histochemical procedure.

All six transgenic plants showed similar expression patterns as described below. As expected, the pCER2-GUS chimeric gene is expressed in siliques and stems. However, the most prominent expression occurs in young siliques, and mature ovaries. Only the upper portion of stems stains for GUS activity. Hence, the localization of GUS activity is highest in regions where cells are rapidly expanding. A low level of GUS staining is also apparent in mature anthers. Detailed examination of these stained anthers revealed that only the pollen grains were stained. The expression of the CER2-GUS gene was further examined in cross-sections of GUS-stained stems. GUS activity was detected not only in the epidermal layers, but also in the vascular bundles of stems, siliques, filaments, petals and sepals. Expression of the pCER2-GUS gene was not detected in rosette leaves (before or after bolting) or in cauline leaves. In addition, no expression was detected in sepals or petals, except in the vascular bundles.

Accordingly, CER2 transcription appears correlated in general terms with the phenotype conditioned by the cer2 mutation. The analysis of transgenic plants demonstrated that the CER2-GUS gene is expressed in those portions of stems where cells are expanding, and in the developing siliques. GUS activity was also detectable in anthers, although at lower levels. Because CER2 was found to be expressed in anthers and pollen grains, it is evident that cuticular waxes have a function in pollen development or function. In contrast, the CER2 gene is not likely to be involved in the cuticular wax deposition of leaves, although it appears to be involved in such activity in the cells of the vascular bundle tissues. Thus, the CER2 promoter confers spatial and/or temporal control of expression of its controlled structural gene.

EXAMPLE 9

This example illustrates the utility of probing a plant's genome for identification of related genes using a cloned cuticular lipid gene or fragment thereof.

The polynucleotides described hereinabove have been used as probes to identify the existence of related sequences within heterologous and homologous genomes. Polynucleotides encoding glossy1 and glossy8 were used as probes of maize genomic DNA, using standard methods. In particular, the autoradiogram provided herein as FIG. 12 was generated from a Southern blot of DNA isolated from different maize strains that was digested with restriction endonuclease KpnI and probed with the entire glossy1 cDNA sequence [SEQ ID NOS:10 and 11]. The source of digested DNA in the lanes is listed parenthetically after recital of the label on each lane as follows: 91g138 (i.e., gl1-mu91g138/gl1-ref); 91g139 (i.e., gl1-mu91g139/gl1-ref); 92 3508-1 (i.e., Gl1/gl1-ref); 92 3508-3 (i.e., Gl1/gl1-ref); 92 3058-4 (i.e., Gl1/gl1-ref); 92 3508-5 (i.e., Gl1/gl1-ref); 92 3508-6 (i.e., Gl1/gl1-ref); 92 3508-7 (i.e., Gl1/gl1-ref); 92 3508-8 (i.e., Gl1/gl1-ref); 92 3508-9 (i.e., Gl1/gl1-ref); 92 3508-10 (i.e., Gl1/gl1-ref); 92 1442-3 (i.e., Gl1/gl1-ref); 91g137 (i.e., Gl1-mu91g137/gl1-ref); 92 3507-3 (i.e., Gl1/gl1-ref); 92 3507-5 (i.e., Gl1/gl1-ref); and 92 3507-9 (i.e., Gl1/gl1-ref). The last lane, labeled λH3, contains λ DNA digested with HindIII for size standards.

An autoradiogram was generated from a Southern blot of DNA isolated from different maize strains as well, but digested with restriction endonuclease HindIII and SacI instead, and probed with the 0.8 kb glossy8 cDNA [SEQ ID NO:1].

The probe protocol used for the Southern analysis was as described by Sambrook et al., supra. In particular, the protocol involved taking the Southern blot of the gel in which the various DNAs were separated by size, incubating the blot with labeled probe in 6×SSPE at 68° C., washing free labeled probe in 2×SSPE at 68° C. for 30 minutes, followed by 10 mM Tris for another 30 minutes. The autoradiogram, itself, was exposed for 2 or 3 days at −70° C.

The autoradiograms clearly established that the maize glossy1 and glossy8 probes detect multiple sequences in the maize genome. Accordingly, it is believed that the present invention provides a means for the isolation of other lipid biosynthesis-involved genes, among others.

All of the references cited herein, including patents, patent applications, and technical literature, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of introducing a nucleic acid into a plant cell, which method comprises the steps of:
   (a) inserting into a plant cell (i) a sense nucleic acid, wherein said sense nucleic acid encodes a product of a cuticular lipid gene to be expressed in said plant cell, or (ii) an antisense nucleic acid, wherein said antisense nucleic acid expresses an antisense nucleic acid molecule, which is specific for mRNA or a portion thereof of a cuticular lipid gene present in and expressed in said plant cell, wherein said antisense nucleic acid molecule is of sufficient length to inhibit expression of said cuticular lipid gene,
      wherein said sense or antisense nucleic acid is operatively linked to one or more regulatory sequences, and
      wherein said cuticular lipid gene comprises a sequence selected from the group consisting of SEQ ID NO: 10, SEQ ID NO: 11, SEQ ID NO: 13, SEQ ID NO: 15, SEQ ID NO: 17, SEQ ID NO: 30, SEQ ID NO: 1, SEQ ID NO: 2, SEQ ID NO: 3, SEQ ID NO: 5, SEQ ID NO: 6, SEQ ID NO: 8, SEQ ID NO: 19, SEQ ID NO: 20, SEQ ID NO: 23 and a sequence which hybridizes to any of the aforementioned nucleic acid sequences under stringent conditions;
   (b) expressing said sense or antisense nucleic acid in said plant cell; and
   (c) culturing said plant cell.

2. The method of claim 1, further comprising the step of:
   (d) generating from the plant cell a plant.

3. The method of claim 1, wherein said plant is selected from the group consisting of maize, soybean, rapeseed, canola, cotton, safflower, peanut, palm, and sunflower.

4. The method of claim 1, wherein at least one of said regulatory sequences is developmentally specific or tissue-specific.

5. The method of claim 2, wherein said plant is selected from the group consisting of maize, soybean, rapeseed, canola, cotton, safflower, peanut, palm, and sunflower.

6. The method of claim 5, wherein said plant is maize or canola.

7. A plant cell comprising an exogenous nucleic acid selected from the group consisting of a sense nucleic acid encoding a product of a cuticular lipid gene and an antisense nucleic acid expressing an antisense nucleic acid molecule specific for mRNA or a portion thereof of an endogenous cuticular lipid gene, wherein said antisense nucleic acid molecule is of sufficient length to inhibit expression of said cuticular lipid gene, wherein said exogenous nucleic acid is operatively linked to one or more regulatory sequences and said cuticular lipid gene comprises a sequence selected from the group consisting of SEQ ID NO: 10, SEQ ID NO: 11, SEQ ID NO: 13, SEQ ID NO: 15, SEQ ID NO: 17, SEQ ID NO: 30, SEQ ID NO: 1, SEQ ID NO: 2, SEQ ID NO: 3, SEQ ID NO: 5, SEQ ID NO: 6, SEQ ID NO: 8, SEQ ID NO: 19, SEQ ID NO: 20, SEQ ID NO: 23 and a sequence which hybridizes to any of the aforementioned nucleic acid sequences under stringent conditions.

8. A plant comprising an exogenous nucleic acid selected from the group consisting of a sense nucleic acid encoding a product of a cuticular lipid gene and an antisense nucleic acid expressing an antisense nucleic acid molecule specific for mRNA or a portion thereof of an endogenous cuticular lipid gene, wherein said antisense nucleic acid molecule is of sufficient length to inhibit expression of said cuticular lipid gene, wherein said exogenous nucleic acid is operatively linked to one or more regulatory sequences and said cuticular lipid gene comprises a sequence selected from the group consisting of SEQ ID NO: 10, SEQ ID NO: 11, SEQ ID NO: 13, SEQ ID NO: 15, SEQ ID NO: 17, SEQ ID NO: 30, SEQ ID NO: 1, SEQ ID NO: 2, SEQ ID NO: 3, SEQ ID NO: 5, SEQ ID NO. 6, SEQ ID NO: 8, SEQ ID NO: 19, SEQ ID NO: 20, SEQ ID NO: 23 and a sequence which hybridizes to any of the aforementioned nucleic acid sequences under stringent conditions.

9. The method of claim 1, wherein at least one of said regulatory sequences is a regulatable promoter selected from the group consisting of a temperature-sensitive promoter and a promoter that is inducible by a chemical.

10. The plant cell of claim 7, wherein at least one of said regulatory sequences is developmentally specific or tissue-specific.

11. The plant cell of claim 7, wherein at least one of said regulatory sequences is a regulatable promoter selected from the group consisting of a temperature-sensitive promoter and a promoter that is inducible by a chemical.

12. The plant of claim 8, wherein at least one of said regulatory sequences is developmentally specific or tissue-specific.

13. The plant of claim 8, wherein at least one of said regulatory sequences is a regulatable promoter selected from the group consisting of a temperature-sensitive promoter and a promoter that is inducible by a chemical.

* * * * *

```
                              SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
           (A) LENGTH: 259 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:1:

GAGCTGATGC GCACCCTCAT CCGGGTCAAC GTCGAGGGCG TCACGCGTGT CACGCACGCC      60

GTGCTGCCGG CCATGGTCGA GAGGAAGCGC GGCGCCATTG TCAACATCGG CTCCGGCGCC     120

GCCTCCGTCG TGCCTTCTGA TCCGCTCTAC TCCGTCTACG CCGCTACCAA AGCGTATGTT     180

GACCAATTCT CAAGATGCCT CTATGTTGAG TACAAGAGCA AGGGTATTGA TGTGCAATGC     240

CAGGTGCCCT TATACGTGG                                                  259

(2) INFORMATION FOR SEQ ID NO:2:

(i) SEQUENCE CHARACTERISTICS:
           (A) LENGTH: 309 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:2:

GCAAGAAGGG GCTGGCCAAG GACGCCAAGA AGAAGGCGCT GTGATTGATG TTTCAGAATG      60

CATGTTCAGA TTCGCACATT TCCTCATCAC CTGTAGTAGA CACGTGCCTT GCTGTAGTCA     120

CTTTATTAGC TACCATTACC TCCTGAGTCT GTTAAGAATC GAGAATGTCA TTGTTCCATC     180

CGCGGTTATG ATGATGAAAA ATACGATTCT TCAATTCAAA ATGTAACACT AATACGAGTA     240

ATGATGCATG AAATTAACTT GAAGAAGTTG TGCAACTCAG TTGTTTTTCT GAAAAAAAAA     300

AAAAAAAAA                                                             309

(2) INFORMATION FOR SEQ ID NO:3:

(i) SEQUENCE CHARACTERISTICS:
           (A) LENGTH: 1138 base pairs
           (B) TYPE: nucleic acid
           (C) STRANDEDNESS: double
           (D) TOPOLOGY: unknown (ii) MOLECULE TYPE: DNA (genomic)

(xi) SEQUENCE DESCRIPTION: SEQ ID NO:3:

GAATTCCCCG CTCCCTACCG CGGATCGAGC CAACTCACCC CCAAACCCAG CAAGCACGAT      60

GGCCGGCACG TGCGCCCACG TCGAGTTCCT CCGCGCGCAG CCGGCGTGGG CGCTGGCCCT     120

CGCGGCCGTC GGCCTCCTCG TCGCCGCCCG CGCCGCCCTT CGCCTCGCCC TCTGGGTCTA     180
```

-continued

```
CGCCGCCTTC CTCCGCCCCG GCAAGCACCT GCGCCGCCGC TACGGGCCCT GGGCCGTCGT      240

CACCGGCGCC ACCGACGGCA TCGGCCGCGC CATCGCCTTC CGCCTCGCCG CCTCCGGCCT      300

CGGCCTCGTG CTCGTCGGCC GCAACCCGGA CAAGCTCGCC GCCGTCTCCC AGGAGATCAG      360

GGCCAAGTAC CCCAAGACCG AGGTCCGCAC CTTCGTGCTC GACTTCGCCT CCGAGGGGCT      420

CGCCGCCGGG GTGGAGGCGC TCAAGGACTC CATCCGGGGC CTCGACGTCG GCGTGCTCGT      480

CAACAACGCC GGGGTCTCGT ACCCGTACGC CCGCTACTTC CACGAGGTGG ACGAGGAGCT      540

CATGCGGAGC CTCATCCGGG TCAACGTCGA GGGCGTAACG CGGGTCACCC ACGCCGTGCT      600

CCCGGGCATG GTCGACAGGA AGCGTGGCGC AATCGTCAAC ATCGGCTCCG GTGCTGCCTC      660

TGTCGTGCCG TCCGATCCAC TCTACTCCGT CTACGCCGCC ACCAAAGCGT ACGTTGACCA      720

GTTCTCAAGA TGCCTCTATG TTGAGTACAA GGGTAAGGGC ATCGATGTAC AATGCCAGGT      780

GCCCTTGTAC GTGGCAACAA AGATGGCATC AATCAGGAGG TCTTCCTTCC TTGTGCCATC      840

CGCGGACACC TATGCTCGTG CTGCTATTCG CCACATTGGC TATGAGCCGA GGTGCACACC      900

GTACTGGCCA CACTCTGTTC TGTGGTTCTT GATCTCCCTT CTCCCAGAGT CGCTGGTGGA      960

CAGTACGCGC CTCAGCATGT GCATCAAAAT CCGCAAGAAG GGGCAGGCTA AGGATGCCAA     1020

GAAGAAAGCG CAGTGATGAT TCATTGTTGA GATCTGCCAT GTTTGTTCGT CATGTGTAAC     1080

GAATCAGTAT TTGTAGCTCT GTTGTCGGCA TTTCAACATC ATTACCTTCG CGGAATTC      1138
```

(2) INFORMATION FOR SEQ ID NO:4:

(i) SEQUENCE CHARACTERISTICS:
        (A) LENGTH: 325 amino acids
        (B) TYPE: amino acid
        (D) TOPOLOGY: unknown (ii) MOLECULE TYPE: protein (xi) SEQUENCE DESCRIPTION: SEQ ID NO:4:

```
Met Ala Gly Thr Cys Ala His Val Glu Phe Leu Arg Ala Gln Pro Ala
  1               5                  10                  15

Trp Ala Leu Ala Leu Ala Ala Val Gly Leu Val Ala Ala Arg Ala
             20                  25                  30

Ala Leu Arg Leu Ala Leu Trp Val Tyr Ala Ala Phe Leu Arg Pro Gly
         35                  40                  45

Lys His Leu Arg Arg Arg Tyr Gly Pro Trp Ala Val Val Thr Gly Ala
     50                  55                  60

Thr Asp Gly Ile Gly Arg Ala Ile Ala Phe Arg Leu Ala Ala Ser Gly
 65                  70                  75                  80

Leu Gly Leu Val Leu Val Gly Arg Asn Pro Asp Lys Leu Ala Ala Val
                 85                  90                  95

Ser Gln Glu Ile Arg Ala Lys Tyr Pro Lys Thr Glu Val Arg Thr Phe
            100                 105                 110

Val Leu Asp Phe Ala Ser Glu Gly Leu Ala Ala Gly Val Glu Ala Leu
        115                 120                 125

Lys Asp Ser Ile Arg Gly Leu Asp Val Gly Val Leu Val Asn Asn Ala
    130                 135                 140

Gly Val Ser Tyr Pro Tyr Ala Arg Tyr Phe His Glu Val Asp Glu Glu
145                 150                 155                 160

Leu Met Arg Ser Leu Ile Arg Val Asn Val Glu Gly Val Thr Arg Val
                165                 170                 175

Thr His Ala Val Leu Pro Gly Met Val Asp Arg Lys Arg Gly Ala Ile
```

```
                    180                 185                 190
Val Asn Ile Gly Ser Gly Ala Ala Ser Val Val Pro Ser Asp Pro Leu
                195                 200                 205

Tyr Ser Val Tyr Ala Ala Thr Lys Ala Tyr Val Asp Gln Phe Ser Arg
    210                 215                 220

Cys Leu Tyr Val Glu Tyr Lys Gly Lys Gly Ile Asp Val Gln Cys Gln
225                 230                 235                 240

Val Pro Leu Tyr Val Ala Thr Lys Met Ala Ser Ile Arg Arg Ser Ser
                245                 250                 255

Phe Leu Val Pro Ser Ala Asp Thr Tyr Ala Arg Ala Ala Ile Arg His
                260                 265                 270

Ile Gly Tyr Glu Pro Arg Cys Thr Pro Tyr Trp Pro His Ser Val Leu
                275                 280                 285

Trp Phe Leu Ile Ser Leu Leu Pro Glu Ser Leu Val Asp Ser Thr Arg
                290                 295                 300

Leu Ser Met Cys Ile Lys Ile Arg Lys Lys Gly Gln Ala Lys Asp Ala
305                 310                 315                 320

Lys Lys Lys Ala Gln
                325

(2) INFORMATION FOR SEQ ID NO:5:

(i) SEQUENCE CHARACTERISTICS:
        (A) LENGTH: 872 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GAATTCGGCA CGAGAGCTTT TTTCTCAAGT AAATATATTC AGAATAGTGA AAACAAGAAA      60

ACACAACCGT ATAAAGTACA ACCACAAATA CGACGAACAC AAGAGTGCTT AACCACTTAA    120

ACTTCATAAG ACAATTATTT GTAAAGGAAA ACAAAAGCGT AAGATAAATT AAAGGGCGAT    180

CTACAGATCC TTCTTCTTGG CATCCTTGAG CTGCCCCTTT GTGCGGATAC CAAGGCAGAA    240

ACCAAGGCGC CAGTTGTCAA TAGCTGATTC GGGGAGAAGG GATAGCAGGC ACCAAATAGC    300

AGAGTGTGGC CAGTACGGAG TGCATCTAGG CTCATAGCCT ATCCATCTTA AGGCGGCTTT    360

GGCGTAGGTG TCCGATGATG GTACCATGAA TGACGACCTT CGGATTGACG CCATTTTTGT    420

TGCTACATAC AAGGGTACCT GGCACTGAAC ATCTATTCCC TTGCTTTTGT ATTCTACAAA    480

AAGGCATCTT GAGAATTGAT CAACATACGC TTTTGTAGCA GCGTACACCG CATAAAGCGG    540

GTCGGACGGA ATAACAATTG CAGCACCCGA CCCGATATTA CAATAGCAC CTTTCTTCCT    600

TTCGATCATG CCCGGAAGCA CAGCATGCGT AACCCTAGTA ACTCCCTCCA CATTTACCTT    660

AATCAAATTC CTCAACAGCT CATCGTCGAC TTCGTGAAAA TATCGTGCAT ACGGATACGA    720

CACGCCCGCG TTATTAACCA AAACACCAAC ATCTTTTCCC TTGATAGCAT CCTTAATCCT    780

TTCGACACCT TCCACCAAAT CGCCTGAAAA GTCCACAACT ACAGTCTCGA CTTTAATCCC    840

GCTGTTTTTA GACAAAATCT CGTGCCGAAT TC                                  872

(2) INFORMATION FOR SEQ ID NO:6:

(i) SEQUENCE CHARACTERISTICS:
        (A) LENGTH: 872 base pairs
        (B) TYPE: nucleic acid
        (C) STRANDEDNESS: double
```

(D) TOPOLOGY: linear (ii) MOLECULE TYPE: DNA (genomic)

(xi) SEQUENCE DESCRIPTION: SEQ ID NO:6:

GAATTCGGCA CGAGATTTTG TCTAAAAACA GCGGGATTAA AGTCGAGACT GTAGTTGTGG      60

ACTTTTCAGG CGATTTGGTG GAAGGTGTCG AAAGGATTAA GGATGCTATC AAGGGAAAAG     120

ATGTTGGTGT TTTGGTTAAT AACGCGGGCG TGTCGTATCC GTATGCACGA TATTTTCACG     180

AAGTCGACGA TGAGCTGTTG AGGAATTTGA TTAAGGTAAA TGTGGAGGGA GTTACTAGGG     240

TTACGCATGC TGTGCTTCCG GGCATGATCG AAAGGAAGAA AGGTTGCTAT TGTTAATATC     300

GGGTCGGGTG CTGCAATTGT TATTCCGTCC GACCCGCTTT ATGCGGTGTA CGCTGCTACA     360

AAAGCGTATG TTGATCAATT CTCAAGATGC CTTTTTGTAG AATACAAAAG CAAGGGAATA     420

GATGTTCAGT GCCAGGTACC CTTGTATGTA GCAACAAAAA TGCGTCAATC CGAAGGTCGT     480

CATTCATGGT ACCATCATCG GACACCTACG CCAAAGCCGC CTTAAGATGG ATAGGCTATG     540

AGCCTAGATG CACTCCGTAC TGGCCACACT CTGCTATTTG GTGCCTGCTA TCCCTTCTCC     600

CCGAATCAGC TATTGACAAC TGGCGCCTTG GTTTCTGCCT TGGTATCCGC ACAAAGGGGC     660

AGCTCAAGGA TGCCAAGAAG AAGGATCTGT AGATCGCCCT TTAATTTATC TTACGCTTTT     720

GTTTTCCTTT ACAAATAATT GTCTTATGAA GTTTAAGTGG TTAAGCACTC TTGTGTTCGT     780

CGTATTTGTG GTTGTACTTT ATACGGTTGT GTTTTCTTGT TTTCACTATT CTGAATATAT     840

TTACTTGAGA AAAAGCTCT CGTGCCGAAT TC                                    872

(2) INFORMATION FOR SEQ ID NO:7:

(i) SEQUENCE CHARACTERISTICS:
         (A) LENGTH: 200 amino acids
         (B) TYPE: amino acid
         (D) TOPOLOGY: unknown (ii) MOLECULE TYPE: protein (xi) SEQUENCE DESCRIPTION: SEQ ID NO:7:

Ile Arg His Glu Ile Leu Ser Lys Asn Ser Gly Ile Lys Val Glu Thr
1               5                   10                  15

Val Val Val Asp Phe Ser Gly Asp Leu Val Glu Gly Val Glu Arg Ile
            20                  25                  30

Lys Asp Ala Ile Lys Gly Lys Asp Val Gly Val Leu Val Asn Asn Ala
        35                  40                  45

Gly Val Ser Tyr Pro Tyr Ala Arg Tyr Phe His Glu Val Asp Asp Glu
    50                  55                  60

Leu Leu Arg Asn Leu Ile Lys Val Asn Val Glu Gly Val Thr Arg Val
65                  70                  75                  80

Thr His Ala Val Leu Pro Gly Met Ile Glu Arg Lys Lys Gly Ala Ile
                85                  90                  95

Val Asn Ile Gly Ser Gly Ala Ala Ile Val Ile Pro Ser Asp Pro Leu
            100                 105                 110

Tyr Ala Val Tyr Ala Ala Thr Lys Ala Tyr Val Asp Gln Phe Ser Arg
        115                 120                 125

Cys Leu Phe Val Glu Tyr Lys Ser Lys Gly Ile Asp Val Gln Cys Gln
    130                 135                 140

Val Pro Leu Tyr Val Ala Thr Lys Met Ala Ser Ile Arg Arg Ser Ser
145                 150                 155                 160

Phe Met Val Pro Ser Ser Asp Thr Tyr Ala Lys Ala Ala Leu Arg Trp

```
                            165                 170                  175
Ile Gly Tyr Glu Pro Arg Cys Thr Pro Tyr Trp Pro His Ser Ala Ile
                180                 185                 190

Trp Cys Leu Leu Ser Leu Leu Pro
            195                 200

(2) INFORMATION FOR SEQ ID NO:8:

(i) SEQUENCE CHARACTERISTICS:
         (A) LENGTH: 896 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..759

(xi) SEQUENCE DESCRIPTION: SEQ ID NO:8:

GAC CCA CGC GTC CGG TTA GCC CAG AAA GGT CTT AAC CTT ATA CTC GTT      48
Asp Pro Arg Val Arg Leu Ala Gln Lys Gly Leu Asn Leu Ile Leu Val
                295                 300                 305

GCT CGT AAC CCA GAC AAG CTC AAA GAT GTC TCT GAT TCC ATC AGA TCT      96
Ala Arg Asn Pro Asp Lys Leu Lys Asp Val Ser Asp Ser Ile Arg Ser
            310                 315                 320

AAG TAT AGT CAA ACT CAG ATC TTG ACC GTT GTG ATG GAT TTC TCT GGA     144
Lys Tyr Ser Gln Thr Gln Ile Leu Thr Val Val Met Asp Phe Ser Gly
        325                 330                 335

GAT ATT GAT GAA GGT GTG AAA CGG ATT AAG GAG AGT ATT GAA GGA TTA     192
Asp Ile Asp Glu Gly Val Lys Arg Ile Lys Glu Ser Ile Glu Gly Leu
    340                 345                 350

GAT GTT GGG ATT TTG ATT AAT AAT GCT GGC ATG TCT TAT CCT TAT GCT     240
Asp Val Gly Ile Leu Ile Asn Asn Ala Gly Met Ser Tyr Pro Tyr Ala
355                 360                 365                 370

AAG TAT TTT CAT GAG GTT GAT GAA GAG TTG ATC AAT AAC TTG ATT AAG     288
Lys Tyr Phe His Glu Val Asp Glu Glu Leu Ile Asn Asn Leu Ile Lys
                375                 380                 385

ATC AAT GTT GAA GGA ACT ACT AAA GTT ACT CAA GCT GTG TTG CCT AAT     336
Ile Asn Val Glu Gly Thr Thr Lys Val Thr Gln Ala Val Leu Pro Asn
            390                 395                 400

ATG CTT AAG AGG AAG AAA GGT GCT ATT ATT AAT ATG GGT TCT GGT GCT     384
Met Leu Lys Arg Lys Lys Gly Ala Ile Ile Asn Met Gly Ser Gly Ala
        405                 410                 415

GCT GCT CTT ATT CCT TCT TAT CCT TTT TAC TCT GTT TAT GCT GGT GCT     432
Ala Ala Leu Ile Pro Ser Tyr Pro Phe Tyr Ser Val Tyr Ala Gly Ala
    420                 425                 430

AAA ACG TAC GTG GAT CAG TTC ACA AAG TGT CTA CAT GTT GAG TAT AAG     480
Lys Thr Tyr Val Asp Gln Phe Thr Lys Cys Leu His Val Glu Tyr Lys
435                 440                 445                 450

AAG AGT GGG ATT GAT GTT CAA TGC CAG GTT CCC TTG TAT GTT GCA ACA     528
Lys Ser Gly Ile Asp Val Gln Cys Gln Val Pro Leu Tyr Val Ala Thr
                455                 460                 465

AAG ATG ACA AAA ATA AGA AGA GCA TCC TTC TTA GTT GCA TCA CCA GAG     576
Lys Met Thr Lys Ile Arg Arg Ala Ser Phe Leu Val Ala Ser Pro Glu
            470                 475                 480

GGT TAC GCA AAG GCA GCA CTG CGT TTT GTA GGC TAT GAA GCA CAA TGC     624
Gly Tyr Ala Lys Ala Ala Leu Arg Phe Val Gly Tyr Glu Ala Gln Cys
        485                 490                 495

ACA CCG TAC TGG CCT CAC GCT CTC ATG GGT GCA GTT GTC TCT GCA TTG     672
Thr Pro Tyr Trp Pro His Ala Leu Met Gly Ala Val Val Ser Ala Leu
```

```
          500                 505                 510
CCC GAA AGC GTT TTT GAA TCA TTT AAC ATC AAG AGA TGC CTC CAG ATC            720
Pro Glu Ser Val Phe Glu Ser Phe Asn Ile Lys Arg Cys Leu Gln Ile
515                 520                 525                 530

CGG AAG AAG GGT CTC CAA AAA GAC TCC ATG AAG AAA GAA TGAATCTTCC             769
Arg Lys Lys Gly Leu Gln Lys Asp Ser Met Lys Lys Glu
                    535                 540

AGGTTTAAGT TACTACCAAG AATTTCCTTC TTCTGAAGTT GTTGGTTTCT TGAAAAGCTT          829

CTGTTCTGAA TCTTTTGTAA GACTTGTACT CTTTAGTTTT CTAAGTTTTT TAAAAAAAAA          889

AAAAAAA                                                                    896
```

(2) INFORMATION FOR SEQ ID NO:9:

(i) SEQUENCE CHARACTERISTICS:
        (A) LENGTH: 253 amino acids
        (B) TYPE: amino acid
        (D) TOPOLOGY: unknown (ii) MOLECULE TYPE: protein (xi) SEQUENCE DESCRIPTION: SEQ ID NO:9:

```
Asp Pro Arg Val Arg Leu Ala Gln Lys Gly Leu Asn Leu Ile Leu Val
1               5                   10                  15

Ala Arg Asn Pro Asp Lys Leu Lys Asp Val Ser Asp Ser Ile Arg Ser
                20                  25                  30

Lys Tyr Ser Gln Thr Gln Ile Leu Thr Val Val Met Asp Phe Ser Gly
            35                  40                  45

Asp Ile Asp Glu Gly Val Lys Arg Ile Lys Glu Ser Ile Glu Gly Leu
        50                  55                  60

Asp Val Gly Ile Leu Ile Asn Asn Ala Gly Met Ser Tyr Pro Tyr Ala
65                  70                  75                  80

Lys Tyr Phe His Glu Val Asp Glu Glu Leu Ile Asn Asn Leu Ile Lys
                85                  90                  95

Ile Asn Val Glu Gly Thr Thr Lys Val Thr Gln Ala Val Leu Pro Asn
            100                 105                 110

Met Leu Lys Arg Lys Lys Gly Ala Ile Ile Asn Met Gly Ser Gly Ala
        115                 120                 125

Ala Ala Leu Ile Pro Ser Tyr Pro Phe Tyr Ser Val Tyr Ala Gly Ala
130                 135                 140

Lys Thr Tyr Val Asp Gln Phe Thr Lys Cys Leu His Val Glu Tyr Lys
145                 150                 155                 160

Lys Ser Gly Ile Asp Val Gln Cys Gln Val Pro Leu Tyr Val Ala Thr
                165                 170                 175

Lys Met Thr Lys Ile Arg Arg Ala Ser Phe Leu Val Ala Ser Pro Glu
            180                 185                 190

Gly Tyr Ala Lys Ala Leu Arg Phe Val Gly Tyr Glu Ala Gln Cys
        195                 200                 205

Thr Pro Tyr Trp Pro His Ala Leu Met Gly Ala Val Val Ser Ala Leu
    210                 215                 220

Pro Glu Ser Val Phe Glu Ser Phe Asn Ile Lys Arg Cys Leu Gln Ile
225                 230                 235                 240

Arg Lys Lys Gly Leu Gln Lys Asp Ser Met Lys Lys Glu
                245                 250
```

(2) INFORMATION FOR SEQ ID NO:10:

(i) SEQUENCE CHARACTERISTICS:
    (A) LENGTH: 950 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:10:

```
GAATTCGGCA CGAGGTCCAC GGTCCACACA CGCCTTCCTT ATATCGGCGC TCACGGTTCT      60
ATAAAAAAAA CACAGTACGA GCAGAGCAAG GCGGCCGTGA GCTGAGCTGA GGGAAGGACG     120
ACGTACGGCA CAGTTGCTAG CCCGGCCGCC GGAGCTCTCC GTGATCTGGG CCGCCAGCAA     180
CAGCATGGGT GCCGCGCTCT TGGCTTCTTG GCCATGGGAC AACCTCGGCT TCTACAAGTA     240
CGTCCTGTAC GGGCCGCTGG TGGGCAAGGC GGTGGCGTCA CGGGCGTGGG AGGCGGCGAG     300
CCCCGACCGC TGGATCCTCC TCCTGCTCCT CCTCTTCGGC CTCCGCGCGC TCACCTACCA     360
GCTCTGGAGC TCCTTCAGCA ACATGCTCTT CGCCACACGC CGGCGCCGCG TCGTCCGCGA     420
CGGCGTCGAC TTCGACCAGA TCGACAAGGA GTGGGACTGG GACAACTTCC TGATCCTGCA     480
CGCCCTGATG GCGGCCGCGG CGCTGTGCGC GTTCCCGTCG CTGCGGCATC TCCCGGCGTG     540
GGACGGCCGG GGGTTCGCCG TCGCGCTCGT CGCCCACGCG GCGGCCACCG AGCCCCTCTC     600
CTACCTGGCG CACAGGGCGC TCCACGGCAG CAGCGGCCGC CTCTACGCGC GCTACCACTC     660
GCTGCACCAC TCCAGCAGGG TGCCGCAGCC GTTCACGGCG GGGCTGGCCA CGCCGCTGGA     720
GCACGTGGCG CTGGGCGCGC TCATGTCGCT GCCCCTCGCG GCCGCGCGCG CCGCCGGGTG     780
CGCCTCCGTC GCGCTCGCCT TCGCCTACGT GCTCGCCTTC GACTCCCTCC GCGCCATGGG     840
CCACTGCAAC GTCGAGGTCG TCCCGGCCTC GCTCTTCCGG GCCATCCCGG CCCTCAGATA     900
CGTTCTCTAC ACCCCGACGT ACGTACCACG CGATTCACCA CACCAAGAAG                950
```

(2) INFORMATION FOR SEQ ID NO:11:

(i) SEQUENCE CHARACTERISTICS:
    (A) LENGTH: 585 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:11:

```
AATCGACCGA CGCTCGTGGG ACATGCAGAG GAAGATGAGC GCAGGTACAC ACGTCGTCTC      60
GTTTTATGTC CCTGGTCCAT GACAGGCCAC CAAACTACCT ATATTGGACT AACCCATTTT     120
AGCTTTAACA ACCTTACTAG CTAAGGCATC CACACACACA TACCCATACA ACTTAGCAAT     180
CCTGCACTAG CCGGAACACT GACACTGAAA CAAAGAGCGG ACCCCTTTGA CCAGAACTGC     240
CTAGTAAACA GACATCAAGA AAGAGTGTTA GGCAACCAGC CGCTACAGAC GAGCTAAACA     300
TCCACCAACG AGCTCTTTCA CCACCTGCGC AACTTGCTCT GTTGTTCTCT GTTGTCCATT     360
GAAGATTATG TTGTTGCTTT CCAACCATAC GCTCCACCAG AAGTAAATTA GTAGGCCATC     420
GAAACTTTTT CTTGATTGCT TGCTATAGAG CATCCTCAGT CTATGCCACC AAGTGTATAG     480
GGTTCCCGTC TTTGGAGTAC CGTCTAGGAA CCACAGATCG GTCCAAGACA AGATCATGCT     540
CCACACTTCC TCATATATCA CCAAAGCAAA AAAAAAAAA AAAAA                      585
```

(2) INFORMATION FOR SEQ ID NO:12:

(i) SEQUENCE CHARACTERISTICS:

(A) LENGTH: 319 amino acids
          (B) TYPE: amino acid
          (D) TOPOLOGY: unknown (ii) MOLECULE TYPE: protein (xi) SEQUENCE DESCRIPTION: SEQ ID NO:12:

Met Gly Ala Ala Leu Leu Ala Ser Trp Pro Trp Asp Asn Leu Gly Phe
1               5                   10                  15

Tyr Lys Tyr Val Leu Tyr Gly Pro Leu Val Gly Lys Ala Val Ala Ser
                20                  25                  30

Arg Ala Trp Glu Ala Ala Ser Pro Asp Arg Trp Ile Leu Leu Leu Leu
            35                  40                  45

Leu Leu Phe Gly Leu Arg Ala Leu Thr Tyr Gln Leu Trp Ser Ser Phe
50                      55                  60

Ser Asn Met Leu Phe Ala Thr Arg Arg Arg Val Val Arg Asp Gly
65                  70                  75                  80

Val Asp Phe Asp Gln Ile Asp Lys Glu Trp Asp Trp Asp Asn Phe Leu
                85                  90                  95

Ile Leu His Ala Leu Met Ala Ala Ala Leu Cys Ala Phe Pro Ser
                100                 105                 110

Leu Arg His Leu Pro Ala Trp Asp Gly Arg Gly Phe Ala Val Ala Leu
            115                 120                 125

Val Ala His Ala Ala Thr Glu Pro Leu Ser Tyr Leu Ala His Arg
130                 135                 140

Ala Leu His Gly Ser Ser Gly Arg Leu Tyr Ala Arg Tyr His Ser Leu
145                 150                 155                 160

His His Ser Ser Arg Val Pro Gln Pro Phe Thr Ala Gly Leu Ala Thr
                165                 170                 175

Pro Leu Glu His Val Ala Leu Gly Ala Leu Met Ser Leu Pro Leu Ala
            180                 185                 190

Ala Ala Arg Ala Ala Gly Cys Ala Ser Val Ala Leu Ala Phe Ala Tyr
        195                 200                 205

Val Leu Ala Phe Asp Ser Leu Arg Ala Met Gly His Cys Asn Val Glu
210                 215                 220

Val Val Pro Ala Ser Leu Phe Arg Ala Ile Pro Ala Leu Arg Tyr Val
225                 230                 235                 240

Leu Tyr Thr Pro Thr Tyr Val Pro Arg Asp Ser Pro His Gln Glu Gly
                245                 250                 255

Gly Gln Leu Leu Ser Leu His Ala Ala Val Arg Ser Ala Gly Trp His
            260                 265                 270

Asn Arg Pro Thr Leu Val Gly His Ala Glu Glu Asp Glu Arg Arg Tyr
        275                 280                 285

Thr Arg Arg Leu Val Leu Cys Pro Trp Ser Met Thr Gly His Gln Thr
290                 295                 300

Thr Tyr Ile Gly Leu Thr His Phe Ser Phe Asn Asn Leu Thr Ser
305                 310                 315

(2) INFORMATION FOR SEQ ID NO:13:

(i) SEQUENCE CHARACTERISTICS:
          (A) LENGTH: 1935 base pairs
          (B) TYPE: nucleic acid
          (C) STRANDEDNESS: double
          (D) TOPOLOGY: linear (ii) MOLECULE TYPE: DNA (genomic)

(ix) FEATURE:
    (A) NAME/KEY: CDS
    (B) LOCATION: 3..1784

(xi) SEQUENCE DESCRIPTION: SEQ ID NO:13:

```
AA GGG GAT GAT GAT CTA GCA AAC AAT TGG TGT TTC CAC ATT CTA GTG          47
   Gly Asp Asp Asp Leu Ala Asn Asn Trp Cys Phe His Ile Leu Val
   1               5                   10                  15

ATA AGC TTG CTT AGA TTT AAT CTA TAT ATG TGG TAT ACT AAC ATT TGT         95
Ile Ser Leu Leu Arg Phe Asn Leu Tyr Met Trp Tyr Thr Asn Ile Cys
                20                  25                  30

AAC ATG CTT TTC CTC ACT CGG AAT CGT CGG ATT TTA CAT CAA AGC ATT        143
Asn Met Leu Phe Leu Thr Arg Asn Arg Arg Ile Leu His Gln Ser Ile
                35                  40                  45

GAC TTT AAC CAG ATT GAT AAA GAA TGG AAC TGG GAC AAT TTT GTA ATT        191
Asp Phe Asn Gln Ile Asp Lys Glu Trp Asn Trp Asp Asn Phe Val Ile
                50                  55                  60

TTA CAA GCT CTA ATA GCT TCA TTG GCG ATT TAT ATG TTC CCT CAA GAA        239
Leu Gln Ala Leu Ile Ala Ser Leu Ala Ile Tyr Met Phe Pro Gln Glu
    65                  70                  75

TTT GCA AAC TTA CCG GTG TGG AAA ACC AAA GGG CTT GTG GCA ATT GTG        287
Phe Ala Asn Leu Pro Val Trp Lys Thr Lys Gly Leu Val Ala Ile Val
80                  85                  90                  95

GTG ATA CAC GTG GTT GTA TCA GAG CCA CTT TAC TAT TGG TTG CAT AGA        335
Val Ile His Val Val Val Ser Glu Pro Leu Tyr Tyr Trp Leu His Arg
                100                 105                 110

TTG TTA CAT ACA AAT TAC CTA TTT ACC CCT TAC CAT TCT TTC CAC CAT        383
Leu Leu His Thr Asn Tyr Leu Phe Thr Pro Tyr His Ser Phe His His
                115                 120                 125

TCA TCA GCT GTG CCC CAA CCA GTT ACA GTT GGA AGC ACC ACA TTC TTG        431
Ser Ser Ala Val Pro Gln Pro Val Thr Val Gly Ser Thr Thr Phe Leu
            130                 135                 140

GAG GAG TTA TTA GTT ACG GCG GTG CTT GGA CTA CCA ATA CTT GGT TGT        479
Glu Glu Leu Leu Val Thr Ala Val Leu Gly Leu Pro Ile Leu Gly Cys
            145                 150                 155

AGT TTG TCT GGA TAC GGA TCT AAA TCC ATA ATA TAT GGC TAT GTT TTG        527
Ser Leu Ser Gly Tyr Gly Ser Lys Ser Ile Ile Tyr Gly Tyr Val Leu
160                 165                 170                 175

GTC TTT GAT TTC TTA CGA TGT TTG GGG CAT TCA AAC GTT GAG ATC ATG        575
Val Phe Asp Phe Leu Arg Cys Leu Gly His Ser Asn Val Glu Ile Met
                180                 185                 190

CCT CAT TGG ATT TTC GAC TAC TTT CCT TTC TTC AGA TTC ATT ATC TAC        623
Pro His Trp Ile Phe Asp Tyr Phe Pro Phe Phe Arg Phe Ile Ile Tyr
                195                 200                 205

ACC CCA ACA TAC TAT AGC CTA CAC CAC AGT GAG ATG AAG AGC AAC TAT        671
Thr Pro Thr Tyr Tyr Ser Leu His His Ser Glu Met Lys Ser Asn Tyr
            210                 215                 220

TGC CTA TTT ATG CCA CTT TAT GAC ACC ATG TGG AAC ACT TTG AAC ACG        719
Cys Leu Phe Met Pro Leu Tyr Asp Thr Met Trp Asn Thr Leu Asn Thr
225                 230                 235

AAG TCG TGG GGT CTA CAC AAG AAA ATA AGT CTA GAC TCA GGC AAG TCA        767
Lys Ser Trp Gly Leu His Lys Lys Ile Ser Leu Asp Ser Gly Lys Ser
240                 245                 250                 255

ACG CGG GTG CCA GAT TTT GTG TTC TTG GCA CAT GTG GTG GAT ATA ACA        815
Thr Arg Val Pro Asp Phe Val Phe Leu Ala His Val Val Asp Ile Thr
                260                 265                 270

TCT GCA CTA CAT GTT CCC TTC GTC ATC AGA TCA TTT TCA GCG ATG GCT        863
Ser Ala Leu His Val Pro Phe Val Ile Arg Ser Phe Ser Ala Met Ala
            275                 280                 285

TAT AGT GCT AGG CTT TTC TTG CTT CCA TTA TGG CCA TTT ACT TTC GCC        911
```

```
Tyr Ser Ala Arg Leu Phe Leu Leu Pro Leu Trp Pro Phe Thr Phe Ala
            290                 295                 300

GTG ATG ATA GTG ATG TGG GCT AGG TCT AAG ACA TTT CTT TTG TCT TCT        959
Val Met Ile Val Met Trp Ala Arg Ser Lys Thr Phe Leu Leu Ser Ser
        305                 310                 315

TAC AAC TTA AGA GGC CGA TTG CAC CAA ACT TGG GTT GTT CCT CGT TTT       1007
Tyr Asn Leu Arg Gly Arg Leu His Gln Thr Trp Val Val Pro Arg Phe
320                 325                 330                 335

GGC TTC CAG TAT TTC TTG CCA TTC GCT TGC CAA GGC ATT AAC AAT CAT       1055
Gly Phe Gln Tyr Phe Leu Pro Phe Ala Cys Gln Gly Ile Asn Asn His
                340                 345                 350

ATT GAG GAG GCC ATT CTT AGA GCT GAC AAA TTG GGT GTG AAG GTC ATT       1103
Ile Glu Glu Ala Ile Leu Arg Ala Asp Lys Leu Gly Val Lys Val Ile
            355                 360                 365

AGC CTT GCT GCG TTA AAT AAG AAT GAA TCA CTT AAC AGA GGT GGA ACG       1151
Ser Leu Ala Ala Leu Asn Lys Asn Glu Ser Leu Asn Arg Gly Gly Thr
        370                 375                 380

TTG TTT GTG AAA AAA CAC CCG AAT TTG AAA GTA CGG GTG GTC CAT GGA       1199
Leu Phe Val Lys Lys His Pro Asn Leu Lys Val Arg Val Val His Gly
385                 390                 395

AAT ACA TTG ACA GCC GCT GTT ATC CTC AAT GAG ATT AAT GAA GAC GTG       1247
Asn Thr Leu Thr Ala Ala Val Ile Leu Asn Glu Ile Asn Glu Asp Val
400                 405                 410                 415

AAA GAG GTG TTT CTC ACC GGA GCC ACT TCA AAG CTT GGA CGG GCC ATC       1295
Lys Glu Val Phe Leu Thr Gly Ala Thr Ser Lys Leu Gly Arg Ala Ile
                420                 425                 430

GCC CTT TAC CTT TGT CGA CGA GGC GTT CAT GTT CTT ATG TTG ACC CTA       1343
Ala Leu Tyr Leu Cys Arg Arg Gly Val His Val Leu Met Leu Thr Leu
            435                 440                 445

TCA ACG GAG AGA TTT CAA AAC ATC CAA GAA GAA GCA CCA TCA AAA TGC       1391
Ser Thr Glu Arg Phe Gln Asn Ile Gln Glu Glu Ala Pro Ser Lys Cys
        450                 455                 460

AGG AAG AAT TTG GTC CAA GTC ACC AAG TAC CAA GCA GCC AAA AAT TGC       1439
Arg Lys Asn Leu Val Gln Val Thr Lys Tyr Gln Ala Ala Lys Asn Cys
465                 470                 475

AAG ACA TGG GTG ATC GGA AAA TGG ATA ACA CCG GGA CAA CAA CGT TGG       1487
Lys Thr Trp Val Ile Gly Lys Trp Ile Thr Pro Gly Gln Gln Arg Trp
480                 485                 490                 495

GCG CCA TCA GGA ACT CAT TTT CAT CAG TTT GTG GTG CCA CCC ATT TTA       1535
Ala Pro Ser Gly Thr His Phe His Gln Phe Val Val Pro Pro Ile Leu
                500                 505                 510

GCT TTC AGA AGA ACT GCA CCT ACG GAG ACC TTG CCG CTT ATG AAA CTT       1583
Ala Phe Arg Arg Thr Ala Pro Thr Glu Thr Leu Pro Leu Met Lys Leu
            515                 520                 525

CCC GAT GAT GTT GAA GGC CTT GGA TCA TGC GAG TAT ACA ATG GGA AGA       1631
Pro Asp Asp Val Glu Gly Leu Gly Ser Cys Glu Tyr Thr Met Gly Arg
        530                 535                 540

GGA ATA GTG CAT GCA TGC CAT GCC GGA GGG GTT GTA CAT AGC TTG GAA       1679
Gly Ile Val His Ala Cys His Ala Gly Gly Val Val His Ser Leu Glu
545                 550                 555

GGA TGG ACT CAT CAT GAA GTT GGT GCT CTT GAT GTT GAT CGA ATC GAC       1727
Gly Trp Thr His His Glu Val Gly Ala Leu Asp Val Asp Arg Ile Asp
560                 565                 570                 575

GTC GTT TGG AAA GCA GCT TTA AAG CAT GGT CTT CAA TCT GTT TCC AGT       1775
Val Val Trp Lys Ala Ala Leu Lys His Gly Leu Gln Ser Val Ser Ser
                580                 585                 590

CTT CCC AAA TGATCTTATT TCTAATCATT TGTTTAAATT CATATTTAAT              1824
Leu Pro Lys
        595
```

```
ATCAGAATCA TTATTTTTTG TTTTACATTC TTGAATTTGG TACTCTTAGT TCGATATTAC    1884

AATATGTATG ATTGCGTATT AATTGGAAAG TAATGCAGAT GTTTATGGAT T             1935
```

(2) INFORMATION FOR SEQ ID NO:14:

(i) SEQUENCE CHARACTERISTICS:
      (A) LENGTH: 594 amino acids
      (B) TYPE: amino acid
      (D) TOPOLOGY: unknown (ii) MOLECULE TYPE: protein (xi) SEQUENCE DESCRIPTION: SEQ ID NO:14:

```
Gly Asp Asp Asp Leu Ala Asn Asn Trp Cys Phe His Ile Leu Val Ile
 1               5                  10                  15

Ser Leu Leu Arg Phe Asn Leu Tyr Met Trp Tyr Thr Asn Ile Cys Asn
                20                  25                  30

Met Leu Phe Leu Thr Arg Asn Arg Arg Ile Leu His Gln Ser Ile Asp
            35                  40                  45

Phe Asn Gln Ile Asp Lys Glu Trp Asn Trp Asp Asn Phe Val Ile Leu
        50                  55                  60

Gln Ala Leu Ile Ala Ser Leu Ala Ile Tyr Met Phe Pro Gln Glu Phe
 65                  70                  75                  80

Ala Asn Leu Pro Val Trp Lys Thr Lys Gly Leu Val Ala Ile Val Val
                85                  90                  95

Ile His Val Val Val Ser Glu Pro Leu Tyr Tyr Trp Leu His Arg Leu
                100                 105                 110

Leu His Thr Asn Tyr Leu Phe Thr Pro Tyr His Ser Phe His His Ser
            115                 120                 125

Ser Ala Val Pro Gln Pro Val Thr Val Gly Ser Thr Thr Phe Leu Glu
        130                 135                 140

Glu Leu Leu Val Thr Ala Val Leu Gly Leu Pro Ile Leu Gly Cys Ser
145                 150                 155                 160

Leu Ser Gly Tyr Gly Ser Lys Ser Ile Ile Tyr Gly Tyr Val Leu Val
                165                 170                 175

Phe Asp Phe Leu Arg Cys Leu Gly His Ser Asn Val Glu Ile Met Pro
            180                 185                 190

His Trp Ile Phe Asp Tyr Phe Pro Phe Arg Phe Ile Ile Tyr Thr
        195                 200                 205

Pro Thr Tyr Tyr Ser Leu His Ser Glu Met Lys Ser Asn Tyr Cys
        210                 215                 220

Leu Phe Met Pro Leu Tyr Asp Thr Met Trp Asn Thr Leu Asn Thr Lys
225                 230                 235                 240

Ser Trp Gly Leu His Lys Lys Ile Ser Leu Asp Ser Gly Lys Ser Thr
                245                 250                 255

Arg Val Pro Asp Phe Val Phe Leu Ala His Val Val Asp Ile Thr Ser
            260                 265                 270

Ala Leu His Val Pro Phe Val Ile Arg Ser Phe Ser Ala Met Ala Tyr
        275                 280                 285

Ser Ala Arg Leu Phe Leu Leu Pro Leu Trp Pro Phe Thr Phe Ala Val
        290                 295                 300

Met Ile Val Met Trp Ala Arg Ser Lys Thr Phe Leu Leu Ser Ser Tyr
305                 310                 315                 320

Asn Leu Arg Gly Arg Leu His Gln Thr Trp Val Val Pro Arg Phe Gly
                325                 330                 335
```

—continued

```
Phe Gln Tyr Phe Leu Pro Phe Ala Cys Gln Gly Ile Asn Asn His Ile
            340                 345                 350

Glu Glu Ala Ile Leu Arg Ala Asp Lys Leu Gly Val Lys Val Ile Ser
            355                 360                 365

Leu Ala Ala Leu Asn Lys Asn Glu Ser Leu Asn Arg Gly Gly Thr Leu
            370                 375                 380

Phe Val Lys Lys His Pro Asn Leu Lys Val Arg Val His Gly Asn
385                 390                 395                 400

Thr Leu Thr Ala Ala Val Ile Leu Asn Glu Ile Asn Glu Asp Val Lys
                405                 410                 415

Glu Val Phe Leu Thr Gly Ala Thr Ser Lys Leu Gly Arg Ala Ile Ala
            420                 425                 430

Leu Tyr Leu Cys Arg Arg Gly Val His Val Leu Met Leu Thr Leu Ser
            435                 440                 445

Thr Glu Arg Phe Gln Asn Ile Gln Glu Glu Ala Pro Ser Lys Cys Arg
            450                 455                 460

Lys Asn Leu Val Gln Val Thr Lys Tyr Gln Ala Ala Lys Asn Cys Lys
465                 470                 475                 480

Thr Trp Val Ile Gly Lys Trp Ile Thr Pro Gly Gln Gln Arg Trp Ala
                485                 490                 495

Pro Ser Gly Thr His Phe His Gln Phe Val Val Pro Ile Leu Ala
            500                 505                 510

Phe Arg Arg Thr Ala Pro Thr Glu Thr Leu Pro Leu Met Lys Leu Pro
            515                 520                 525

Asp Asp Val Glu Gly Leu Gly Ser Cys Glu Tyr Thr Met Gly Arg Gly
530                 535                 540

Ile Val His Ala Cys His Ala Gly Gly Val Val His Ser Leu Glu Gly
545                 550                 555                 560

Trp Thr His His Glu Val Gly Ala Leu Asp Val Asp Arg Ile Asp Val
                565                 570                 575

Val Trp Lys Ala Ala Leu Lys His Gly Leu Gln Ser Val Ser Ser Leu
            580                 585                 590

Pro Lys
```

(2) INFORMATION FOR SEQ ID NO:15:

(i) SEQUENCE CHARACTERISTICS:
        (A) LENGTH: 1903 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1665

(xi) SEQUENCE DESCRIPTION: SEQ ID NO:15:

```
AAC ATG CTC TTC TTC ACC CGC CGC CGC CGC GTC GTC GAC GAC GGC GTC    48
Asn Met Leu Phe Phe Thr Arg Arg Arg Arg Val Val Asp Asp Gly Val
 1               5                  10                  15

GAC TTC CGC CAG ATC GAC ACC GAG TGG GAC TGG GAT AAC ATG GTG ATC    96
Asp Phe Arg Gln Ile Asp Thr Glu Trp Asp Trp Asp Asn Met Val Ile
             20                  25                  30

ATG CAA ACC CTA ATC GCG GCG GTG CTG GTC ACC AGC CGT GTC TTC CCT   144
Met Gln Thr Leu Ile Ala Ala Val Leu Val Thr Ser Arg Val Phe Pro
         35                  40                  45
```

```
GCC ACG TCG GAT CTC TCG GCG TGG GAC CTA CGT GGG TGG GCC ATC GCT      192
Ala Thr Ser Asp Leu Ser Ala Trp Asp Leu Arg Gly Trp Ala Ile Ala
     50                  55                  60

GTG GTG CTG CAC GTG GCC GTT TCA GAG CCG GCC TTC TAC TGG GCC CAC      240
Val Val Leu His Val Ala Val Ser Glu Pro Ala Phe Tyr Trp Ala His
 65              70                  75                  80

CGG GCC CTC CAT CTG GGC CCA CTC TTC AGC CGG TAC CAC TCC TTG CAC      288
Arg Ala Leu His Leu Gly Pro Leu Phe Ser Arg Tyr His Ser Leu His
                 85                  90                  95

CAC TCC TTC CAA GCC ACC CAA GCT CTC ACA GCT GGG TTC GTG ACG CCA      336
His Ser Phe Gln Ala Thr Gln Ala Leu Thr Ala Gly Phe Val Thr Pro
            100                 105                 110

TTG GAG AGC CTG ATC CTG ACG CTG GTG GCG TGG CCC CAC TTG CAG GGC      384
Leu Glu Ser Leu Ile Leu Thr Leu Val Ala Trp Pro His Leu Gln Gly
        115                 120                 125

CTT CAT GGC GGG ACA CGG CTC CGT GAG CTG GTC TAT GGA CAC ATC TCC      432
Leu His Gly Gly Thr Arg Leu Arg Glu Leu Val Tyr Gly His Ile Ser
    130                 135                 140

TCT TCG ACT ACT CCG GTC CAT GGG GTA CAG CAA CGT CGA GGT CAT CTC      480
Ser Ser Thr Thr Pro Val His Gly Val Gln Gln Arg Arg Gly His Leu
145                 150                 155                 160

ACA CAA GAC TTC CAG GAT TTT CCC TTT CTC AGA TAC CTC ATC TAC ACA      528
Thr Gln Asp Phe Gln Asp Phe Pro Phe Leu Arg Tyr Leu Ile Tyr Thr
                165                 170                 175

CCA TCG TAT CTT AGC CTA CAC CAC AGG GAG AAG GAC TCC AAT TTC TGC      576
Pro Ser Tyr Leu Ser Leu His His Arg Glu Lys Asp Ser Asn Phe Cys
            180                 185                 190

CTG TTC ATG CCT CTC TTT GAT GCC CTG GGA GGG ACC CTC AAC CCC AAG      624
Leu Phe Met Pro Leu Phe Asp Ala Leu Gly Gly Thr Leu Asn Pro Lys
        195                 200                 205

TCT TGG CAG CTT CAG AAG GAG GTT GAC CTA GGA AAG AAC CAT CGG GTG      672
Ser Trp Gln Leu Gln Lys Glu Val Asp Leu Gly Lys Asn His Arg Val
    210                 215                 220

CCG GAC TTT GTG TTC CTG GTG CAC GTG GTG GAC GTG GTG TCG TCG ATG      720
Pro Asp Phe Val Phe Leu Val His Val Val Asp Val Val Ser Ser Met
225                 230                 235                 240

CAC GTG CCA TTC GCG TTC CGA GCG TGC AGC TCG CTG CCG TTC GCG ACG      768
His Val Pro Phe Ala Phe Arg Ala Cys Ser Ser Leu Pro Phe Ala Thr
                245                 250                 255

CAC CTC GTC CTT CTC CCG CTC TGG CCC ATC GCC TTC GGC TTC ATG CTC      816
His Leu Val Leu Leu Pro Leu Trp Pro Ile Ala Phe Gly Phe Met Leu
            260                 265                 270

CTC CAG TGG TTC TGC TCC AAG ACC TTC ACT GTC AGC TTC TAT AAG CTC      864
Leu Gln Trp Phe Cys Ser Lys Thr Phe Thr Val Ser Phe Tyr Lys Leu
        275                 280                 285

CGC GGC TTC CTC CAC CAG ACC TGG AGC GTG CCC CGC TAC GGC TTC CAG      912
Arg Gly Phe Leu His Gln Thr Trp Ser Val Pro Arg Tyr Gly Phe Gln
    290                 295                 300

TAT TTC ATC CCT TCG GCG AAG AAG GGC ATC AAT GAG ATG ATC GAG CTC      960
Tyr Phe Ile Pro Ser Ala Lys Lys Gly Ile Asn Glu Met Ile Glu Leu
305                 310                 315                 320

GCG ATC CTG AGG GCG GAC AAG ATG GGC GTC AAA GTG CTC AGC CTT GCT     1008
Ala Ile Leu Arg Ala Asp Lys Met Gly Val Lys Val Leu Ser Leu Ala
                325                 330                 335

GCA CTC AAC AAG AAT GAG GCG CTC AAT GGG GGT GGC ACG CTG TTC GTC     1056
Ala Leu Asn Lys Asn Glu Ala Leu Asn Gly Gly Gly Thr Leu Phe Val
            340                 345                 350

CGC AAG CAT CCC GAC CTG CGG GTG AGG GTG GTG CAC GGC AAC ACC CTG     1104
Arg Lys His Pro Asp Leu Arg Val Arg Val Val His Gly Asn Thr Leu
        355                 360                 365
```

```
ACG GCG GCG GTG ATC CTC AAC GAG ATC CCC GGC GAC GTC GCG GAG GTG    1152
Thr Ala Ala Val Ile Leu Asn Glu Ile Pro Gly Asp Val Ala Glu Val
        370                 375                 380

TTC CTC ACC GGT GCG ACG TCG AAG CTC GGC AGA GCC ATC GCT CTC TAC    1200
Phe Leu Thr Gly Ala Thr Ser Lys Leu Gly Arg Ala Ile Ala Leu Tyr
385                 390                 395                 400

TTC TGT AGG AAG AAG ATC AGA GTC TTG ATG CTG ACA CTG TCA ACG GAG    1248
Phe Cys Arg Lys Lys Ile Arg Val Leu Met Leu Thr Leu Ser Thr Glu
                405                 410                 415

AGG TTC ATG AAT ATT CAG AGG GAG GCC CCT GCG GAG TTC CAG CAG TAT    1296
Arg Phe Met Asn Ile Gln Arg Glu Ala Pro Ala Glu Phe Gln Gln Tyr
                420                 425                 430

CTG GTC CAG GTC ACC AAG TAC CAG GCT GCA CAG AAT TGC AAG ACG TGG    1344
Leu Val Gln Val Thr Lys Tyr Gln Ala Ala Gln Asn Cys Lys Thr Trp
                435                 440                 445

ATC GTG GGG AAG TGG CTG TCG CCG AGG GAG CAG CGG TGG GCG CCG GCG    1392
Ile Val Gly Lys Trp Leu Ser Pro Arg Glu Gln Arg Trp Ala Pro Ala
                450                 455                 460

GGG ACG CAC TTC CAC CAG TTC GTG GTG CCG CCG ATC ATC GGG TTC CGG    1440
Gly Thr His Phe His Gln Phe Val Val Pro Pro Ile Ile Gly Phe Arg
465                 470                 475                 480

CGG GAC TGC ACG TAC GGG AAG CTC GCC GCG ATG AGG CTG CCG GAG GAC    1488
Arg Asp Cys Thr Tyr Gly Lys Leu Ala Ala Met Arg Leu Pro Glu Asp
                485                 490                 495

GTG GAG GGG CTG GGG ACG TGC GAG TAC ACC ATG GGC CGC GGC GTC GTG    1536
Val Glu Gly Leu Gly Thr Cys Glu Tyr Thr Met Gly Arg Gly Val Val
                500                 505                 510

CAC GCG TGC CAC GCC GGC GGC GTC GTC CAC TTC CTG GAG GGG TGG GAC    1584
His Ala Cys His Ala Gly Gly Val Val His Phe Leu Glu Gly Trp Asp
                515                 520                 525

CAC CAC GAG GTC GGC GCC ATC GAC GTC GAC CGG ATC GAC GCC GTC TGG    1632
His His Glu Val Gly Ala Ile Asp Val Asp Arg Ile Asp Ala Val Trp
                530                 535                 540

AAC GCC GCG CTC AGG CAC GGC CTC ACG CCG GCG TGAACGCCGG CGACGGCGAC  1685
Asn Ala Ala Leu Arg His Gly Leu Thr Pro Ala
545                 550                 555

GGCGGCTAGT AGTAACTACG TACAGCACGG GGACGCCGAA TAACTTTCGT GTTGTGCGTG  1745

TGTGTCGATC GATTGTACGT TGCATTGTTC GCTCGCCCGG CTAGCTTAAT TAATTATCGG  1805

GCGTGCTTGT GTTGTGTGTT GATAGCTAGC GTCGTACGTA AGAATACCGC AGAAATGACA  1865

AGAAAGAATG GATGATTCCT CGTAAAAAAA AAAAAAAA                          1903

(2) INFORMATION FOR SEQ ID NO:16:

(i) SEQUENCE CHARACTERISTICS:
        (A) LENGTH: 555 amino acids
        (B) TYPE: amino acid
        (D) TOPOLOGY: unknown (ii) MOLECULE TYPE: protein (xi) SEQUENCE DESCRIPTION: SEQ ID NO:16:

Asn Met Leu Phe Phe Thr Arg Arg Arg Val Val Asp Asp Gly Val
 1               5                  10                  15

Asp Phe Arg Gln Ile Asp Thr Glu Trp Asp Trp Asp Asn Met Val Ile
                20                  25                  30

Met Gln Thr Leu Ile Ala Ala Val Leu Val Thr Ser Arg Val Phe Pro
            35                  40                  45

Ala Thr Ser Asp Leu Ser Ala Trp Asp Leu Arg Gly Trp Ala Ile Ala
```

-continued

```
            50                      55                      60
Val Val Leu His Val Ala Val Ser Glu Pro Ala Phe Tyr Trp Ala His
 65                      70                      75                      80
Arg Ala Leu His Leu Gly Pro Leu Phe Ser Arg Tyr His Ser Leu His
                         85                      90                      95
His Ser Phe Gln Ala Thr Gln Ala Leu Thr Ala Gly Phe Val Thr Pro
                        100                     105                     110
Leu Glu Ser Leu Ile Leu Thr Leu Val Ala Trp Pro His Leu Gln Gly
                        115                     120                     125
Leu His Gly Gly Thr Arg Leu Arg Glu Leu Val Tyr Gly His Ile Ser
                        130                     135                     140
Ser Ser Thr Thr Pro Val His Gly Val Gln Gln Arg Arg Gly His Leu
145                     150                     155                     160
Thr Gln Asp Phe Gln Asp Phe Pro Phe Leu Arg Tyr Leu Ile Tyr Thr
                        165                     170                     175
Pro Ser Tyr Leu Ser Leu His His Arg Glu Lys Asp Ser Asn Phe Cys
                        180                     185                     190
Leu Phe Met Pro Leu Phe Asp Ala Leu Gly Gly Thr Leu Asn Pro Lys
                        195                     200                     205
Ser Trp Gln Leu Gln Lys Glu Val Asp Leu Gly Lys Asn His Arg Val
                        210                     215                     220
Pro Asp Phe Val Phe Leu Val His Val Val Asp Val Val Ser Ser Met
225                     230                     235                     240
His Val Pro Phe Ala Phe Arg Ala Cys Ser Ser Leu Pro Phe Ala Thr
                        245                     250                     255
His Leu Val Leu Leu Pro Leu Trp Pro Ile Ala Phe Gly Phe Met Leu
                        260                     265                     270
Leu Gln Trp Phe Cys Ser Lys Thr Phe Thr Val Ser Phe Tyr Lys Leu
                        275                     280                     285
Arg Gly Phe Leu His Gln Thr Trp Ser Val Pro Arg Tyr Gly Phe Gln
                        290                     295                     300
Tyr Phe Ile Pro Ser Ala Lys Lys Gly Ile Asn Glu Met Ile Glu Leu
305                     310                     315                     320
Ala Ile Leu Arg Ala Asp Lys Met Gly Val Lys Val Leu Ser Leu Ala
                        325                     330                     335
Ala Leu Asn Lys Asn Glu Ala Leu Asn Gly Gly Thr Leu Phe Val
                        340                     345                     350
Arg Lys His Pro Asp Leu Arg Val Arg Val Val His Gly Asn Thr Leu
                        355                     360                     365
Thr Ala Ala Val Ile Leu Asn Glu Ile Pro Gly Asp Val Ala Glu Val
                        370                     375                     380
Phe Leu Thr Gly Ala Thr Ser Lys Leu Gly Arg Ala Ile Ala Leu Tyr
385                     390                     395                     400
Phe Cys Arg Lys Lys Ile Arg Val Leu Met Leu Thr Leu Ser Thr Glu
                        405                     410                     415
Arg Phe Met Asn Ile Gln Arg Glu Ala Pro Ala Glu Phe Gln Gln Tyr
                        420                     425                     430
Leu Val Gln Val Thr Lys Tyr Gln Ala Ala Gln Asn Cys Lys Thr Trp
                        435                     440                     445
Ile Val Gly Lys Trp Leu Ser Pro Arg Glu Gln Arg Trp Ala Pro Ala
                        450                     455                     460
Gly Thr His Phe His Gln Phe Val Val Pro Pro Ile Ile Gly Phe Arg
465                     470                     475                     480
```

```
Arg Asp Cys Thr Tyr Gly Lys Leu Ala Ala Met Arg Leu Pro Glu Asp
            485                 490                 495

Val Glu Gly Leu Gly Thr Cys Glu Tyr Thr Met Gly Arg Gly Val Val
        500                 505                 510

His Ala Cys His Ala Gly Gly Val Val His Phe Leu Glu Gly Trp Asp
        515                 520                 525

His His Glu Val Gly Ala Ile Asp Val Asp Arg Ile Asp Ala Val Trp
    530                 535                 540

Asn Ala Ala Leu Arg His Gly Leu Thr Pro Ala
545                 550                 555

(2) INFORMATION FOR SEQ ID NO:17:

(i) SEQUENCE CHARACTERISTICS:
        (A) LENGTH: 2135 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 9..1883

(xi) SEQUENCE DESCRIPTION: SEQ ID NO:17:

ACGGTATA ATG GCC ACA AAA CCA GGA GTC CTC ACC GAT TGG CCT TGG ACA        50
         Met Ala Thr Lys Pro Gly Val Leu Thr Asp Trp Pro Trp Thr
          1               5                  10

CCC CTC GGA AGT TTC AAG TAC ATC GTA ATA GCA CCA TGG GCT GTC CAT        98
Pro Leu Gly Ser Phe Lys Tyr Ile Val Ile Ala Pro Trp Ala Val His
 15               20                  25                  30

AGC ACA TAC AGG TTT GTG ACA GAT GAT CCA GAG AAG AGG GAT CTC GGG       146
Ser Thr Tyr Arg Phe Val Thr Asp Asp Pro Glu Lys Arg Asp Leu Gly
                 35                  40                  45

TAC TTC CTT GTG TTC CCC TTC TTG CTC TTC AGA ATT CTG CAC AAC CAG       194
Tyr Phe Leu Val Phe Pro Phe Leu Leu Phe Arg Ile Leu His Asn Gln
             50                  55                  60

GTT TGG ATC TCT CTG TCC CGT TAC TAT ACG TCC TCG GGA AAG AGA CGC       242
Val Trp Ile Ser Leu Ser Arg Tyr Tyr Thr Ser Ser Gly Lys Arg Arg
         65                  70                  75

ATC GTC GAC AAG GGA ATC GAC TTC AAT CAG GTC GAC AGG GAG ACC AAC       290
Ile Val Asp Lys Gly Ile Asp Phe Asn Gln Val Asp Arg Glu Thr Asn
     80                  85                  90

TGG GAT GAC CAA ATA TTG TTC AAC GGA GTG CTG TTC TAT ATA GGC ATC       338
Trp Asp Asp Gln Ile Leu Phe Asn Gly Val Leu Phe Tyr Ile Gly Ile
 95                 100                 105                 110

AAC CTA TTG GCG GAG GGC AAA CAA CTT CCC TGG TGG AGA ACT GAC GGA       386
Asn Leu Leu Ala Glu Gly Lys Gln Leu Pro Trp Trp Arg Thr Asp Gly
                115                 120                 125

GTG TTG ATG GGA GCG CTT ATT CAC ACC GGA CCG GTG GAG TTC CTC TAT       434
Val Leu Met Gly Ala Leu Ile His Thr Gly Pro Val Glu Phe Leu Tyr
            130                 135                 140

TAT TGG GTC CAC AAA GCT CTC CAC CAT CAC TTT CTT TAT TCC CGC TAC       482
Tyr Trp Val His Lys Ala Leu His His His Phe Leu Tyr Ser Arg Tyr
        145                 150                 155

CAT TCC CAC CAC CAC TCC TCT ATC GTC ACT GAG CCC ATC ACT TCG GTG       530
His Ser His His His Ser Ser Ile Val Thr Glu Pro Ile Thr Ser Val
    160                 165                 170

ATA CAT CCG TTT GCG GAG CAC ATA GCA TAC TTC ATC CTC TTC GCG ATA       578
```

```
                                              -continued

Ile His Pro Phe Ala Glu His Ile Ala Tyr Phe Ile Leu Phe Ala Ile
175                 180                 185                 190

CCA CTA CTT ACC ACG TTG GTA ACA AAA ACG GCG TCA ATA ATT TCG TTC         626
Pro Leu Leu Thr Thr Leu Val Thr Lys Thr Ala Ser Ile Ile Ser Phe
                195                 200                 205

GCC GGA TAC ATA ATC TAC ATA GAC TTC ATG AAC AAC ATG GGA CAC TGC         674
Ala Gly Tyr Ile Ile Tyr Ile Asp Phe Met Asn Asn Met Gly His Cys
                    210                 215                 220

AAC TTC GAG CTA ATC CCT AAG CGC CTT TTC CAC CTC TTT CCT CCC CTC         722
Asn Phe Glu Leu Ile Pro Lys Arg Leu Phe His Leu Phe Pro Pro Leu
                225                 230                 235

AAG TTC CTC TGT TAC ACC CCC TCA TAC CAC TCG CTG CAC CAC ACG CAG         770
Lys Phe Leu Cys Tyr Thr Pro Ser Tyr His Ser Leu His His Thr Gln
240                 245                 250

TTC CGG ACC AAC TAC TCC CTC TTC ATG CCC TTG TAT GAC TAC ATC TAC         818
Phe Arg Thr Asn Tyr Ser Leu Phe Met Pro Leu Tyr Asp Tyr Ile Tyr
255                 260                 265                 270

GGC ACA ATG GAT GAA AGC ACG GAT ACG TTG TAC GAG AAA ACT CTA GAA         866
Gly Thr Met Asp Glu Ser Thr Asp Thr Leu Tyr Glu Lys Thr Leu Glu
                    275                 280                 285

AGA GGA GAT GAT AGA GTG GAC GTG GTG CAC TTA ACT CAC CTG ACG ACG         914
Arg Gly Asp Asp Arg Val Asp Val Val His Leu Thr His Leu Thr Thr
                290                 295                 300

CCA GAA TCC ATA TAC CAT TTG CGC ATT GGC TTG CCC TCA TTT GCC TCC         962
Pro Glu Ser Ile Tyr His Leu Arg Ile Gly Leu Pro Ser Phe Ala Ser
            305                 310                 315

TAC CCC TTC GCT TAT AGA TGG TTC ATG CGC CTT TTG TGG CCT TTC ACC        1010
Tyr Pro Phe Ala Tyr Arg Trp Phe Met Arg Leu Leu Trp Pro Phe Thr
            320                 325                 330

TCT CTC TCC ATG ATA TTC ACG CTC TTC TAC GCC CGC CTC TTT GTC GCT        1058
Ser Leu Ser Met Ile Phe Thr Leu Phe Tyr Ala Arg Leu Phe Val Ala
335                 340                 345                 350

GAG AGA AAC TCC TTC AAC AAG CTC AAC TTG CAG TCT TGG GTG ATA CCT        1106
Glu Arg Asn Ser Phe Asn Lys Leu Asn Leu Gln Ser Trp Val Ile Pro
                355                 360                 365

AGA TAT AAT CTA CAG TAC TTG TTA AAA TGG AGG AAA GAA GCG ATC AAT        1154
Arg Tyr Asn Leu Gln Tyr Leu Leu Lys Trp Arg Lys Glu Ala Ile Asn
            370                 375                 380

AAC ATG ATT GAG AAA GCG ATA CTG GAG GCA GAT AAG AAA GGA GTG AAG        1202
Asn Met Ile Glu Lys Ala Ile Leu Glu Ala Asp Lys Lys Gly Val Lys
            385                 390                 395

GTG CTT AGT CTG GGT CTC ATG AAC CAA GGG GAG GAG CTT AAC AGG AAC        1250
Val Leu Ser Leu Gly Leu Met Asn Gln Gly Glu Glu Leu Asn Arg Asn
400                 405                 410

GGA GAG GTG TAT ATC CAC AAC CAT CCA GAT ATG AAA GTG AGA CTG GTC        1298
Gly Glu Val Tyr Ile His Asn His Pro Asp Met Lys Val Arg Leu Val
415                 420                 425                 430

GAC GGC AGT AGA TTA GCA GCA GCT GTT GTG ATC AAC AGT GTA CCC AAA        1346
Asp Gly Ser Arg Leu Ala Ala Ala Val Val Ile Asn Ser Val Pro Lys
                435                 440                 445

GCA ACT ACA AGC GTC GTG ATG ACA GGC AAT CTC ACT AAG GTT GCC TAC        1394
Ala Thr Thr Ser Val Val Met Thr Gly Asn Leu Thr Lys Val Ala Tyr
                450                 455                 460

ACC ATC GCC TCT GCT CTC TGC CAG AGA GGC GTT CAG GTC TCC ACT CTG        1442
Thr Ile Ala Ser Ala Leu Cys Gln Arg Gly Val Gln Val Ser Thr Leu
            465                 470                 475

CGC CTA GAC GAG TAT GAG AAA ATA AGA TCA TGC GTT CCA CAA GAA TGC        1490
Arg Leu Asp Glu Tyr Glu Lys Ile Arg Ser Cys Val Pro Gln Glu Cys
480                 485                 490
```

```
AGA GAC CAT TTG GTC TAT TTA ACC TCT GAA GCA CTC TCA TCA AAC AAG      1538
Arg Asp His Leu Val Tyr Leu Thr Ser Glu Ala Leu Ser Ser Asn Lys
495                 500                 505                 510

GTA TGG CTG GTG GGA GAA GGA ACA ACA AGA GAA GAG CAG GAA AAA GCC      1586
Val Trp Leu Val Gly Glu Gly Thr Thr Arg Glu Glu Gln Glu Lys Ala
                515                 520                 525

ACA AAA GGG ACA TTG TTT ATA CCA TTC TCA CAG TTC CCC CTC AAG CAG      1634
Thr Lys Gly Thr Leu Phe Ile Pro Phe Ser Gln Phe Pro Leu Lys Gln
            530                 535                 540

TTA CGT AGC GAT TGT ATC TAT CAT ACC ACA CCA GCA TTG ATA GTT CCA      1682
Leu Arg Ser Asp Cys Ile Tyr His Thr Thr Pro Ala Leu Ile Val Pro
        545                 550                 555

AAA TCT CTG GTG AAT GTC CAC TCC TGT GAG AAC TGG TTA CCG AGA AAG      1730
Lys Ser Leu Val Asn Val His Ser Cys Glu Asn Trp Leu Pro Arg Lys
    560                 565                 570

GCG ATG AGT GCA ACT AGA GTG GCC GGC ATA TTG CAC GCC TTA GAA GGA      1778
Ala Met Ser Ala Thr Arg Val Ala Gly Ile Leu His Ala Leu Glu Gly
575                 580                 585                 590

TGG GAA ACG CAT GAG TGT GGC ACA TCC CTT CTT CTC TCG GAT TTG GAC      1826
Trp Glu Thr His Glu Cys Gly Thr Ser Leu Leu Leu Ser Asp Leu Asp
                595                 600                 605

AAA GTA TGG GAA GCC TGT CTC AGC CAC GGC TTC CAG CCT CTC CTC CTT      1874
Lys Val Trp Glu Ala Cys Leu Ser His Gly Phe Gln Pro Leu Leu Leu
            610                 615                 620

CCA CAT CAT TAAAACTCCA ACCTTGGAAG ATTTTTGGAG AATGAGAGCG              1923
Pro His His
        625

ACACGCTCTG TGCTTCTTTT CCTTATGATC CAGCTCTTCC ACGCACACAT GAACTATGAA   1983

ACATATATAA AGCGCACACA TTTTATGTTT TACGCACACA TATATTTATG CATATCAAGC   2043

TTTTGGTGAT TATGGTATTG ATAGAGTCAA ATTAAGCTCG GTGACTATGG TATTAATAAG   2103

AGTACTATTT CCTTAAAAAA AAAAAAAAAA AA                                 2135

(2) INFORMATION FOR SEQ ID NO:18:

(i) SEQUENCE CHARACTERISTICS:
        (A) LENGTH: 625 amino acids
        (B) TYPE: amino acid
        (D) TOPOLOGY: unknown (ii) MOLECULE TYPE: protein (xi) SEQUENCE DESCRIPTION: SEQ ID NO:18:

Met Ala Thr Lys Pro Gly Val Leu Thr Asp Trp Pro Trp Thr Pro Leu
 1               5                  10                  15

Gly Ser Phe Lys Tyr Ile Val Ile Ala Pro Trp Ala Val His Ser Thr
                20                  25                  30

Tyr Arg Phe Val Thr Asp Asp Pro Glu Lys Arg Asp Leu Gly Tyr Phe
            35                  40                  45

Leu Val Phe Pro Phe Leu Leu Phe Arg Ile Leu His Asn Gln Val Trp
    50                  55                  60

Ile Ser Leu Ser Arg Tyr Tyr Thr Ser Ser Gly Lys Arg Arg Ile Val
65                  70                  75                  80

Asp Lys Gly Ile Asp Phe Asn Gln Val Asp Arg Glu Thr Asn Trp Asp
                85                  90                  95

Asp Gln Ile Leu Phe Asn Gly Val Leu Phe Tyr Ile Gly Ile Asn Leu
            100                 105                 110

Leu Ala Glu Gly Lys Gln Leu Pro Trp Trp Arg Thr Asp Gly Val Leu
    115                 120                 125
```

```
Met Gly Ala Leu Ile His Thr Gly Pro Val Glu Phe Leu Tyr Tyr Trp
    130                 135                 140

Val His Lys Ala Leu His His His Phe Leu Tyr Ser Arg Tyr His Ser
145                 150                 155                 160

His His His Ser Ser Ile Val Thr Glu Pro Ile Thr Ser Val Ile His
                165                 170                 175

Pro Phe Ala Glu His Ile Ala Tyr Phe Ile Leu Phe Ala Ile Pro Leu
            180                 185                 190

Leu Thr Thr Leu Val Thr Lys Thr Ala Ser Ile Ile Ser Phe Ala Gly
            195                 200                 205

Tyr Ile Ile Tyr Ile Asp Phe Met Asn Asn Met Gly His Cys Asn Phe
210                 215                 220

Glu Leu Ile Pro Lys Arg Leu Phe His Leu Phe Pro Pro Leu Lys Phe
225                 230                 235                 240

Leu Cys Tyr Thr Pro Ser Tyr His Ser Leu His His Thr Gln Phe Arg
                245                 250                 255

Thr Asn Tyr Ser Leu Phe Met Pro Leu Tyr Asp Tyr Ile Tyr Gly Thr
            260                 265                 270

Met Asp Glu Ser Thr Asp Thr Leu Tyr Glu Lys Thr Leu Glu Arg Gly
            275                 280                 285

Asp Asp Arg Val Asp Val Val His Leu Thr His Leu Thr Pro Glu
290                 295                 300

Ser Ile Tyr His Leu Arg Ile Gly Leu Pro Ser Phe Ala Ser Tyr Pro
305                 310                 315                 320

Phe Ala Tyr Arg Trp Phe Met Arg Leu Leu Trp Pro Phe Thr Ser Leu
                325                 330                 335

Ser Met Ile Phe Thr Leu Phe Tyr Ala Arg Leu Phe Val Ala Glu Arg
                340                 345                 350

Asn Ser Phe Asn Lys Leu Asn Leu Gln Ser Trp Val Ile Pro Arg Tyr
                355                 360                 365

Asn Leu Gln Tyr Leu Leu Lys Trp Arg Lys Glu Ala Ile Asn Asn Met
            370                 375                 380

Ile Glu Lys Ala Ile Leu Glu Ala Asp Lys Lys Gly Val Lys Val Leu
385                 390                 395                 400

Ser Leu Gly Leu Met Asn Gln Gly Glu Glu Leu Asn Arg Asn Gly Glu
                405                 410                 415

Val Tyr Ile His Asn His Pro Asp Met Lys Val Arg Leu Val Asp Gly
            420                 425                 430

Ser Arg Leu Ala Ala Ala Val Val Ile Asn Ser Val Pro Lys Ala Thr
            435                 440                 445

Thr Ser Val Val Met Thr Gly Asn Leu Thr Lys Val Ala Tyr Thr Ile
    450                 455                 460

Ala Ser Ala Leu Cys Gln Arg Gly Val Gln Val Ser Thr Leu Arg Leu
465                 470                 475                 480

Asp Glu Tyr Glu Lys Ile Arg Ser Cys Val Pro Gln Glu Cys Arg Asp
                485                 490                 495

His Leu Val Tyr Leu Thr Ser Glu Ala Leu Ser Ser Asn Lys Val Trp
            500                 505                 510

Leu Val Gly Glu Gly Thr Thr Arg Glu Glu Gln Glu Lys Ala Thr Lys
            515                 520                 525

Gly Thr Leu Phe Ile Pro Phe Ser Gln Phe Pro Leu Lys Gln Leu Arg
            530                 535                 540
```

```
Ser Asp Cys Ile Tyr His Thr Thr Pro Ala Leu Ile Val Pro Lys Ser
545                 550                 555                 560

Leu Val Asn Val His Ser Cys Glu Asn Trp Leu Pro Arg Lys Ala Met
                565                 570                 575

Ser Ala Thr Arg Val Ala Gly Ile Leu His Ala Leu Glu Gly Trp Glu
                580                 585                 590

Thr His Glu Cys Gly Thr Ser Leu Leu Leu Ser Asp Leu Asp Lys Val
                595                 600                 605

Trp Glu Ala Cys Leu Ser His Gly Phe Gln Pro Leu Leu Leu Pro His
    610                 615                 620

His
625

(2) INFORMATION FOR SEQ ID NO:19:

(i) SEQUENCE CHARACTERISTICS:
         (A) LENGTH: 1407 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:19:
```

| | | | | | |
|---|---|---|---|---|---|
| CACAAAAATA | AAATGGAGGG | AAGCCCAGTG | ACCAGTGTCA | GGCTCTCTTC | GGTGGTGCCT | 60 |
| GCTTCTGTGG | TAGGTGAGAA | CAAGCCACGA | CAGCTCACAC | CCATGGACTT | AGCCATGAAG | 120 |
| CTCCACTACG | TCCGAGCCGT | CTACTTCTTC | AAGGGTGCAC | GTGACTTCAC | TGTCGCCGAC | 180 |
| GTGAAGAACA | CCATGTTTAC | TCTACAGTCT | CTACTCCAAT | CTTATCACCA | CGTCTCAGGT | 240 |
| CGGATCCGGA | TGTCCGACAA | CGACAACGAC | ACTTCAGCTG | CAGCCATACC | TTACATTCGC | 300 |
| TGCAACGACA | GTGGCATACG | CGTGGTCGAG | GCCAACGTCG | AAGAGTTCAC | AGTGGAGAAG | 360 |
| TGGCTCGAGT | TGGACGACCG | TTCCATTGAC | CACCGATTCC | TTGTCTACGA | TCACGTTCTT | 420 |
| GGTCCTGATC | TTACCTTCTC | GCCACTCGTT | TTCCTCCAGA | TAACTCAGTT | TAAATGTGGT | 480 |
| GGGCTCTGTA | TTGGGTTGAG | TTGGGCCCAT | ATTCTTGGAG | ACGTGTTTTC | AGCATCAACG | 540 |
| TTCATGAAAA | CACTTGGACA | GCTGGTATCG | GGTCATGCCC | CAACAAAACC | GGTTTACCCG | 600 |
| AAAACCCCCG | AACTAACCTC | TCATGCTCGT | AATGATGGTG | AAGCTATTTC | CATTGAAAAG | 660 |
| ATAGATTCGG | TTGGCGAGTA | TTGGTTACTT | ACCAATAAAT | GCAAGATGGG | GAGACACATT | 720 |
| TTTAATTTTA | GCCTCAACCA | CATTGATAGC | TTGATGGCCA | AGTACACCAC | GCGAGACCAA | 780 |
| CCTTTCTCGG | AGGTTGATAT | TTTGTATGCA | TTGATATGGA | AGTCGCTACT | GAATATCCGC | 840 |
| GGCGAAACAA | ACACGAATGT | TATAACAATT | TGTGACCGTA | AAAAGTCTTC | AACCTGTTGG | 900 |
| AACGAGGACT | TGGTAATAAG | CGTAGTGGAA | AAGAATGACG | AAATGGTTGG | GATATCCGAA | 960 |
| CTAGCTGCAC | TGATTGCTGG | TGAAAAAAGA | GAAGAAAACG | GTGCGATCAA | GAGGATGATA | 1020 |
| GAACAAGATA | AAGGCTCTTC | GGATTTTTTC | ACGTACGGTG | CAAATTTAAC | GTTTGTGAAT | 1080 |
| CTTGATGAAA | TAGATATGTA | TGAACTTGAG | ATCAACGGAG | GGAAGCCGGA | TTTCGTAAAC | 1140 |
| TACACGATTC | ATGGGGTCGG | AGACAAAGGT | GTTGTTTTGG | TTTTTCCCAA | GCAAAACTTT | 1200 |
| GCAAGGATTG | TAAGTGTAGT | GATGCCTGAA | GAAGACCTTG | CAAAACTCAA | GGAGGAGGTG | 1260 |
| ACTAATATGA | TTATATAACT | TTGTATCTTC | TTCTTGTTGT | TATACATAAA | TGCTGTTTTT | 1320 |
| TACTCTTTGT | AATTTCATTA | TCGAATTGTT | GGGAAGCCTA | TCAATAAATT | GTTTGAACTG | 1380 |
| TTTAAAAAAA | AAAAAAAAAA | AAAAAA | | | | 1407 |

(2) INFORMATION FOR SEQ ID NO:20:

(i) SEQUENCE CHARACTERISTICS:
        (A) LENGTH: 2539 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

```
GAGGGCGCAA TTAGGAGTAG ATTGGTTGGC AATAGGGATG TTCTCTACCA AAAATTTTAC        60
TGTTTTTTCG CAAGATTTAG TTATCGTACA ATTATGTAAA ATCATTATCA GGAAATTTGT       120
TGCATGATTG TGTTTGAGGT GGAAATGAAC CGCATCCGTA TTAAGATCAT TTTTGCTGGT       180
GGAAACAATG TTACCAGGAA ACTGAACTTG GTTTTTTATA GATTAATGTG ACTTGTTAGG       240
TACCGTAATA TAATACTAGT TGGCTACGAC ACGTACATGT GCGTTTATTG CTTGAAGCCA       300
ATAAGGACAA GGTGGACGTA ATAAAGTGTG CTTGTTGTTG GATGGATCTG AATATGATGA       360
CTCAACTGTC CAACTCTAAT GTTGTTGCTA AAGACCCAAA TCCCACCCAC ATTTAATGTT       420
GCCGTCACGG AAACAGTTTT CCCAACTGTC CTAAATCAGT GATACCCATG CCTATTCTGA       480
ACTCAACTCT CTTTCGAAAC TCAATCCTTA TATAACACAT CCCATTTAAG CCTATAAGCT       540
ACACATATCA GCTCTCTCAC AAAAATAAAA TGGAGGGAAG CCCAGTGACC AGTGTCAGGC       600
TCTCTTCGGT GGTGCCTGCT TCTGTGGTAG GTGAGAACAA GCCACGACAG CTCACACCCA       660
TGGACTTAGC CATGAAGCTC CACTACGTCC GAGCCGTCTA CTTCTTCAAG GGTGCACGTG       720
ACTTCACTGT CGCCGACGTG AAGAACACCA TGTTTACTCT ACAGTCTCTA CTCCAATCTT       780
ATCACCACGT CTCAGGTCGG ATCCGGATGT CCGACAACGA CAACGACACT TCAGCTGCAG       840
CCATACCTTA CATTCGCTGC AACGACAGTG GCATACGCGT GGTCGAGGCC AACGTCGAAG       900
AGTTCACAGT GGAGAAGTGG CTCGAGTTGG ACGACCGTTC CATTGACCAC CGATTCCTTG       960
TCTACGATCA CGTTCTTGGT CCTGATCTTA CCTTCTCGCC ACTCGTTTTC CTCCAGGTAA      1020
ACACACATAC ACAAATTTTA GTATAATATA ATGGATTATT TAAGTTCACA TGCAACGAAA      1080
ACGGCTGATT CTCCCACGAA CTTAGTTTCT TTCTTAGTTA CTAACTATCA AACATTCGTT      1140
TCAAATTCTT TCCAATCATT AGCTTAATTA ATAATTATGA AATGAATATT TAATATAACC      1200
GTGGAACTTG AAGAGAAAAT ATTTTTTACA TGTGAAATTG ATTCTTCACT ATATATGATC      1260
AGGTTAGATT CTGTGTGTGT GTGTGTGTGT GTTTTTTTTT TGTCCAAATC AGGCTAGCTA      1320
GAGTAAACTA AATTTTTTAC TTTGAAATTC GTTTTTCAGA TAACTCAGTT TAAATGTGGT      1380
GGGCTCTGTA TTGGGTTGAG TTGGGCCCAT ATTCTTGGAG ACGTGTTTTC AGCATCAACG      1440
TTCATGAAAA CACTTGGACA GCTGGTATCG GGTCATGCCC CAACAAAACC GGTTTACCCG      1500
AAAACCCCCG AACTAACCTC TCATGCTCGT AATGATGGTG AAGCTATTTC CATTGAAAAG      1560
ATAGATTCGG TTGGCGAGTA TTGGTTACTT ACCAATAAAT GCAAGATGGG GAGACACATT      1620
TTTAATTTTA GCCTCAACCA CATTGATAGC TTGATGGCCA AGTACACCAC GCGAGACCAA      1680
CCTTTCTCGG AGGTTGATAT TTTGTATGCA TTGATATGGA AGTCGCTACT GAATATCCGC      1740
GGCGAAACAA ACACGAATGT TATAACAATT TGTGACCGTA AAAGTCTTC AACCTGTTGG       1800
AACGAGGACT TGGTAATAAG CGTAGTGGAA AAGAATGACG AAATGGTTGG GATATCCGAA      1860
CTAGCTGCAC TGATTGCTGG TGAAAAAAGA GAAGAAAACG GTGCGATCAA GAGGATGATA      1920
GAACAAGATA AAGGCTCTTC GGATTTTTTC ACGTACGGTG CAAATTTAAC GTTTGTGAAT      1980
```

-continued

```
CTTGATGAAA TAGATATGTA TGAACTTGAG ATCAACGGAG GGAAGCCGGA TTTCGTAAAC      2040

TACACGATTC ATGGGGTCGG AGATAAAGGT GTTGTTTTGG TTTTTCCCAA GCAAAACTTT      2100

GCAAGGATTG TAAGTGTAGT GATGCCTGAA GAAGACCTTG CAAAACTCAA GGAGGAGGTG      2160

ACTAATATGA TTATATAACT TTGTATCTTC TTCTTGTTGT TATACATAAA TGCTGTTTTT      2220

TACTCTTTGT AATTTCATTA TCGAATTGTT GGGAAGCCTA TCAATAAATT GTTTGAACTG      2280

TTTACTTTTC CTGTCGCTTT ATTATTGCGT CACACCATCC AAAGTTTACA ATGTGGACTC      2340

TTCTATTTTC TACTCCGTAA AATCAACTTT AGAGCTATCA AGATTGGATC ATTTGCATGG      2400

GATTTGGAGT GAAAAGATAA ATTGTTCTTG TTTGGTGTCA CTGATTCACA ATGATGATCC      2460

ACTATCGACA GTAGAAAGCA TGATGATGAA ATCTTGGGTA TCTTCTCTCA ATTTTATCAC      2520

TCTCACAGAT TTATTTTGT                                                  2539
```

(2) INFORMATION FOR SEQ ID NO:21:

(i) SEQUENCE CHARACTERISTICS:
        (A) LENGTH: 2040 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 270..716

(ix) FEATURE:
        (A) NAME/KEY: CDS
        (B) LOCATION: 1060..1875

(xi) SEQUENCE DESCRIPTION: SEQ ID NO:21:

```
ATAAGGACAA GGTGGACGTA ATAAAGTGTG CTTGTTGTTG GATGGATCTG AATATGATGA       60

CTCAACTGTC CAACTCTAAT GTTGTTGCTA AAGACCCAAA TCCCACCCAC ATTTAATGTT      120

GCCGTCACGG AAACAGTTTT CCCAACTGTC CTAAATCAGT GATACCCATG CCTATTCTGA      180

ACTCAACTCT CTTTCGAAAC TCAATCCTTA TATAACACAT CCCATTTAAG CCTATAAGCT      240

ACACATATCA GCTCTCTCAC AAAAATAAA ATG GAG GGA AGC CCA GTG ACC AGT        293
                                  Met Glu Gly Ser Pro Val Thr Ser
                                   1               5

GTC AGG CTC TCT TCG GTG GTG CCT GCT TCT GTG GTA GGT GAG AAC AAG        341
Val Arg Leu Ser Ser Val Val Pro Ala Ser Val Gly Glu Asn Lys
         10              15                  20

CCA CGA CAG CTC ACA CCC ATG GAC TTA GCC ATG AAG CTC CAC TAC GTC        389
Pro Arg Gln Leu Thr Pro Met Asp Leu Ala Met Lys Leu His Tyr Val
 25              30                  35                  40

CGA GCC GTC TAC TTC TTC AAG GGT GCA CGT GAC TTC ACT GTC GCC GAC        437
Arg Ala Val Tyr Phe Phe Lys Gly Ala Arg Asp Phe Thr Val Ala Asp
                 45                  50                  55

GTG AAG AAC ACC ATG TTT ACT CTA CAG TCT CTA CTC CAA TCT TAT CAC        485
Val Lys Asn Thr Met Phe Thr Leu Gln Ser Leu Leu Gln Ser Tyr His
         60                  65                  70

CAC GTC TCA GGT CGG ATC CGG ATG TCC GAC AAC GAC AAC GAC ACT TCA        533
His Val Ser Gly Arg Ile Arg Met Ser Asp Asn Asp Asn Asp Thr Ser
     75                  80                  85

GCT GCA GCC ATA CCT TAC ATT CGC TGC AAC GAC AGT GGC ATA CGC GTG        581
Ala Ala Ala Ile Pro Tyr Ile Arg Cys Asn Asp Ser Gly Ile Arg Val
 90                  95                 100

GTC GAG GCC AAC GTC GAA GAG TTC ACA GTG GAG AAG TGG CTC GAG TTG        629
Val Glu Ala Asn Val Glu Glu Phe Thr Val Glu Lys Trp Leu Glu Leu
```

```
                105                 110                 115                 120
GAC GAC CGT TCC ATT GAC CAC CGA TTC CTT GTC TAC GAT CAC GTT CTT            677
Asp Asp Arg Ser Ile Asp His Arg Phe Leu Val Tyr Asp His Val Leu
                125                 130                 135

GGT CCT GAT CTT ACC TTC TCG CCA CTC GTT TTC CTC CAG GTAAACACAC            726
Gly Pro Asp Leu Thr Phe Ser Pro Leu Val Phe Leu Gln
            140                 145

ATACACAAAT TTTAGTATAA TATAATGGAT TATTTAAGTT CACATGCAAC GAAAACGGCT         786

GATTCTCCCA CGAACTTAGT TTCTTTCTTA GTTACTAACT ATCAAACATT CGTTTCAAAT         846

TCTTTCCAAT CATTAGCTTA ATTAATAATT ATGAAATGAA TATTTAATAT AACCGTGGAA         906

CTTGAAGAGA AAATATTTTT TACATGTGAA ATTGATTCTT CACTATATAT GATCAGGTTA         966

GATTCTGTGT GTGTGTGTGT GTGTGTTTTT TTTTTGTCCA AATCAGGCTA GCTAGAGTAA        1026

ACTAAATTTT TTACTTTGAA ATTCGTTTTT CAG ATA ACT CAG TTT AAA TGT GGT        1080
                                    Ile Thr Gln Phe Lys Cys Gly
                                     1                   5

GGG CTC TGT ATT GGG TTG AGT TGG GCC CAT ATT CTT GGA GAC GTG TTT         1128
Gly Leu Cys Ile Gly Leu Ser Trp Ala His Ile Leu Gly Asp Val Phe
            10                  15                  20

TCA GCA TCA ACG TTC ATG AAA ACA CTT GGA CAG CTG GTA TCG GGT CAT         1176
Ser Ala Ser Thr Phe Met Lys Thr Leu Gly Gln Leu Val Ser Gly His
        25                  30                  35

GCC CCA ACA AAA CCG GTT TAC CCG AAA ACC CCC GAA CTA ACC TCT CAT         1224
Ala Pro Thr Lys Pro Val Tyr Pro Lys Thr Pro Glu Leu Thr Ser His
40                  45                  50                  55

GCT CGT AAT GAT GGT GAA GCT ATT TCC ATT GAA AAG ATA GAT TCG GTT         1272
Ala Arg Asn Asp Gly Glu Ala Ile Ser Ile Glu Lys Ile Asp Ser Val
                60                  65                  70

GGC GAG TAT TGG TTA CTT ACC AAT AAA TGC AAG ATG GGG AGA CAC ATT         1320
Gly Glu Tyr Trp Leu Leu Thr Asn Lys Cys Lys Met Gly Arg His Ile
            75                  80                  85

TTT AAT TTT AGC CTC AAC CAC ATT GAT AGC TTG ATG GCC AAG TAC ACC         1368
Phe Asn Phe Ser Leu Asn His Ile Asp Ser Leu Met Ala Lys Tyr Thr
        90                  95                  100

ACG CGA GAC CAA CCT TTC TCG GAG GTT GAT ATT TTG TAT GCA TTG ATA         1416
Thr Arg Asp Gln Pro Phe Ser Glu Val Asp Ile Leu Tyr Ala Leu Ile
    105                 110                 115

TGG AAG TCG CTA CTG AAT ATC CGC GGC GAA ACA AAC ACG AAT GTT ATA         1464
Trp Lys Ser Leu Leu Asn Ile Arg Gly Glu Thr Asn Thr Asn Val Ile
120                 125                 130                 135

ACA ATT TGT GAC CGT AAA AAG TCT TCA ACC TGT TGG AAC GAG GAC TTG         1512
Thr Ile Cys Asp Arg Lys Lys Ser Ser Thr Cys Trp Asn Glu Asp Leu
                140                 145                 150

GTA ATA AGC GTA GTG GAA AAG AAT GAC GAA ATG GTT GGG ATA TCC GAA         1560
Val Ile Ser Val Val Glu Lys Asn Asp Glu Met Val Gly Ile Ser Glu
            155                 160                 165

CTA GCT GCA CTG ATT GCT GGT GAA AAA AGA GAA GAA AAC GGT GCG ATC         1608
Leu Ala Ala Leu Ile Ala Gly Glu Lys Arg Glu Glu Asn Gly Ala Ile
        170                 175                 180

AAG AGG ATG ATA GAA CAA GAT AAA GGC TCT TCG GAT TTT TTC ACG TAC         1656
Lys Arg Met Ile Glu Gln Asp Lys Gly Ser Ser Asp Phe Phe Thr Tyr
    185                 190                 195

GGT GCA AAT TTA ACG TTT GTG AAT CTT GAT GAA ATA GAT ATG TAT GAA         1704
Gly Ala Asn Leu Thr Phe Val Asn Leu Asp Glu Ile Asp Met Tyr Glu
200                 205                 210                 215

CTT GAG ATC AAC GGA GGG AAG CCG GAT TTC GTA AAC TAC ACG ATT CAT         1752
Leu Glu Ile Asn Gly Gly Lys Pro Asp Phe Val Asn Tyr Thr Ile His
                220                 225                 230
```

```
GGG GTC GGA GAT AAA GGT GTT GTT TTG GTT TTT CCC AAG CAA AAC TTT        1800
Gly Val Gly Asp Lys Gly Val Val Leu Val Phe Pro Lys Gln Asn Phe
            235                 240                 245

GCA AGG ATT GTA AGT GTA GTG ATG CCT GAA GAA GAC CTT GCA AAA CTC        1848
Ala Arg Ile Val Ser Val Val Met Pro Glu Glu Asp Leu Ala Lys Leu
            250                 255                 260

AAG GAG GAG GTG ACT AAT ATG ATT ATA TAACTTTGTA TCTTCTTCTT              1895
Lys Glu Glu Val Thr Asn Met Ile Ile
            265                 270

GTTGTTATAC ATAAATGCTG TTTTTTACTC TTTGTAATTT CATTATCGAA TTGTTGGGAA      1955

GCCTATCAAT AAATTGTTTG AACTGTTTAC TTTTCCTGTC GCTTTATTAT TGCGTCACAC      2015

CATCCAAAGT TTACAATGTG GACTC                                            2040

(2) INFORMATION FOR SEQ ID NO:22:

(i) SEQUENCE CHARACTERISTICS:
        (A) LENGTH: 149 amino acids
        (B) TYPE: amino acid
        (D) TOPOLOGY: unknown (ii) MOLECULE TYPE: protein (xi) SEQUENCE DESCRIPTION: SEQ ID NO:22:

Met Glu Gly Ser Pro Val Thr Ser Val Arg Leu Ser Val Val Pro
  1               5                  10                  15

Ala Ser Val Val Gly Glu Asn Lys Pro Arg Gln Leu Thr Pro Met Asp
                 20                  25                  30

Leu Ala Met Lys Leu His Tyr Val Arg Ala Val Tyr Phe Phe Lys Gly
             35                  40                  45

Ala Arg Asp Phe Thr Val Ala Asp Val Lys Asn Thr Met Phe Thr Leu
         50                  55                  60

Gln Ser Leu Leu Gln Ser Tyr His His Val Ser Gly Arg Ile Arg Met
 65                  70                  75                  80

Ser Asp Asn Asp Asn Asp Thr Ser Ala Ala Ala Ile Pro Tyr Ile Arg
                 85                  90                  95

Cys Asn Asp Ser Gly Ile Arg Val Val Glu Ala Asn Val Glu Glu Phe
                100                 105                 110

Thr Val Glu Lys Trp Leu Glu Leu Asp Asp Arg Ser Ile Asp His Arg
            115                 120                 125

Phe Leu Val Tyr Asp His Val Leu Gly Pro Asp Leu Thr Phe Ser Pro
        130                 135                 140

Leu Val Phe Leu Gln
145

(2) INFORMATION FOR SEQ ID NO:23:

(i) SEQUENCE CHARACTERISTICS:
        (A) LENGTH: 272 amino acids
        (B) TYPE: amino acid
        (D) TOPOLOGY: unknown (ii) MOLECULE TYPE: protein (xi) SEQUENCE DESCRIPTION: SEQ ID NO:23:

Ile Thr Gln Phe Lys Cys Gly Gly Leu Cys Ile Gly Leu Ser Trp Ala
  1               5                  10                  15

His Ile Leu Gly Asp Val Phe Ser Ala Ser Thr Phe Met Lys Thr Leu
                 20                  25                  30
```

-continued

```
Gly Gln Leu Val Ser Gly His Ala Pro Thr Lys Pro Val Tyr Pro Lys
         35                  40                  45

Thr Pro Glu Leu Thr Ser His Ala Arg Asn Asp Gly Glu Ala Ile Ser
 50                  55                  60

Ile Glu Lys Ile Asp Ser Val Gly Glu Tyr Trp Leu Leu Thr Asn Lys
 65                  70                  75                  80

Cys Lys Met Gly Arg His Ile Phe Asn Phe Ser Leu Asn His Ile Asp
                 85                  90                  95

Ser Leu Met Ala Lys Tyr Thr Thr Arg Asp Gln Pro Phe Ser Glu Val
            100                 105                 110

Asp Ile Leu Tyr Ala Leu Ile Trp Lys Ser Leu Leu Asn Ile Arg Gly
            115                 120                 125

Glu Thr Asn Thr Asn Val Ile Thr Ile Cys Asp Arg Lys Lys Ser Ser
            130                 135                 140

Thr Cys Trp Asn Glu Asp Leu Val Ile Ser Val Val Glu Lys Asn Asp
145                 150                 155                 160

Glu Met Val Gly Ile Ser Glu Leu Ala Ala Leu Ile Ala Gly Glu Lys
                165                 170                 175

Arg Glu Glu Asn Gly Ala Ile Lys Arg Met Ile Glu Gln Asp Lys Gly
                180                 185                 190

Ser Ser Asp Phe Phe Thr Tyr Gly Ala Asn Leu Thr Phe Val Asn Leu
            195                 200                 205

Asp Glu Ile Asp Met Tyr Glu Leu Glu Ile Asn Gly Gly Lys Pro Asp
            210                 215                 220

Phe Val Asn Tyr Thr Ile His Gly Val Gly Asp Lys Gly Val Val Leu
225                 230                 235                 240

Val Phe Pro Lys Gln Asn Phe Ala Arg Ile Val Ser Val Val Met Pro
                245                 250                 255

Glu Glu Asp Leu Ala Lys Leu Lys Glu Glu Val Thr Asn Met Ile Ile
            260                 265                 270
```

(2) INFORMATION FOR SEQ ID NO:24:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

AGGTGGACGT AATAAAGTGT G                                    21

(2) INFORMATION FOR SEQ ID NO:25:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

GGTGGTGCCT GCTTCTTTGG TA                                 22

(2) INFORMATION FOR SEQ ID NO:26:

(i) SEQUENCE CHARACTERISTICS:

-continued

```
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

AAATCGAACC ACTTCCCCAC TG                                              22

(2) INFORMATION FOR SEQ ID NO:27:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

GAGGATGATA GAACAAGATA AAGG                                            24

(2) INFORMATION FOR SEQ ID NO:28:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:28:

GGCATCACTA CACTTACAAT CCT                                             23

(2) INFORMATION FOR SEQ ID NO:29:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

CAGTGACACC AAACAAGAAC AA                                              22

(2) INFORMATION FOR SEQ ID NO:30:

(i) SEQUENCE CHARACTERISTICS:
        (A) LENGTH: 6343 bases
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Zea mays
         (C) INDIVIDUAL ISOLATE: Z.mays Glossy2 locus DNA (xi) SEQUENCE DESCRIPTION: SEQ ID NO:30:

TCTAGAAACA ACTTCGAGAT GAGTTTTATC TATTGATGAG GAACCTGTTA AGAAATGTTT     60

GATTCGCATG TAGCTGCAAG GAATGCTAAC TTTTTTTTTT GGTTCATCTT GCCTGTTTCA    120

TAAATGTGCA TACCTTCCTT GCTGTTAGGG AGCTTTACAA CAACAACATA AGTGGGACAA    180
```

```
TACCTCCTAA ACTAGGGAAC CTGACTAACC TGGTCAGTTG TATATTCCCC TCTTTTTTAT      240

TAGTGAATAA AGATATCCAA AAAACTTGAA ATGCACTACC TCTATTTTAT TATTTGGTTT      300

TTATGATGAA AACTTTTTTT TTACTTTTCT GGNTTTATTG TGACTGTAGT ATAAGACAGC      360

ATGGGCTCTC TCAAATATTG TCTCTGCGGA TGACGCTATT GTCAGTTATA AATATTGGCG      420

GCATATTAGG AAACAAATNA TCCCTATTTG AGTTGCGCAC ACATATCATG TTATTATTGT      480

GAATTTGTGA GATATTGAGG TTGATGATAT ATATGTNGNT CATTTTCATG TGGTCGTATG      540

CACTAACAGA TATCGAATAA TTTATACGCG TCGAACGCA CGGGCACATA CATAGTNACA       600

ATTTAAGTGG CCAGATTACA CTTTCTTCTT CGGGGTGATT TTTAACTAAA CATCTAACAA      660

TGCGTGGAGA CGATGTTGCT CATGCTGAAA TAGTACTACC AGCTTCTGTC GTAGCAATCT      720

GTGATGAGAC ACCTCCAGCC CTCCAGTCAC CACTTCTTCA GTCCTTGTAA TAGGAACCAC      780

TTCATCAGTA TGCTCTTGTA TTAGGAACCA CTTCATCAGT ATGTTACTGT CATATAGCTC      840

GAAGCTCTTT AGGAACCACT TCATCAGTAG TTACCCGTGA ACTATCTCGT GTACATGCAA      900

CCTATAGAGC ATAATGGAAT TAAATAGTTG TGACCTCACC ACATAAGAAT CTAACTAGGT      960

ATATGCTCAT GTGTTGCTAT GATAAAATAC ATTAATATAC AAAAAATATT GTGTTTTATA     1020

ATATTAACTC CGTAGCAACG CACGAGCATA TACATATAAC ACACACACAT GTACATAAGT     1080

TATCGNGTTA TTTATACGGTT TCGTTGCAAC GCACGGGCAC TTACCTAGTA TAGTATGAGG    1140

GAAGCACATT CGTGTGTTGC AGAATGCAGA CTACCAGCTG TCCAGCCCTC CCTCATTCAA     1200

GACGTGTGGG GTTTGCTCCT CCGATCGAGT GGACGCACCN GTTTTTTCAG GCCTAATTAT     1260

GGTGCAGTGC AGTGNAGCCG CTCTCCTGCC TGTCCTCCCC GTGGTTCGTT CCCTCGCCGG     1320

ACCACCGTGG GGCCGGTAGC CGCTGCCTGC TTGTTACTAG ATCCGATCCA GCCTCGCATC     1380

GNATGTCCAT GCCGCCATGC GGATGGATAA TAACTGTACA GTGCCTCTTT GATAGGGTCT     1440

GGGCGGCAGG AACTAGCGAC CCGACCAATC GTTTATGCTC TTGCACTGTC CGTCTACACC    1500

GTGTCCCGAT CGATTCCACT GCCTGTGCGT ACGAGTAGGG CTGGGCCAGT AGGGATCTTT    1560

CTCGCCAATC AGCCCGCATA TATGGACCCA GTCAGTAATT GGCTCGCAAG TCACAACAGA    1620

TCTCGATCGG TCTGTTGTAC CAATCTACGT ACTAGCAACA TGTACACGCA CGTACCGAAG    1680

CGGGCGTAAA ACGTTGTCAC GATACAAACT TTCGGCGGCA AGAGCATGCG GCGCGCTGAG    1740

CGCAGCGCAG CGCAGTCGTC CGGTCGTCCC ATCGCGGCCG TTTTCGGCGT ACGTACGGCG    1800

GTACGGGCTA CGGAGCACTG ACTGACTCGT CGGCCGTCCA ACTGTGTAGT CCGCCGATAC    1860

CGCCTGGGCC AATAGCGGAA TAGCCCAAGG CGCGAGACGG CGGCGTCACA CATCGGCGCA    1920

GTTGGTTGGG TCGAGCTCCC AACCAACTCG CTCCCGCGCC AGCCAAGCCA GCCACGACCC    1980

ACGAGCCACC ACCATTACCC GCCCGCCCGC CACAGGCCAC ATCGTTTCCG GCCCTGCTCG    2040

GCTATATATC CGCGAGCATC TGCATATCGC CATATCCCCG CCCCGGGCAC CGCGAGCTAG    2100

CTAGCTACTG ACACCCGGCG CCGGCGCCGA GTACAATACA AGGAAAGCAG CATGGTGTTC    2160

GAGCAGCATG AGGAGGAGGC GGTGGCGCCG GGCGCGGTGC ACGGGCACCG GCTCTCCACG    2220

GTGGTGCCGA GCTCGGTGAC GGGGGAGGTG GACTACGCGC TGGCGGACGC GGACCTGGCC    2280

TTCAAGCTGC ACTACCTGCG CGGGGTGTAC TACTACCGGT CCGGGACGG CCTCGCCACC     2340

AAGGTGCTCA AGGACCCCAT GTTACCGTGG CTGGACGACC ACTTCCCCGT GGCCGGCCGC    2400

GTCCGCCGCG CCGAGACGGA GGGGGACGGC GCGCCGCGCC GGCCCTACAT CAAGTGCAAC    2460

GACTGCGGCG TGCGCATCGT GGAGGCCAGG TGCGACCGCG ACATGGCCGA GTGGATCCGC    2520

GACGCCGCGC CCGGCAGGAT CAGGCAGCTC TGCTACGACA AGGTGCTCGG TCCCGAGCTC    2580
```

```
TTCTTCTCGC CGCTGCTCTA CGTCCAGGTA ACCGTCCTCC GTACGTCGTC GTAGAGAGGT   2640

GGAGATTTTT GTGGTCGGAT TTCTGGCATC GCTGGTTGCC TGCTCCCAGA CCAGTCCCTG   2700

CTGGTGACGG CAGGAGAGGA GACGCATGCA GGCTGTAGCT TTCGGTATGG TTACGGNCAG   2760

TGCAGTTGAG CAAGCTTTTA ATTGTGGTGC GGCAGTAGTA CCTGCTAACC ACCATCAGAC   2820

ATTTATACTG ACTGTCCAGT GGCCACCTAG AGCTGGTCAC CGACTGCAAC CCCCCGTCCC   2880

CGTGTCACCA TCATGCCACA ACTGTGTAGA TAGTGTCTGT CGACCCGGCT GTCACCACTA   2940

CTACTAGTTC AGACTGGACC GCTTCTCTGA ACAAGCAGTT AAGTACCCCC ATTCATCTGC   3000

CGGCTCATGA AGACGGCGG CGGGTTCGTC GTGAGACTGT CGGGTCGGTG TCGCACGAGT    3060

AATTGCTACG CCGGGCGGG ATGGCGTACT CCCATTCATC TGCCGCCGCC CACGTTGAAG    3120

CGGGCGCTTG GGACCAAAGA TCAGCACCCA CAGCCTTGCA ATCAATTCAC TCCCTCGTAG   3180

TACTACCTAG CTCTGACATA AAAACTAGTA CAGTACCATT GAAGCCGATA GCCGATAGAT   3240

TGGAATATTG ATGTCACGAT TTAGTATCAG TGAGAAGATC ATCAAAGCCC AAGCAGTACA   3300

CGAAGAATGG GCCAGCACCA GTCGGCATAG GGTTTATGGA TCGCCTCCCT GGCGGGTGGT   3360

GCATTACGAT CTGCCTTTTT TCATGTAGGC CCAATGCGTT GGTTGCATTA TTGTCTCACT   3420

TGTTTACCCA AATAGTACTA CTCTACTACT ACTAGTACCC ACATAGCACG TACGGAGTAT   3480

GAAGTCAATC AAAGGTGCAA ATCACGGCTT TGTATACTAG CTAGACTAGT CTATTACAGT   3540

ACAGACAATT ACTGCAAACT AATTGTGCTG GTCGATTACT TCTGTTACTA AAGGCATGTA   3600

CAACTTAGAT ACAACTGCAC GGTACTCCAA GTATAAGACA CAACTAAAAC ACAATATAAT   3660

ACAGTGGTCA TATCTAAAAC ATGTGTCTTA CCATATTTAT TGTACCAATC AGGGCATTCA   3720

ATAAATTAAA GTGACCAATC AGATAGTCTC ATGTCTCGAA TATAGAGCTA AGACACCGTG   3780

TCTTCGTCAA AATACATGTC TTGAGATTTT TTACATTCAC CCTCCTAGAC ACACTCTAAG   3840

ACACAACTTA AGACACCCCA CGGTACATGC CCTAACTACG TACTCCCTCC GTCCTTTTTT   3900

ATTTATCGTT TCTTTGGTCA CAGATCACAA ACTTCAAATG CGGTGGGCTG GCGCTGGGGT   3960

TCAGCTGGGC GCACCTCATC GGCGACATCC CGTCGGCCGC CACCTGTTTC AACAAGTGGG   4020

CGCAGATCCT GAGCGGCAAG AAGCCGGAAG CCACCGTCCT CACCCCGCCG AACCAGCCGC   4080

TGCAGGGCCA GTCCCCCGCG GCGCCGCGCT CCGTCAAGCA GGTGGGGCCC ATCGAGGACC   4140

TGTGGCTGGT CCCCGCGGGC CGCGACATGG CGTGCTACTC CTTCCACGTC AGCGACGCGG   4200

TGCTCAAGAA GCTCCACCAG CAGCAGAATG GGCGCCAGGA CGCGGCCGCT GGCACCTTCG   4260

AGCTCGTGTC GGCGCTGGTG TGGCAGGCGG TGGCCAAGAT CAGGGGCGAC GTGGACACCG   4320

TGACCGTGGT CAGGGCCGAC GCCGCCGGCC GGAGCGGCAA GTCGCTGGCC AACGAGATGA   4380

AGGTCGGGTA CGTGGAGTCG GCGGGGTCGT CGCCGGCGAA GACGGACCTC GCGGAGCTGG   4440

CGGCGCTGCT GGCCAAGAAC CTGGTCGACG AGACCGCCGC GGTGGCGGCG TTCCAGGGGG   4500

ACGTGCTCGT GTACGGCGGC GCCAACCTGA CGCTCGTGGA CATGGAGCAG GTGGACCTGT   4560

ACGGGCTCGA GATCAAGGGG CAGCGCCCGG TCCACGTGGA GTACGGCATG GACGGCGTCG   4620

GCGACGAGGG CGCGGTGCTG GTGCAGCCCG ACGCCGACGG GCGCGGCCGC CTCGTCACGG   4680

CGGTTTTGCC CGGCGACGAG ATCGACAGCC TCCGCGCAGC GCTCGGTAGC GCGCTGCAGG   4740

TCGCCTGAAA ACTCTAGTAC GTATCATAAT ACTACGCTGC TGCCTACGTG CTCGTTGCAT   4800

CGTTCGGTTT CGCGATATCA GAGTACCACC TCTTGAAGAA AGTGTAGTAG CGTAATGAGG   4860

CGTGACTAGT GATGGGATGT ATTGTATTGC AGGATGTTGC GCAAATACTG TGGTCGATTT   4920
```

-continued

| | | | | |
|---|---|---|---|---|
| GCGATGTTTG | TTCTGTATCG | CATGATGTTT | CCTTAATAAG | CTGCTCGAAT AGATCATGCA | 4980 |
| TGCTCAATGT | ACCAATATTT | ACACTGGAGA | CTAGACAAAA | ACAATCGTTT GATACAGCAT | 5040 |
| GGTCTTGGGT | GTTTGCACAA | AGTTTTTTGC | TTGCTTGGAT | GTTGGTTAAA TTGTTTCTGA | 5100 |
| ATTTCAGAAG | CACATGTTTA | CTTGGCAAAC | AGTTTGTTGT | CGTCTGAAAT TCGTAGTTAC | 5160 |
| CGAGCGGCAA | ATGTTTGGGT | ACAGTTTGTT | ACTTGGCGCG | AATAAATTCA GAAGCATGTG | 5220 |
| CATGTATGGA | TTTGCTTACC | GAGTGTGGTT | GTTTCGCCCA | CCGAACACTA ACTAGCTTGG | 5280 |
| CTTGACGACC | TGCAAACTGC | GACACTGAAT | CACTGATGTT | GGTTACCGAC AACTGCCAAA | 5340 |
| TTAATACTAG | TTCATATGAA | CTTACACAAC | CATCGGCAAA | GTGAGCTTGG ACGGGTTGTC | 5400 |
| TGCTAGCTTT | TCAGTGTAAT | TTTTTTTGAA | ATAAATACAC | CAGGGTGAGC TTAGACTGTA | 5460 |
| AGTTTTTAAA | CTGCATGTTT | TCTATAGCTT | TTTTTTTAAA | AAAAATGTTT AGTTGACATC | 5520 |
| TGAAGTGTTA | ACGAGTAAGA | TCTATCTACA | TCACGTCAAG | CTAATGTTTT CAAAACCAAA | 5580 |
| TATGGAGCGA | ATTTGAACGA | TTTCAAAAAT | CAAAAGGAGG | TTAAAAGATC AGTTTTCGGA | 5640 |
| CTTCAGCGGA | AAATTGGTAA | GTTAAAATCA | CGTGATTTGG | GCCGGTCTAG AAACAAGTAG | 5700 |
| CCCATCGCAC | CCAACTTGGT | GGCATCGTCA | ATTCTTAGGT | GGAACAAATA AGCCCATCCA | 5760 |
| ATATTATACA | TTTTAAAAAG | TAAGCACAAC | CCAAGCTTAG | ATAACCCCCT TCCTTCCTGT | 5820 |
| ATACAAAACC | AAAGCAAGGC | AAGTCTAGTC | TTGGTTCTCC | GAATTCCAAA CCCTAGCCTC | 5880 |
| GCCTGTTGCG | GCCGCGGCGG | AGATGGCAAA | GTCTCTGCGA | TCCAAGCGCG AGAAGCGGCT | 5940 |
| GCGGACATTG | CGCCGGGAGA | TAGCGGAGCC | CTTCTACGAC | AAGAAGGAGG CCGCCAAGCT | 6000 |
| CACCGCGCAG | GCCGCCGCCC | TTGCTGCTCC | CCCGCTCCAG | GTCCGCGGGC CCCCGCCGTC | 6060 |
| CCAGGATGCC | GGCAGCTCCC | GCGGCGCTAG | CTCAGCCTCG | GCTATGGGTG AGCGCTATAA | 6120 |
| AACTTTTATG | TTTCAGCAGC | CGCCGCGGAT | TGCCTCCGGT | AGTTTCAGGT GGAATAGGAA | 6180 |
| TTTCTCCACG | CGCTTTGTGT | GCTAGTTCAT | TAACGGGTCA | CATTGTTATC TGTTAAAACG | 6240 |
| CTATTCCTAT | ATATTAAACC | AGGGACCCTA | GCTTNCAAAC | TAGGTAGGCC ACGTCATTCA | 6300 |
| GNATTCCTTT | ACCGTCCGAT | CGCTTCTCTA | TGATGCAAAT | CCT | 6343 |